US010133919B2

(12) United States Patent
Bose et al.

(10) Patent No.: US 10,133,919 B2
(45) Date of Patent: *Nov. 20, 2018

(54) MOTION CAPTURE SYSTEM THAT COMBINES SENSORS WITH DIFFERENT MEASUREMENT RANGES

(71) Applicant: Blast Motion Inc., Carlsbad, CA (US)

(72) Inventors: Bhaskar Bose, Carlsbad, CA (US); Piyush Gupta, Vista, CA (US); Scott Lohr, Carlsbad, CA (US)

(73) Assignee: Blast Motion Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,312

(22) Filed: Nov. 21, 2017

(65) Prior Publication Data

US 2018/0096199 A1 Apr. 5, 2018

Related U.S. Application Data

(63) Continuation of application No. 15/490,689, filed on Apr. 18, 2017, now Pat. No. 9,824,264, which is a
(Continued)

(51) Int. Cl.
*H04N 7/18* (2006.01)
*G06K 9/00* (2006.01)
(Continued)

(52) U.S. Cl.
CPC ...... *G06K 9/00342* (2013.01); *A63B 24/0003* (2013.01); *A63B 24/0021* (2013.01);
(Continued)

(58) Field of Classification Search
CPC .................................................. G06K 9/00342
(Continued)

(56) References Cited

U.S. PATENT DOCUMENTS

| 1,712,537 A | 5/1929 | White |
| 3,182,508 A | 5/1965 | Varju |

(Continued)

FOREIGN PATENT DOCUMENTS

| EP | 2025369 A2 | 2/2009 |
| JP | 2002210055 A | 7/2002 |

(Continued)

OTHER PUBLICATIONS

*Zepp Labs, Inc.* v. *Blast Motion, Inc.* Petition for Inter Partes Review of U.S. Pat. No. 8,903,521 filed on Feb. 24, 2016, as IPR2016-00672, and accompanying Declaration of Dr. Steven M. Nesbit.
(Continued)

*Primary Examiner* — Leron Beck
(74) *Attorney, Agent, or Firm* — Arc IP Law, PC; Joseph J. Mayo

(57) ABSTRACT

Motion capture system with a motion capture element that uses two or more sensors to measure a single physical quantity, for example to obtain both wide measurement range and high measurement precision. For example, a system may combine a low-range, high precision accelerometer having a range of −24 g to +24 g with a high-range accelerometer having a range of −400 g to +400 g. Data from the multiple sensors is transmitted to a computer that combines the individual sensor estimates into a single estimate for the physical quantity. Various methods may be used to combine individual estimates into a combined estimate, including for example weighting individual estimates by the inverse of the measurement variance of each sensor. Data may be extrapolated beyond the measurement range of a low-range sensor, using polynomial curves for example, and combined with data from a high-range sensor to form a combined estimate.

16 Claims, 67 Drawing Sheets
(37 of 67 Drawing Sheet(s) Filed in Color)

Related U.S. Application Data continuation of application No. 15/268,501, filed on Sep. 16, 2016, now Pat. No. 9,626,554, which is a continuation-in-part of application No. 15/006,065, filed on Jan. 25, 2016, now Pat. No. 9,633,254, which is a continuation of application No. 13/744,384, filed on Jan. 17, 2013, now Pat. No. 9,247,212, which is a continuation-in-part of application No. 13/358,522, filed on Jan. 26, 2012, now Pat. No. 8,613,676, and a continuation-in-part of application No. 13/351,429, filed on Jan. 17, 2012, now Pat. No. 8,903,521, and a continuation-in-part of application No. 13/306,869, filed on Nov. 29, 2011, now Pat. No. 9,028,337, and a continuation-in-part of application No. 13/298,158, filed on Nov. 16, 2011, now Pat. No. 8,905,855, which is a continuation-in-part of application No. 13/267,784, filed on Oct. 6, 2011, now Pat. No. 9,604,142, which is a continuation-in-part of application No. 13/219,525, filed on Aug. 26, 2011, now Pat. No. 8,941,723, which is a continuation-in-part of application No. 13/191,309, filed on Jul. 26, 2011, now Pat. No. 9,033,810, which is a continuation-in-part of application No. 13/048,850, filed on Mar. 15, 2011, now Pat. No. 8,465,376, which is a continuation-in-part of application No. 12/901,806, filed on Oct. 11, 2010, now Pat. No. 9,320,957, which is a continuation-in-part of application No. 12/868,882, filed on Aug. 26, 2010, now Pat. No. 8,994,826.

(51) Int. Cl.

| | |
|---|---|
| *G06Q 10/06* | (2012.01) |
| *A63F 13/812* | (2014.01) |
| *G06F 19/00* | (2018.01) |
| *G06T 7/246* | (2017.01) |
| *A63B 24/00* | (2006.01) |
| *A63B 69/36* | (2006.01) |
| *A63F 13/212* | (2014.01) |
| *A63F 13/65* | (2014.01) |
| *A63F 13/211* | (2014.01) |
| *G06Q 10/08* | (2012.01) |
| *G06Q 50/00* | (2012.01) |
| *H04M 1/725* | (2006.01) |

(52) U.S. Cl.
CPC .......... *A63B 24/0062* (2013.01); *A63B 69/36* (2013.01); *A63F 13/211* (2014.09); *A63F 13/212* (2014.09); *A63F 13/65* (2014.09); *A63F 13/812* (2014.09); *G06F 19/3481* (2013.01); *G06K 9/0053* (2013.01); *G06Q 10/0639* (2013.01); *G06Q 10/0833* (2013.01); *G06T 7/251* (2017.01); *H04N 7/181* (2013.01); *H04N 7/186* (2013.01); *A63B 2024/0025* (2013.01); *A63B 2220/34* (2013.01); *A63B 2220/40* (2013.01); *A63B 2220/44* (2013.01); *A63B 2220/803* (2013.01); *A63B 2220/806* (2013.01); *A63B 2225/20* (2013.01); *G06Q 50/01* (2013.01); *H04M 1/7253* (2013.01); *H04M 2250/12* (2013.01)

(58) Field of Classification Search
USPC ........................................................ 348/77
See application file for complete search history.

(56) References Cited

U.S. PATENT DOCUMENTS

| | | |
|---|---|---|
| 3,226,704 A | 12/1965 | Petrash |
| 3,270,564 A | 9/1966 | Evans |
| 3,776,556 A | 12/1973 | McLaughlin |
| 3,788,647 A | 1/1974 | Evans |
| 3,792,863 A | 2/1974 | Evans |
| 3,806,131 A | 4/1974 | Evans |
| 3,945,646 A | 3/1976 | Hammond |
| 4,759,219 A | 7/1988 | Cobb et al. |
| 4,898,389 A | 2/1990 | Plutt |
| 4,902,014 A | 2/1990 | Bontomase et al. |
| 4,910,677 A | 3/1990 | Remedio et al. |
| 4,940,236 A | 7/1990 | Allen |
| 4,991,850 A | 2/1991 | Wilhlem |
| 5,056,783 A | 10/1991 | Matcovich et al. |
| 5,086,390 A | 2/1992 | Matthews |
| 5,111,410 A | 5/1992 | Nakayama et al. |
| 5,127,044 A | 6/1992 | Bonito et al. |
| 5,184,295 A | 2/1993 | Mann |
| 5,230,512 A | 7/1993 | Tattershall |
| 5,233,544 A | 8/1993 | Kobayashi |
| 5,249,967 A | 10/1993 | O'Leary et al. |
| 5,259,620 A | 11/1993 | Marocco |
| 5,283,733 A | 2/1994 | Colley |
| 5,298,904 A | 3/1994 | Olich |
| 5,332,225 A | 7/1994 | Ura |
| 5,333,061 A | 7/1994 | Nakashima et al. |
| 5,364,093 A | 11/1994 | Huston et al. |
| 5,372,365 A | 12/1994 | McTeigue et al. |
| 5,441,256 A | 8/1995 | Hackman |
| 5,441,269 A | 8/1995 | Henwood |
| 5,443,260 A | 8/1995 | Stewart et al. |
| 5,486,001 A | 1/1996 | Baker |
| 5,524,081 A | 6/1996 | Paul |
| 5,542,676 A | 8/1996 | Howe et al. |
| 5,592,401 A | 1/1997 | Kramer |
| 5,610,590 A | 3/1997 | Johnson et al. |
| 5,638,300 A | 6/1997 | Johnson |
| 5,665,006 A | 9/1997 | Pellegrini |
| 5,688,183 A | 11/1997 | Sabatino et al. |
| 5,694,340 A | 12/1997 | Kim |
| 5,707,299 A | 1/1998 | McKenna |
| 5,772,522 A | 6/1998 | Nesbit |
| 5,779,555 A | 7/1998 | Nomura et al. |
| 5,792,001 A | 8/1998 | Henwood |
| 5,819,206 A | 10/1998 | Horton |
| 5,826,578 A | 10/1998 | Curchod |
| 5,868,578 A | 2/1999 | Baum |
| 5,904,484 A | 5/1999 | Burns |
| 5,941,779 A | 8/1999 | Zeiner-Gundersen |
| 5,973,596 A | 10/1999 | French et al. |
| 5,993,333 A | 11/1999 | Heckaman |
| 5,998,968 A | 12/1999 | Pittman et al. |
| 6,012,995 A | 1/2000 | Martin |
| 6,030,109 A | 2/2000 | Lobsenz |
| 6,044,704 A | 4/2000 | Sacher |
| 6,073,086 A | 6/2000 | Marinelli |
| 6,224,493 B1 | 5/2001 | Lee et al. |
| 6,248,021 B1 | 6/2001 | Ognjanovic |
| 6,253,159 B1 | 6/2001 | Bett et al. |
| 6,254,492 B1 | 7/2001 | Taggett |
| 6,266,623 B1 | 7/2001 | Vock et al. |
| 6,293,802 B1 | 9/2001 | Ahlgren |
| 6,366,205 B1 | 4/2002 | Sutphen |
| 6,441,745 B1 | 8/2002 | Gates |
| 6,456,938 B1 | 9/2002 | Barnard |
| 6,537,076 B2 | 3/2003 | McNitt |
| 6,540,620 B1 | 4/2003 | Consiglio |
| 6,567,536 B2 | 5/2003 | McNitt |
| 6,582,328 B2 | 6/2003 | Kuta et al. |
| 6,611,141 B1 | 8/2003 | Schulz |
| 6,697,820 B1 | 2/2004 | Tarlie |
| 6,705,942 B1 | 3/2004 | Crook et al. |
| 6,746,336 B1 | 6/2004 | Brant et al. |
| 6,757,572 B1 | 6/2004 | Forest |
| 6,774,932 B1 | 8/2004 | Ewing et al. |

(56) References Cited

U.S. PATENT DOCUMENTS

| | | |
|---|---|---|
| 6,802,772 B1 | 10/2004 | Kunzle et al. |
| 6,868,338 B1 | 3/2005 | Elliott |
| 6,900,759 B1 | 5/2005 | Katayama |
| 6,908,404 B1 | 6/2005 | Gard |
| 6,923,729 B2 | 8/2005 | McGinty et al. |
| 7,004,848 B2 | 2/2006 | Konow |
| 7,021,140 B2 | 4/2006 | Perkins |
| 7,034,694 B2 | 4/2006 | Yamaguchi et al. |
| 7,037,198 B2 | 5/2006 | Hameen-Anttila |
| 7,092,846 B2 | 8/2006 | Vock et al. |
| 7,118,498 B2 | 10/2006 | Meadows et al. |
| 7,121,962 B2 | 10/2006 | Reeves |
| 7,143,639 B2 | 12/2006 | Gobush |
| 7,160,200 B2 | 1/2007 | Grober |
| 7,175,177 B2 | 2/2007 | Meifu et al. |
| 7,205,894 B1 | 4/2007 | Savage |
| 7,212,943 B2 | 5/2007 | Aoshima et al. |
| 7,219,033 B2 | 5/2007 | Kolen |
| 7,234,351 B2 | 6/2007 | Perkins |
| 7,264,554 B2 | 9/2007 | Bentley |
| 7,283,647 B2 | 10/2007 | McNitt |
| 7,421,369 B2 | 9/2008 | Clarkson |
| 7,433,805 B2 | 10/2008 | Vock et al. |
| 7,457,439 B1 | 11/2008 | Madsen |
| 7,457,724 B2 | 11/2008 | Vock et al. |
| 7,492,367 B2 | 2/2009 | Mahajan et al. |
| 7,494,236 B2 | 2/2009 | Lim |
| 7,499,828 B2 | 3/2009 | Barton |
| 7,561,989 B2 | 7/2009 | Banks |
| 7,623,987 B2 | 11/2009 | Vock et al. |
| 7,627,451 B2 | 12/2009 | Vock et al. |
| 7,689,378 B2 | 3/2010 | Kolen |
| 7,713,148 B2 | 5/2010 | Sweeney |
| 7,731,598 B1 | 6/2010 | Kim et al. |
| 7,736,242 B2 | 6/2010 | Stites et al. |
| 7,771,263 B2 | 8/2010 | Telford |
| 7,780,450 B2 | 8/2010 | Tarry |
| 7,800,480 B1 | 9/2010 | Joseph et al. |
| 7,813,887 B2 | 10/2010 | Vock et al. |
| 7,831,212 B1 | 11/2010 | Balardeta et al. |
| 7,871,333 B1 | 1/2011 | Davenport |
| 7,966,154 B2 | 6/2011 | Vock et al. |
| 7,983,876 B2 | 7/2011 | Vock et al. |
| 8,036,826 B2 | 10/2011 | MacIntosh et al. |
| 8,117,888 B2 | 2/2012 | Chan et al. |
| 8,172,722 B2 | 5/2012 | Molyneux et al. |
| 8,231,506 B2 | 7/2012 | Molyneux et al. |
| 8,249,831 B2 | 8/2012 | Vock et al. |
| 8,257,191 B2 | 9/2012 | Stites et al. |
| 8,282,487 B2 | 10/2012 | Wilson et al. |
| 8,314,840 B1 | 11/2012 | Funk |
| 8,352,211 B2 | 1/2013 | Vock et al. |
| 8,400,548 B2 | 3/2013 | Bilbrey et al. |
| 8,425,292 B2 | 4/2013 | Lui et al. |
| 8,477,027 B2 | 7/2013 | Givens |
| 8,527,228 B2 | 9/2013 | Panagas |
| 8,565,483 B2 | 10/2013 | Nakaoka |
| 8,589,114 B2 | 11/2013 | Papadourakis |
| 8,696,482 B1 | 4/2014 | Pedenko et al. |
| 8,723,986 B1 | 5/2014 | Merrill |
| 8,725,452 B2 | 5/2014 | Han |
| 8,764,576 B2 | 7/2014 | Takasugi |
| 8,781,610 B2 | 7/2014 | Han |
| 8,831,905 B2 | 9/2014 | Papadourakis |
| 8,876,621 B2 | 11/2014 | Shibuya |
| 8,888,603 B2 | 11/2014 | Sato et al. |
| 8,905,856 B2 | 12/2014 | Parke et al. |
| 8,929,709 B2 | 1/2015 | Lokshin |
| 8,944,932 B2 | 2/2015 | Sato et al. |
| 8,944,939 B2 | 2/2015 | Clark et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,032,794 B2 | 5/2015 | Perkins et al. |
| 9,060,682 B2 | 6/2015 | Lokshin |
| 9,146,134 B2 | 9/2015 | Lokshin et al. |
| 9,656,122 B2 | 5/2017 | Papadourakis |
| 9,694,267 B1 | 7/2017 | Thornbrue et al. |
| 2001/0029207 A1 | 10/2001 | Cameron et al. |
| 2001/0035880 A1 | 11/2001 | Musatov et al. |
| 2001/0045904 A1 | 11/2001 | Silzer, Jr. |
| 2001/0049636 A1 | 12/2001 | Hudda et al. |
| 2002/0004723 A1 | 1/2002 | Meifu et al. |
| 2002/0019677 A1 | 2/2002 | Lee |
| 2002/0049507 A1 | 4/2002 | Hameen-Anttila |
| 2002/0052750 A1 | 5/2002 | Hirooka |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0008722 A1 | 1/2003 | Konow |
| 2003/0073518 A1 | 4/2003 | Marty |
| 2003/0074659 A1 | 4/2003 | Louzoun |
| 2003/0109322 A1 | 6/2003 | Funk et al. |
| 2003/0163287 A1 | 8/2003 | Vock et al. |
| 2003/0191547 A1 | 10/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0268704 A1 | 12/2005 | Bissonnette et al. |
| 2005/0272516 A1 | 12/2005 | Gobush |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0189389 A1 | 8/2006 | Hunter et al. |
| 2006/0199659 A1 | 9/2006 | Caldwell |
| 2006/0247070 A1 | 11/2006 | Funk et al. |
| 2006/0250745 A1 | 11/2006 | Butler et al. |
| 2006/0270450 A1 | 11/2006 | Garratt et al. |
| 2006/0276256 A1 | 12/2006 | Storek |
| 2006/0284979 A1 | 12/2006 | Clarkson |
| 2006/0293112 A1 | 12/2006 | Yi |
| 2007/0052807 A1 | 3/2007 | Zhou et al. |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0129178 A1 | 6/2007 | Reeves |
| 2007/0135225 A1 | 6/2007 | Nieminen |
| 2007/0135237 A1 | 6/2007 | Reeves |
| 2007/0219744 A1 | 9/2007 | Kolen |
| 2007/0265105 A1 | 11/2007 | Barton |
| 2007/0270214 A1 | 11/2007 | Bentley |
| 2007/0298896 A1 | 12/2007 | Nusbaum |
| 2008/0027502 A1 | 1/2008 | Ransom |

(56) References Cited

U.S. PATENT DOCUMENTS

| | | |
|---|---|---|
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0182685 A1 | 7/2008 | Marty et al. |
| 2008/0190202 A1 | 8/2008 | Kulach et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0063778 A1 | 3/2010 | Schrock et al. |
| 2010/0063779 A1 | 3/2010 | Schrock et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0144457 A1 | 6/2010 | Kim |
| 2010/0178994 A1 | 7/2010 | Do et al. |
| 2010/0201512 A1 | 8/2010 | Stirling et al. |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0308105 A1 | 12/2010 | Savarese et al. |
| 2010/0309097 A1 | 12/2010 | Raviv et al. |
| 2010/0323794 A1 | 12/2010 | Su |
| 2011/0004871 A1 | 1/2011 | Liu |
| 2011/0029235 A1 | 2/2011 | Berry |
| 2011/0037778 A1 | 2/2011 | Deng et al. |
| 2011/0050864 A1 | 3/2011 | Bond |
| 2011/0052005 A1 | 3/2011 | Selner |
| 2011/0053688 A1 | 3/2011 | Crawford |
| 2011/0075341 A1 | 3/2011 | Lau et al. |
| 2011/0081981 A1 | 4/2011 | Okamoto |
| 2011/0126184 A1 | 5/2011 | Lisboa |
| 2011/0165998 A1 | 7/2011 | Lau et al. |
| 2011/0195780 A1 | 8/2011 | Lu |
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune et al. |
| 2011/0238308 A1 | 9/2011 | Miller et al. |
| 2011/0305369 A1 | 12/2011 | Bentley et al. |
| 2012/0023354 A1 | 1/2012 | Chino |
| 2012/0052972 A1 | 3/2012 | Bentley |
| 2012/0115626 A1 | 5/2012 | Davenport |
| 2012/0115682 A1 | 5/2012 | Homsi |
| 2012/0116548 A1 | 5/2012 | Goree et al. |
| 2012/0120572 A1 | 5/2012 | Bentley |
| 2012/0157241 A1 | 6/2012 | Nomura et al. |
| 2012/0179418 A1 | 7/2012 | Takasugi et al. |
| 2012/0179742 A1 | 7/2012 | Acharya et al. |
| 2012/0191405 A1 | 7/2012 | Molyneux et al. |
| 2012/0295726 A1 | 11/2012 | Cherbini |
| 2012/0316004 A1 | 12/2012 | Shibuya |
| 2013/0029791 A1 | 1/2013 | Rose et al. |
| 2013/0095941 A1 | 4/2013 | Bentley et al. |
| 2013/0110415 A1 | 5/2013 | Davis et al. |
| 2013/0128022 A1 | 5/2013 | Bose et al. |
| 2013/0173212 A1 | 7/2013 | Saiki et al. |
| 2013/0178304 A1 | 7/2013 | Chan |
| 2013/0191063 A1 | 7/2013 | Nomura |
| 2013/0225309 A1 | 8/2013 | Bentley et al. |
| 2013/0267335 A1 | 10/2013 | Boyd et al. |
| 2013/0271602 A1 | 10/2013 | Bentley et al. |
| 2013/0298668 A1 | 11/2013 | Sato |
| 2013/0319113 A1 | 12/2013 | Mizuta |
| 2013/0330054 A1 | 12/2013 | Lokshin |
| 2013/0332004 A1 | 12/2013 | Gompert et al. |
| 2013/0346013 A1 | 12/2013 | Lokshin |
| 2014/0019083 A1 | 1/2014 | Nakaoka |
| 2014/0100048 A1 | 4/2014 | Ota et al. |
| 2014/0100049 A1 | 4/2014 | Ota et al. |
| 2014/0100050 A1 | 4/2014 | Ota et al. |
| 2014/0135139 A1 | 5/2014 | Shibuya et al. |
| 2014/0156214 A1 | 6/2014 | Nomura |
| 2014/0172873 A1 | 6/2014 | Varoglu et al. |
| 2014/0200092 A1 | 7/2014 | Parke et al. |
| 2014/0200094 A1 | 7/2014 | Parke et al. |
| 2014/0229135 A1 | 8/2014 | Nomura |
| 2014/0229138 A1 | 8/2014 | Goree et al. |
| 2014/0257743 A1 | 9/2014 | Lokshin et al. |
| 2014/0257744 A1 | 9/2014 | Lokshin et al. |
| 2014/0295982 A1 | 10/2014 | Shibuya |
| 2014/0376876 A1 | 12/2014 | Bentley et al. |
| 2014/0378239 A1 | 12/2014 | Sato et al. |
| 2014/0379293 A1 | 12/2014 | Sato |
| 2014/0379294 A1 | 12/2014 | Shibuya et al. |
| 2014/0379295 A1 | 12/2014 | Sato et al. |
| 2015/0007658 A1 | 1/2015 | Ishikawa et al. |
| 2015/0012240 A1 | 1/2015 | Sato |
| 2015/0042481 A1 | 2/2015 | Nomura |
| 2015/0098688 A1 | 4/2015 | Lokshin |
| 2015/0124048 A1 | 5/2015 | King |
| 2015/0131845 A1 | 5/2015 | Forouhar et al. |
| 2015/0154452 A1 | 6/2015 | Bentley et al. |
| 2015/0256689 A1 | 9/2015 | Erkkila et al. |
| 2015/0348591 A1 | 12/2015 | Kaps et al. |

FOREIGN PATENT DOCUMENTS

| | | |
|---|---|---|
| JP | 2004207985 | 7/2004 |
| JP | 2011000367 | 1/2011 |
| JP | 2012196241 | 10/2012 |
| KR | 10-20030085275 | 11/2003 |
| KR | 10-20060041060 | 5/2006 |
| KR | 10-20070119018 | 12/2007 |
| KR | 10-20100074068 | 7/2010 |
| KR | 101079319 | 6/2011 |
| KR | 10-20100020131 | 9/2011 |
| WO | 1994027683 | 12/1994 |
| WO | 2007130057 A1 | 11/2007 |
| WO | 2009056688 A1 | 5/2009 |
| WO | 2011057194 | 5/2011 |
| WO | 2014085744 A1 | 6/2014 |

OTHER PUBLICATIONS

*Zepp Labs, Inc.* v. *Blast Motion, Inc.* Petition for Inter Partes Review of U.S. Pat. No. 9,039,527 filed on Feb. 24, 2016, as IPR2016-00674, and accompanying Declaration of Dr. Steven M. Nesbit.

*Zepp Labs, Inc.* v. *Blast Motion, Inc.* Petition for Inter Partes Review of U.S. Pat. No. 8,941,723 filed on Feb. 24, 2016, as IPR2016-00675, and accompanying Declaration of Dr. Steven M. Nesbit.

(56) References Cited

OTHER PUBLICATIONS

*Zepp Labs, Inc.* v. *Blast Motion, Inc.* Petition for Inter Partes Review of U.S. Pat. No. 8,905,855 filed on Feb. 24, 2016, as IPR2016-00676, and accompanying Declaration of Dr. Steven M. Nesbit.
*Zepp Labs, Inc.* v. *Blast Motion, Inc.* Petition for Inter Partes Review of U.S. Pat. No. 8,944,928 filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", www.electronicdesign.com/communications/wireless-sensor-architecture-uses-bluetooth-standard, Aug. 7, 2000, 5 pages.
Don Tuite, "Motion-Sensing MEMS Gyros and Accelerometers are Everywhere", www.electronicdesign.com/print/analog/motion-sensing-mems-gyros-and-accelerometers-are-everywhere, Jul. 9, 2009, 6 pages.
InvenSense News Release, "InvenSense Unveils World's 1$^{st}$ IMU Solution for Consumer Applications", ir.invensense.com, 2016, 2 Pages.
Dean Takahashi, "Facebook, Twitter, Last.fm coming to Xbox Live this Fall", Jun. 1, 2009, Webpage printout, 5 pages.
The iClub System, Products pages, www.iclub.net, 2001-2005, 5 pages.
Websters New College Dictionary, Definition of "Virtual Reality", Third Edition, 2005, 3 Pages.
SmartSwing, "SmartSwing Introduces Affordable Intelligent Golf Club", www.smartswinnggolf.com , Jan. 2006, 2 pages.
Henrick Arfwedson, et al., "Ericsson's Bluetooth modules", Ericsson Review No. 4, 1999, 8 pages.
ZigBees, "Zigbee information", www.zigbees.com , 2015, 4 pages.
SolidState Technology, "MEMS enable smart golf clubs", www.electroiq.com , 2005, 3 pages.
IGN, "Japanese WII Price Release Date Revealed", www.ign.com , 2006, 1 page.
First Annual Better Golf Through Technology Conference 2006 webpage, www.bettergolfthroughtechnology.com , Massachusetts Institute of Technology, Cambridge Massachusetts, Feb. 2006, 1 page.
Concept2Rowing, "Training" web content, www.concept2.com , 2009, 1 page.
Expresso, Products pages, www.expresso.com/products , 2009, 2 pages.
Manish Kalia, et al., "Efficient Policies for Increasing Capacity in Bluetooth: An Indoor Pico-Cellular Wireless System", IBM India Research Laboratory, Indian Institute of Technology, 2000, 5 pages.
R. Rao, et al., "Demand-Based Bluetooth Scheduling", Pennsylvania State University, 2001, 13 pages.
International Search Report received in PCT/US2016/042668, dated Oct. 4, 2016, 21 pages.
International Search Report received in PCT/US2016/042671, dated Oct. 13, 2016, 17 pages.
International Search Report and Written Opinion received in PCT/US2016/042676, dated Oct. 24, 2016 (12 pages).
International Preliminary Report on Patentability received in PCT/US2015/026917, dated Nov. 3, 2016 (5 pages).
International Search Report received for PCT Application No. PCT/US2012/065716, dated Jan. 3, 2013, 10 pages.
MyCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, dated Mar. 6, 2012, 8 pages.
International Search Report received for PCT Application No. PCT/US2011/049461, dated Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.
International Search Report for PCT Application No. PCT/US2013/021999, dated Apr. 30, 2013, 8 pages.
International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
MiCoach Pacer User Manual, 31 pages, (2009).
Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
TRACE—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
Pocketpro Golf Designs, PocketPro Full Swing Analysis in Your Pocket, www.PocketPro.org, (2011).
Clemson University, Golf Shot Tutorial, http://www.webnucleo.org/home/online_tools/newton/0.4/html/about_this_tool/tutorials/golf_1.shp.cgi, retrieved on Nov. 10, 2011.
MiCoach SPEED_CELL TM, User Manual, 23 pages, (2011).
Nike+iPod, User Guide, 32 pages (2010).
SureShotGPS SS9000X, Intelligent Touch, Instruction Manual, 25 page, 2011.
ActiveReplay, "TRACE—The Most Advanced Activity Monitor for Action Sports", http://www.kickstarter.com/projects/activereplay/trace-the-most-advanced-activity-monitor-for-actio, 13 pages, Oct. 1, 2013.
Zepp Golfsense@Launch2011, https://www.youtube.com/watch?v=VnOcu8szjIk (video), Mar. 14, 2011.
Epson US Newsroom, "Epson America Enters Sports Wearables Market with Introduction of M-Tracer MT500GII Golf Swing Analyzer", www.news.epson.com, Jan. 5, 2015, 4 pages.
International Search Report and Written Opinion dated Dec. 22, 2015 received in PCTUS1561695, 7 pages.
Search Report Received in PCT2013021999 dated Jan. 21, 2016.
Patent Examination Report received in Australia Application No. 2011313952, dated Mar. 15, 2016, 5 pages.
"About Banjo" webpages retrieved from internet, dated 2015.
International Search Report and Written Opinion mailed in PCTUS1642674 dated Aug. 12, 2016, 9 pages.

(56) References Cited

OTHER PUBLICATIONS

International Preliminary Report on Patentability in PCTUS2015061695, dated Jun. 1, 2017, 5 pages.
European Search Report received in PCTUS2015026896 dated May 11, 2017, 13 pages.
International Search Report and Written Opinion received in PCT/US2017/52114, dated Oct. 3, 9 pages.
International Search Report and Written Opinion Received in PCT/US2017/37987, dated Nov. 9, 2017, 12 pages.
Supplementary Extended European Search Report received in 11820763.8 dated Nov. 13, 2017, 16 pages.
Supplementary Extended European Search Report received in 11833159.4 dated Nov. 6, 2017, 14 pages.
Supplementary Partial European Search Report received from EP Application Serial No. 11820763.8, dated Aug. 8, 2017, 15 pages.
Supplementary Partial European Search Report received from EP Application Serial No. 11833159.4, dated Aug. 8, 2017, 15 pages.
David E. Culler, Et al., "Smart Sensors to Network the World", published in Scientific American Magazine, No. Jun. 2004, dated Jun. 1, 2004, pp. 85-91.
International Search Report and Written Opinion received in PCT/US2017/039209, dated Aug. 24, 2017, 7 pages.

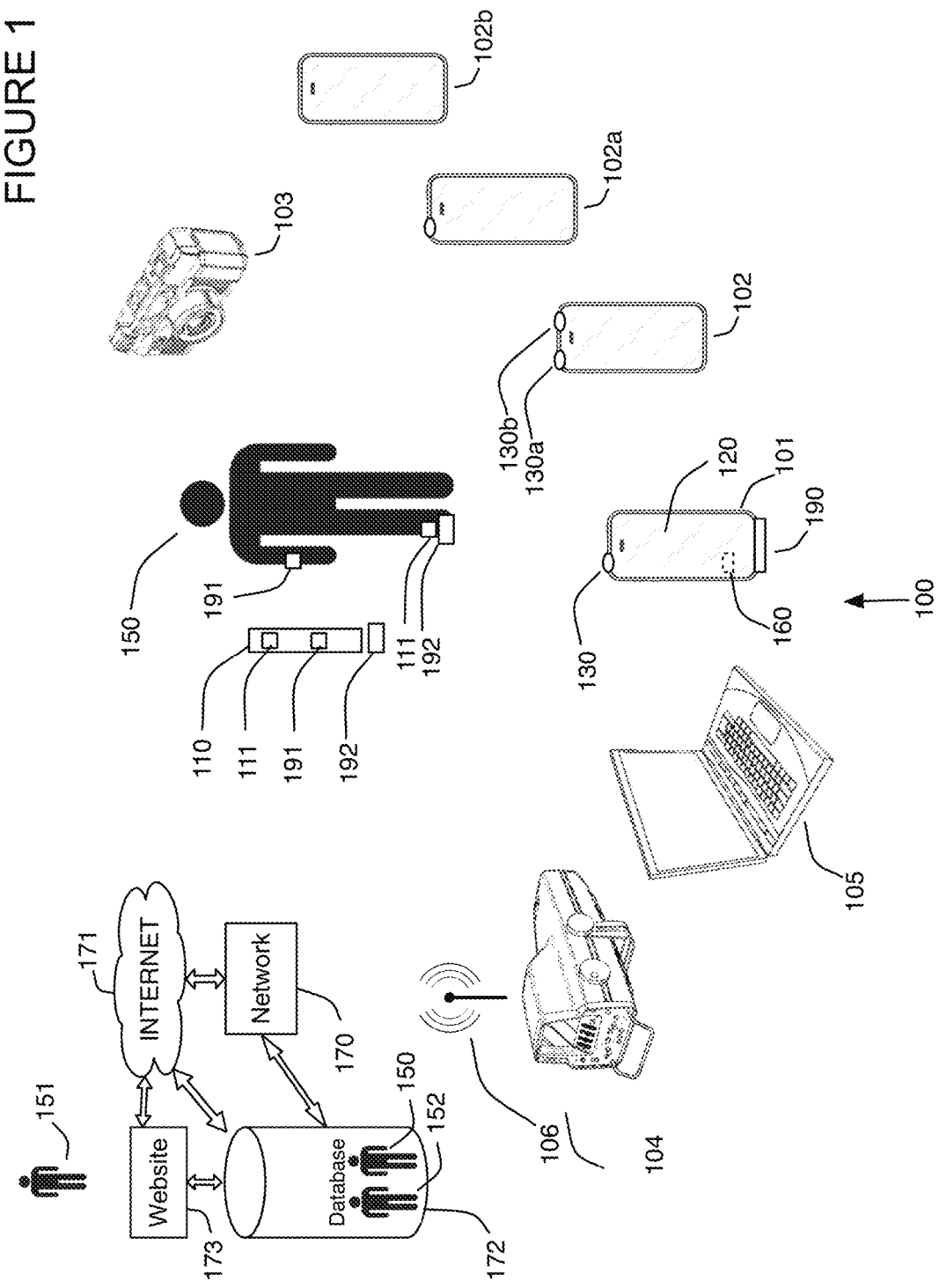

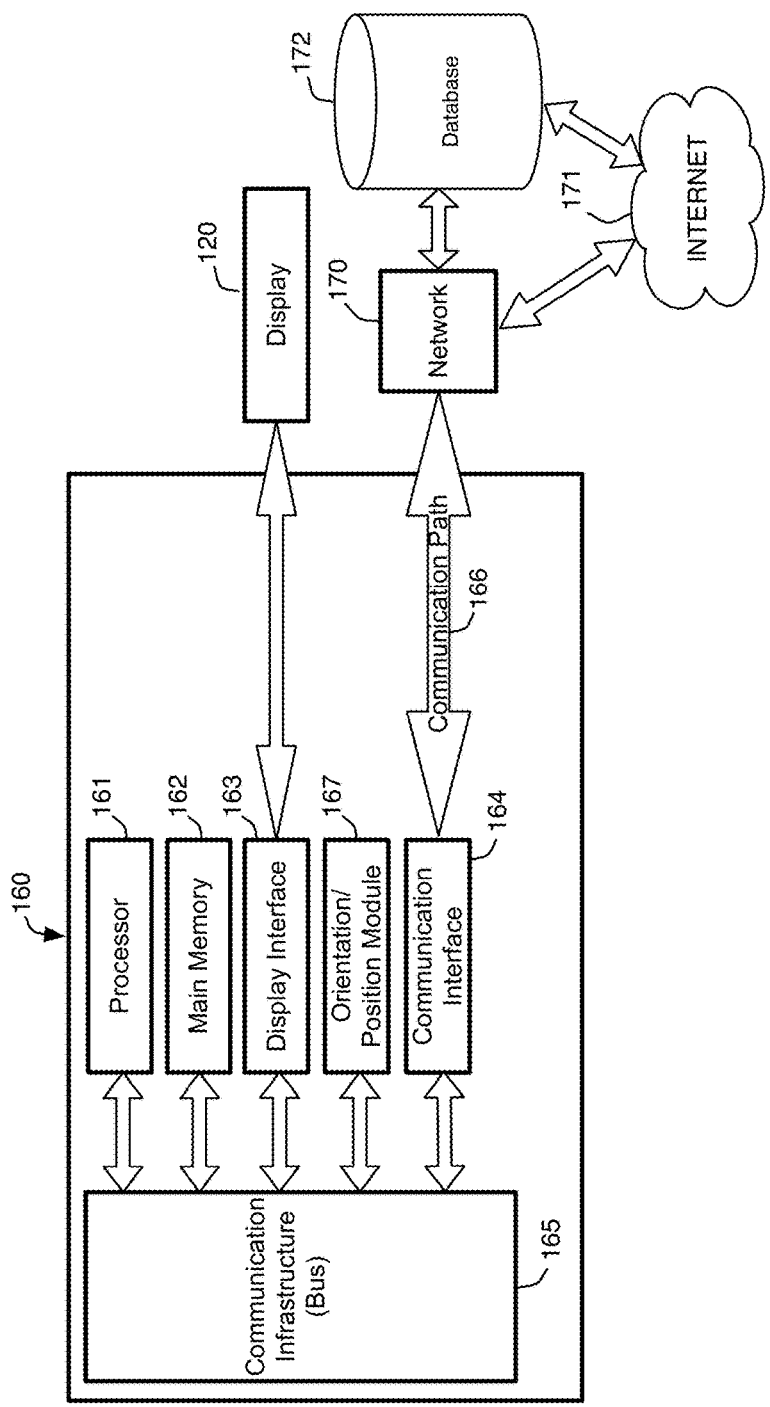

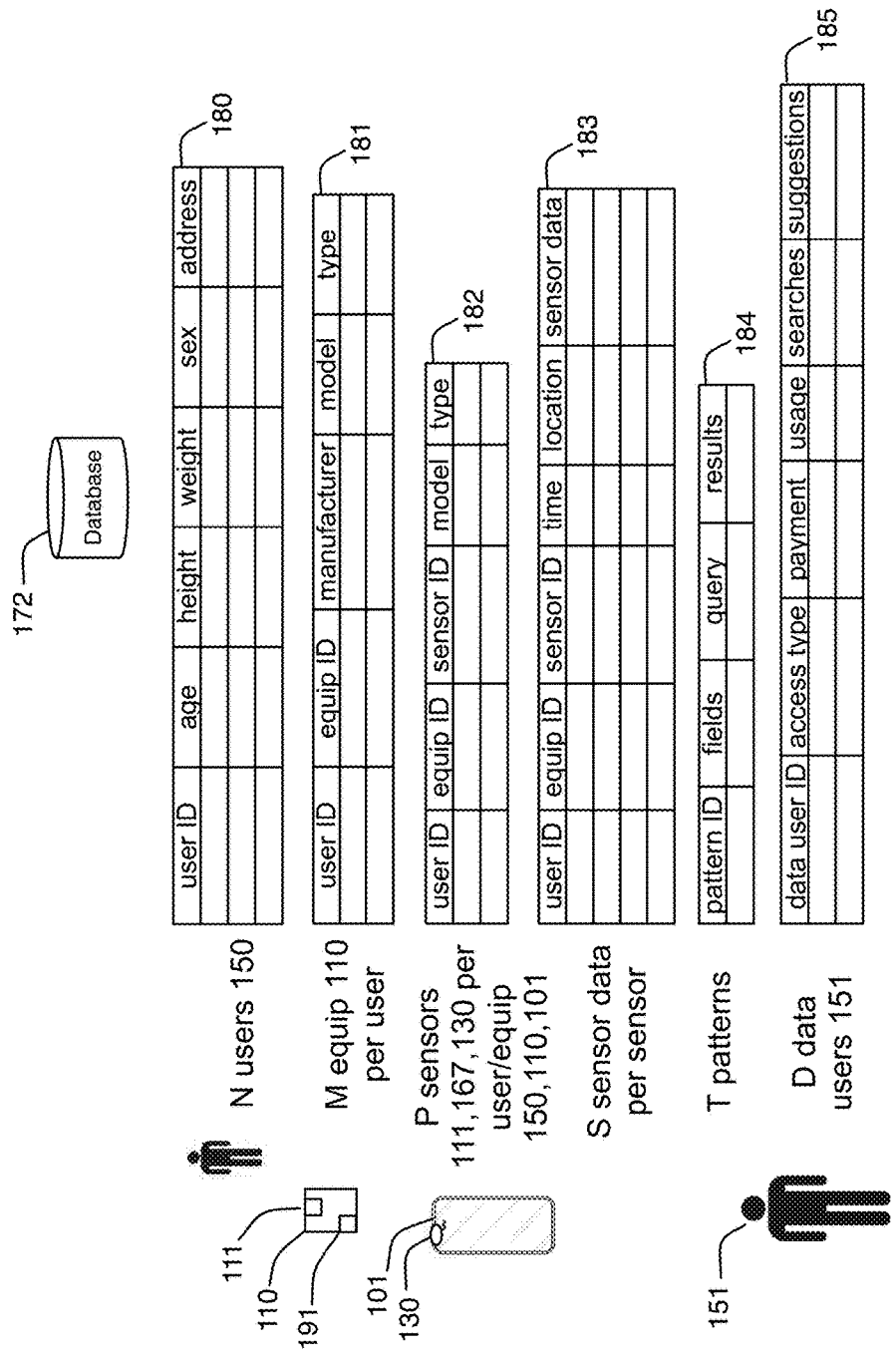

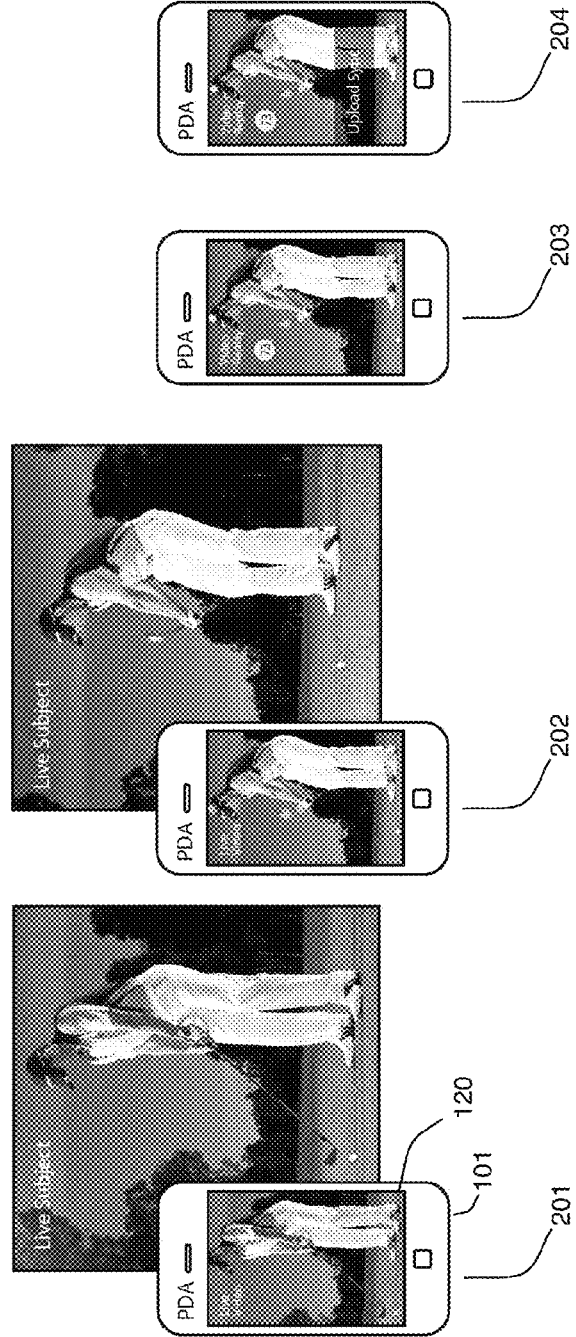

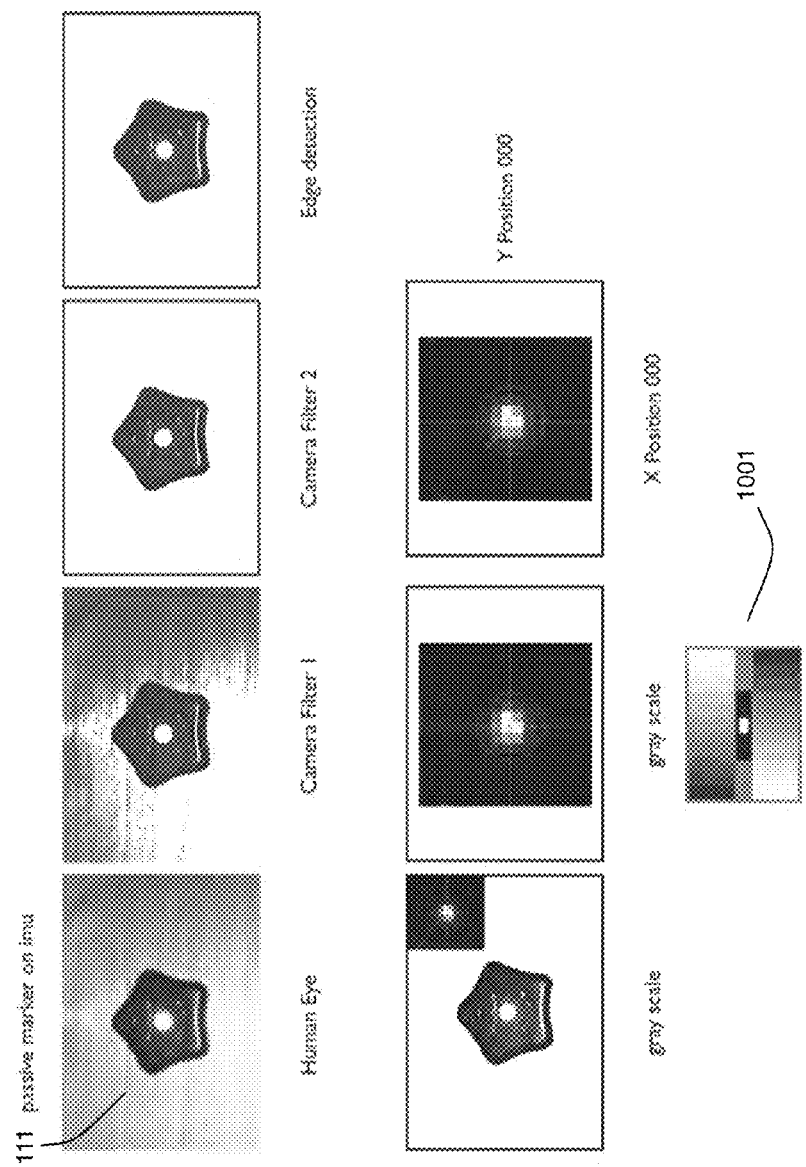

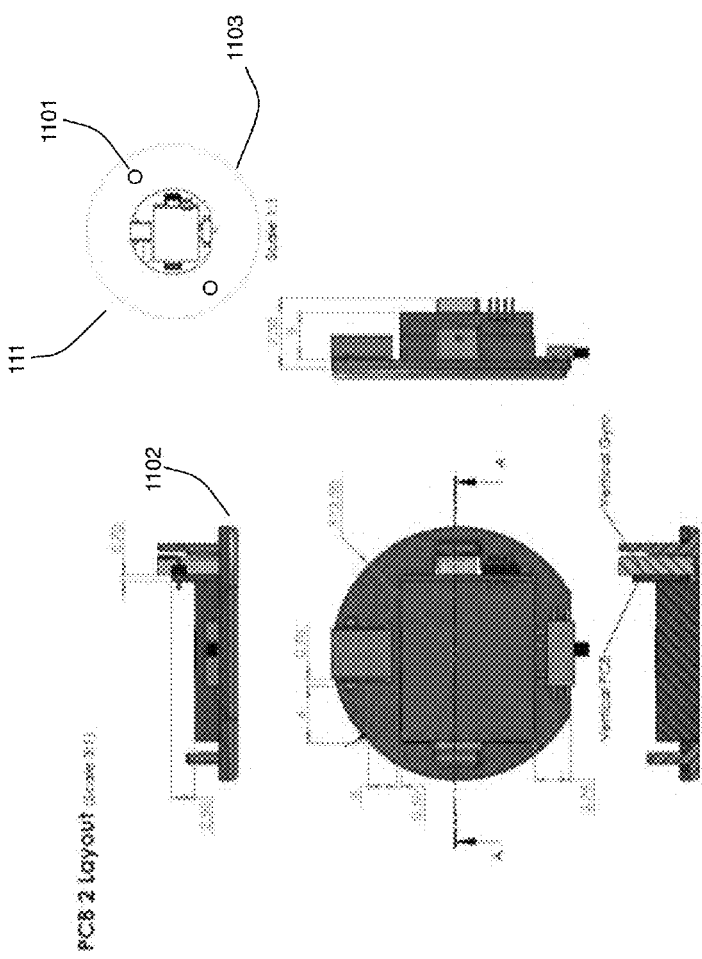

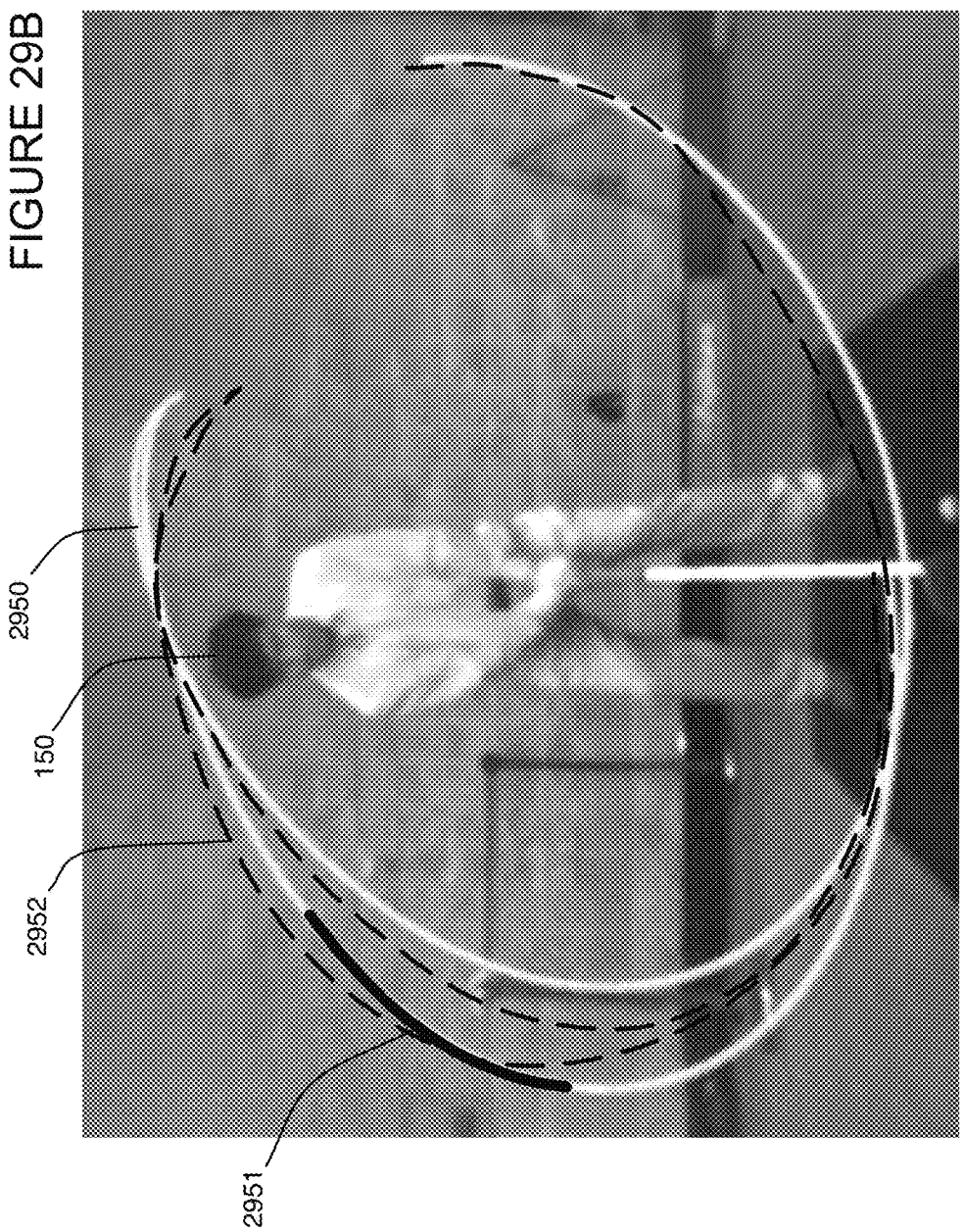

3201

Club Handle Speed: 1.63 MPH
Club Head Speed: 2.64 MPH
Putting Stroke Efficiency: 67%
Smash Factor: 1.25

FIGURE 37

$$\ddot{x} = -Bu(C_D u_x + C_L u_y sin(\alpha))$$

$$\ddot{y} = -Bu(C_D u_y - C_L(u_x sin(\alpha) - u_z cos(\alpha)))$$

$$\ddot{z} = -g - Bu(C_D u_z - C_L u_y cos(\alpha))$$

$$C_D = \frac{40.0 ft/s}{v}$$

$$C_L = \frac{33.4 ft/s}{v}$$

3701

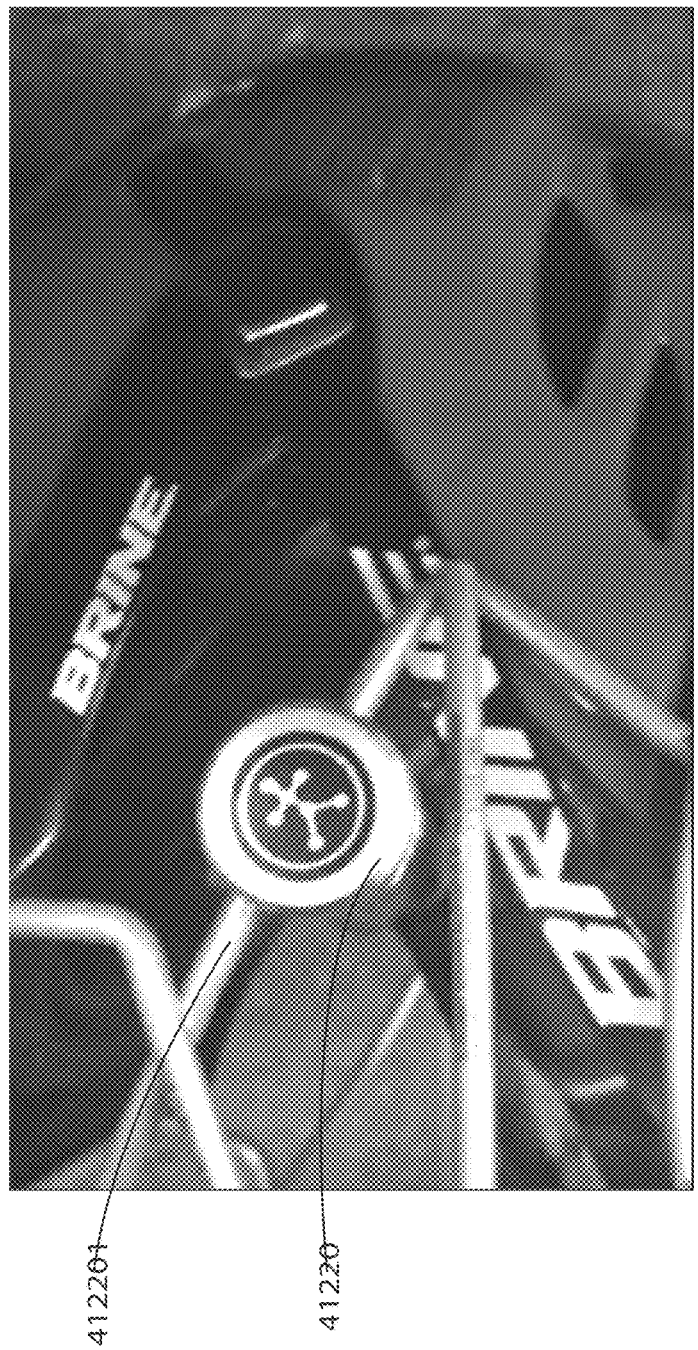

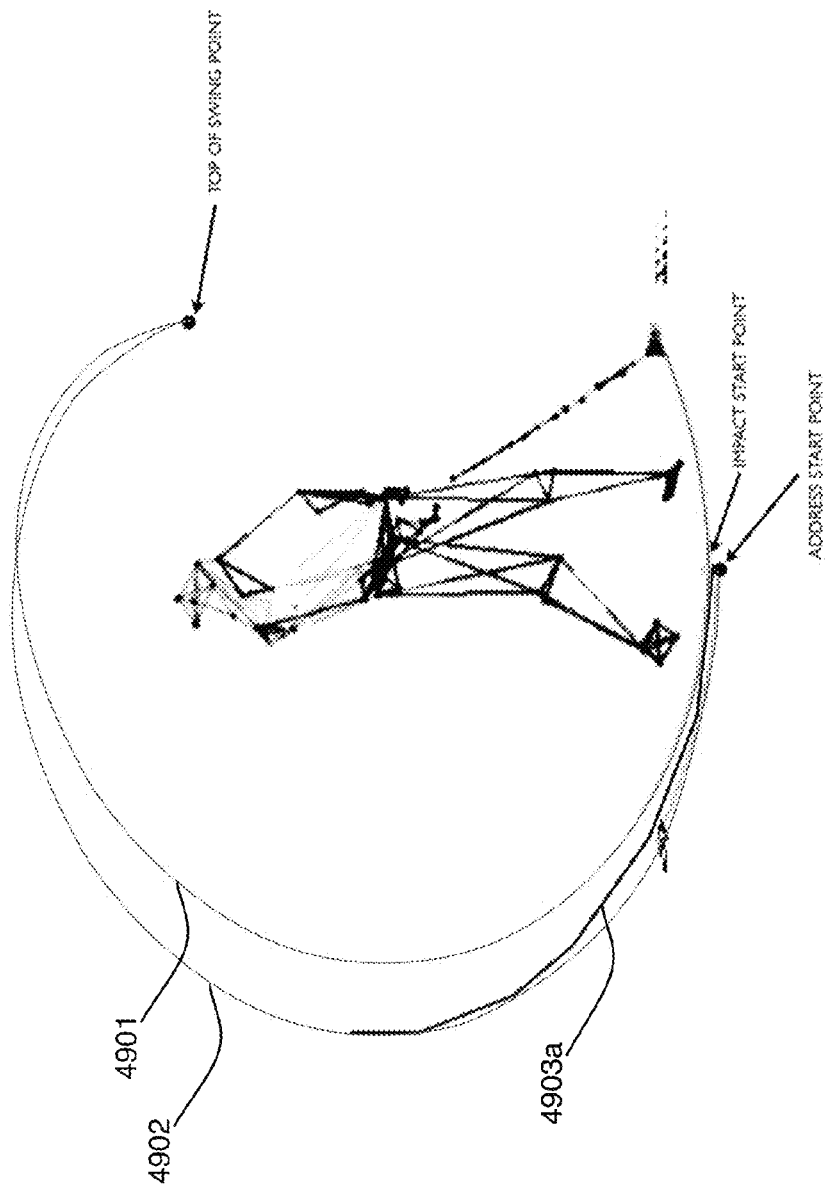

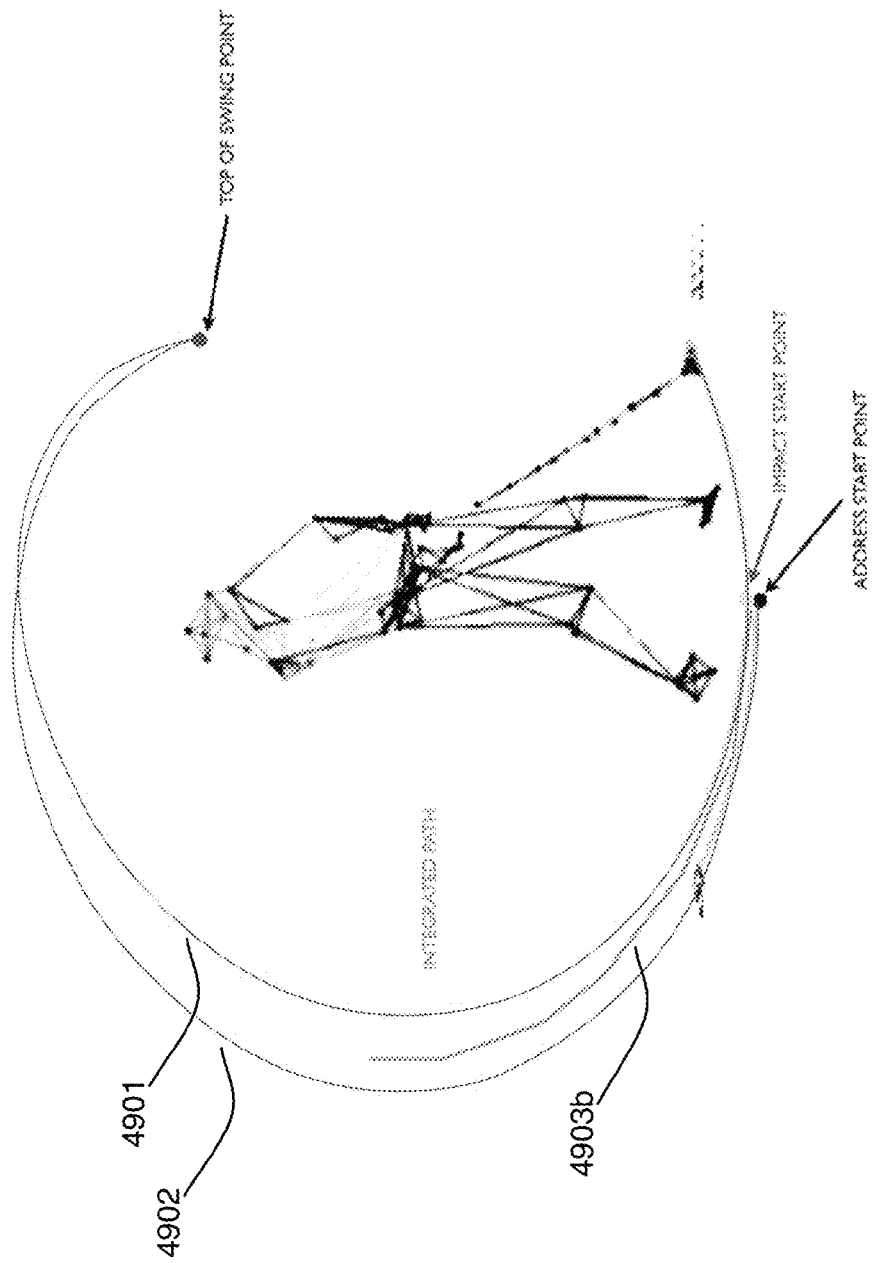

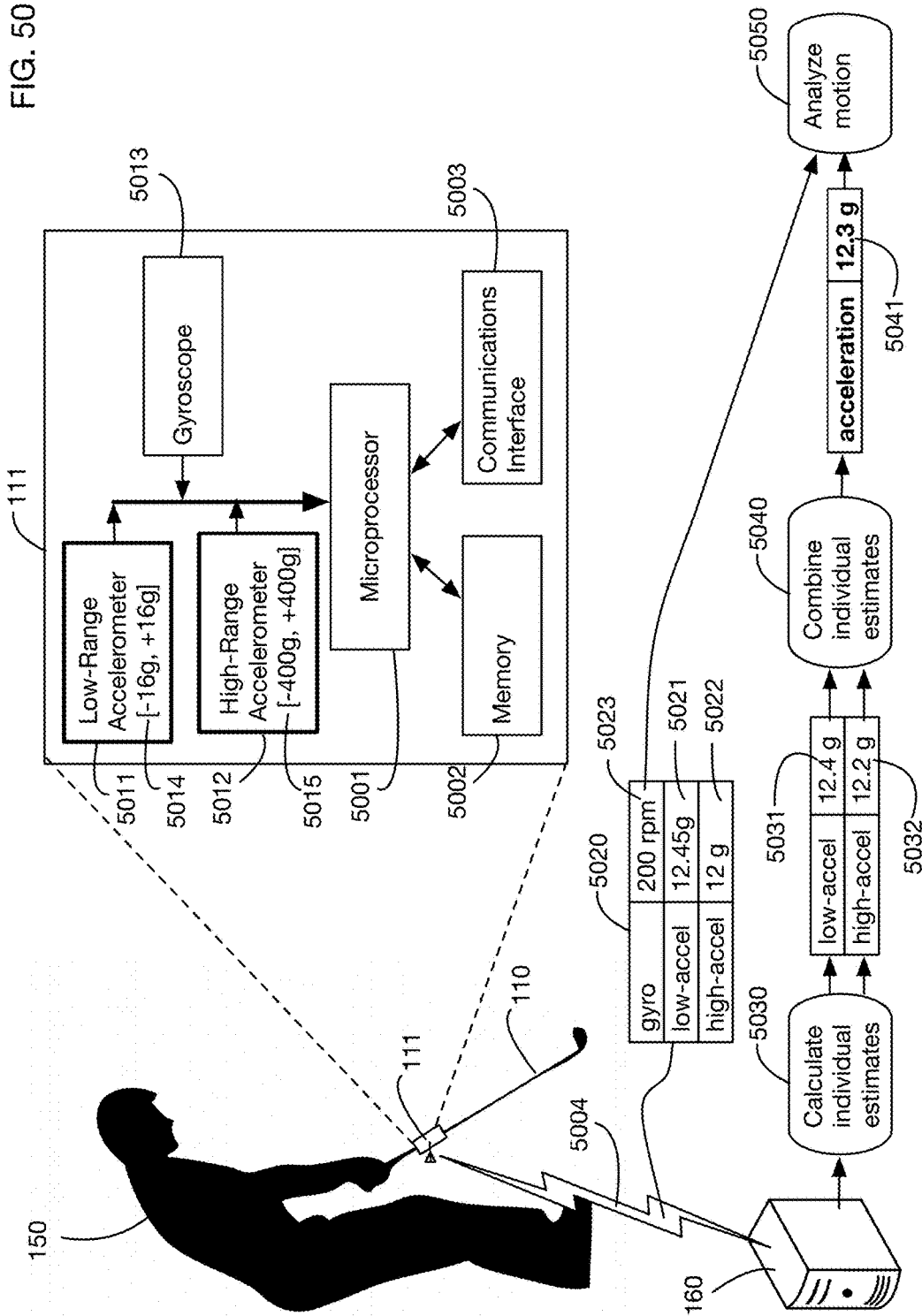

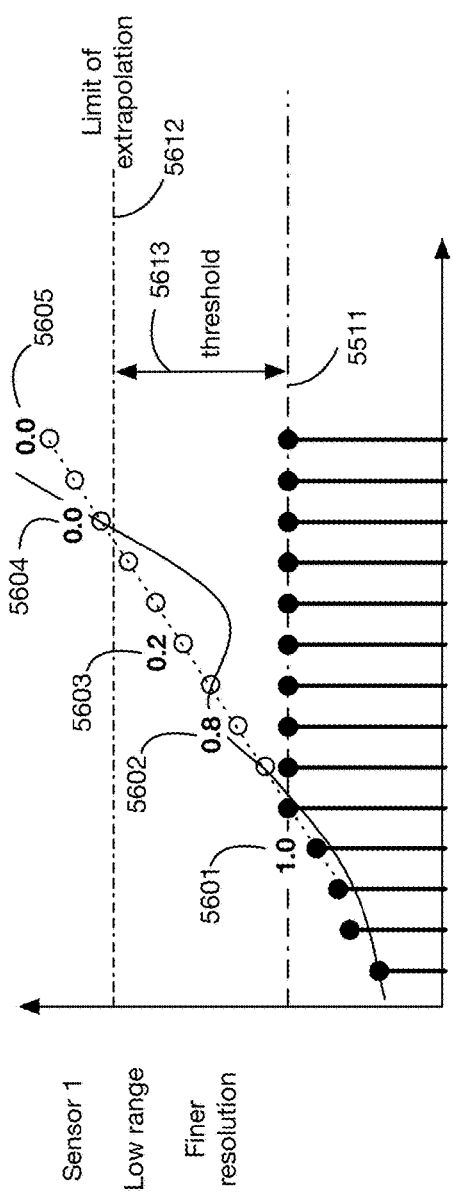
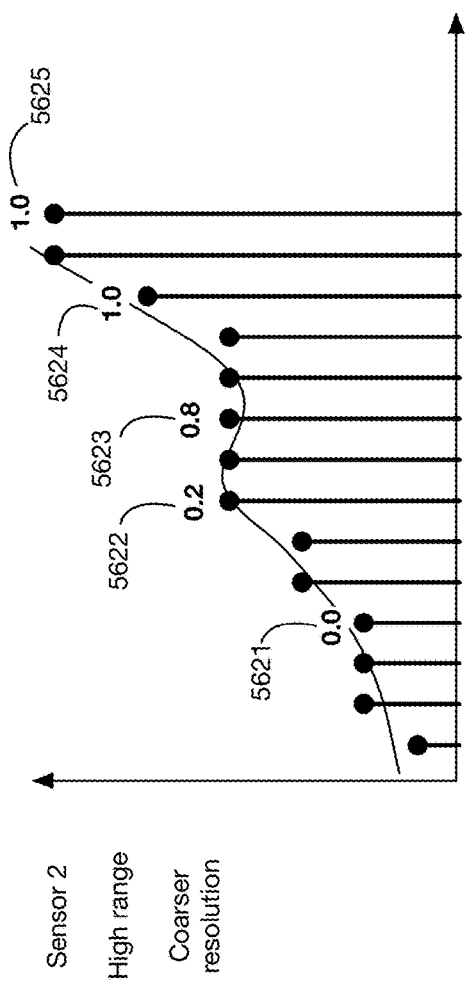
FIG. 56

MOTION CAPTURE SYSTEM THAT COMBINES SENSORS WITH DIFFERENT MEASUREMENT RANGES

This application is a continuation of U.S. Utility patent application Ser. No. 15/490,689, filed on 18 Apr. 2017, issued as U.S. Pat. No. 9,824,264, which is a continuation of U.S. Utility patent application Ser. No. 15/268,501, filed on 16 Sep. 2016, issued as U.S. Pat. No. 9,626,554, which is a continuation-in-part of U.S. Utility patent application Ser. No. 15/006,065, filed on 25 Jan. 2016, issued as U.S. Pat. No. 9,633,254, which is a continuation of U.S. Utility patent application Ser. No. 13/744,384, filed on 17 Jan. 2013, issued as U.S. Pat. No. 9,247,212, which is a continuation-in-part of four patent applications, namely U.S. Utility patent application Ser. No. 13/358,522 filed on 26 Jan. 2012 and issued as U.S. Pat. No. 8,613,676, and U.S. Utility patent application Ser. No. 13/351,429 filed on 17 Jan. 2012 and issued as U.S. Pat. No. 8,903,521, and U.S. Utility patent application Ser. No. 13/306,869 filed on 29 Nov. 2011 and issued as U.S. Pat. No. 9,028,337, and U.S. Utility patent application Ser. No. 13/298,158 filed on 16 Nov. 2011 and issued as U.S. Pat. No. 8,905,855, which is a continuation-in-part of U.S.

Utility patent application Ser. No. 13/267,784 filed on 6 Oct. 2011 and issued as U.S. Pat. No. 9,604,142, which is a continuation-in-part of U.S. Utility patent application Ser. No. 13/219,525 filed on 26 Aug. 2011, issued as U.S. Pat. No. 8,941,723, which is a continuation-in-part of U.S. Utility patent application Ser. No. 13/191,309 filed on 26 Jul. 2011, issued as U.S. Pat. No. 9,033,810, which is a continuation-in-part of U.S. Utility patent application Ser. No. 13/048,850 filed on 15 Mar. 2011, issued as U.S. Pat. No. 8,465,376, which is a continuation-in-part of U.S. Utility patent application Ser. No. 12/901,806 filed on 11 Oct. 2010, issued as U.S. Pat. No. 9,320,957, which is a continuation-in-part of U.S. Utility patent application Ser. No. 12/868,882 filed on 26 Aug. 2010, issued as U.S. Pat. No. 8,994,826, the specifications of which are all hereby incorporated herein by reference.

BACKGROUND OF THE INVENTION

Field of the Invention

One or more embodiments setting forth the ideas described throughout this disclosure pertain to the field of motion capture sensors that produce motion capture data, and displaying information based on motion analysis data associated with a user or piece of equipment or clothing based on previous motion analysis data from the user or other user(s) and/or piece of equipment or clothing. More particularly, but not by way of limitation, one or more aspects of the disclosure enable a wireless or closely coupled intelligent motion capture sensor in a variety of physical formats including standalone and SIM for example that obtains any combination of orientation, position, velocity, acceleration, proximity, pressure or strain and that enables use of the actual motion capture data obtained from portable wireless motion capture elements such as visual markers and sensors, radio frequency identification tags and mobile device computer systems for healthcare compliance, sporting, gaming, military, virtual reality, industrial, retail loss tracking, security, baby and elderly monitoring and other applications and in one or more embodiment includes sensor personalities that optimize the sensor for specific movements and/or pieces of equipment and/or clothing. Embodiments enable highly sophisticated calibration, power saving, dynamic sampling rates or modes, combining data from multiple sensors that measure the same physical quantity, intermittent data transfer for power saving and robustness, interpolation, pairing and displays including remote displays on a mobile device or other computer, or via a local physical display.

Description of the Related Art

Known motion capture sensors are limited for a variety of reasons. One main limitation of known motion capture sensors is accuracy, another limitation is power usage. In addition, known sensors have limited functionality directed at motion and also have limited communications capabilities. Know sensors are specific to a sport or piece of equipment and are incapable of being utilized in multiple pieces of equipment by decoupling and recoupling with a second piece of equipment for example. There are no known helmet based accelerometers that are retrofittable into an existing helmet for example with or without local LED displays to indicate potential concussion level acceleration. Existing systems are known that utilize motion capture sensors to perform remote vital sign monitoring for example, but not based on motion and not based on previously stored motion data from the user or other users or piece of equipment. For example, baby monitoring would be improved significantly if the pattern of the previous motion for chest movement or breathing of the baby were compared to current motion. This allows for display of warnings that a baby's breathing is slower on a particular night than usual, which may indicate that the baby is becoming ill. This would also enable remote sleep apnea monitoring as well. For children that play video games, there are no known systems that compare motion of the game controller to previous motion of the child to determine if the child has been playing video games too much, or in comparison to other children that the child is playing an above average amount. There are no known systems that enable a display to be sent to a monitoring parent or physician based on anything other than current vital signs. The physician could also receive a display of any type of message that indicates if a child or adult is moving a certain amount or not at all or a certain amount in comparison to their usual motion during exercise. This would facilitate diabetes compliance monitoring to ensure the patient is moving enough per day and compared to their previous patterns or other patient patterns with similar demographics for example, and may save the doctor from paying higher insurance premiums if the doctor were able to remotely ensure that each patient is complying with orders. In addition, other types of motion capture include a technique to teach effective body mechanics utilizes video recording of an athlete and analysis of the recorded video of an athlete. This technique has various limitations including inaccurate and inconsistent subjective analysis based on video for example. Another technique includes motion analysis, for example using at least two cameras to capture three-dimensional points of movement associated with an athlete. Known implementations utilize a stationary multi-camera system that is not portable and thus cannot be utilized outside of the environment where the system is installed, for example during an athletic event such as a golf tournament. These fixed installations are extremely expensive as well. Such prior techniques are summarized in U.S. Pat. No. 7,264,554, filed 26 Jan. 2006, which claims the benefit of U.S. Provisional Patent Application Ser. No. 60/647,751 filed 26 Jan. 2005, the specifications of which are both hereby incorporated herein by reference. Both disclosures are to the same inventor of the subject matter of the instant application. Regardless of the motion capture data obtained, the data is generally analyzed on a per user or per swing basis that does not contemplate processing on a mobile phone, so that a user would only buy a motion capture sensor and an "app" for a pre-existing mobile phone. In addition, existing solutions do not contemplate mobile use, analysis and messaging and/or comparison to or use of previously stored motion capture data from the user or other users or data mining of large data sets of motion capture data. To summarize, motion capture data is generally used for immediate monitoring or sports performance feedback and generally has had limited and/or primitive use in other fields.

Known systems generally utilize several passive or active markers or several sensors. There are no known systems that utilize as little as one visual marker or sensor and an app that for example executes on a mobile device that a user already owns, to analyze and display motion capture data associated with a user and/or piece of equipment. The data is generally analyzed in a laboratory on a per user or per swing basis and is not used for any other purpose besides motion analysis or representation of motion of that particular user and is generally not subjected to data mining.

There are no known systems that allow for a group of mobile devices to share data to form three-dimensional motion capture data by triangulation of visual markers. There are no known systems that allow for a mobile device without a camera to obtain images from cameras or other mobile devices with cameras to display motion capture data. In addition, known systems do not save images of users along with motion capture data for later use, including gaming, morphological comparing, compliance, tracking calories burned, work performed, monitoring of children or elderly based on motion or previous motion patterns that vary during the day and night, safety monitoring for troops when G-forces exceed a threshold or motion stops, local use of running, jumping throwing motion capture data for example on a cell phone including virtual reality applications that make use of the user's current and/or previous data or data from other users, or play music or select a play list based on the type of motion a user is performing or data mining.

There are no known mobile motion captures systems that allow for a user to align a camera correctly along the horizontal before capture of motion data having horizontally aligned images.

There are no known systems that allow for motion capture elements such as wireless sensors to seamlessly integrate or otherwise couple with a user or shoes, gloves, shirts, pants, belts, or other equipment, such as a baseball bat, tennis racquet or golf club for local analysis or later analysis in such a small format that the user is not aware that the sensors are located in or on these items. There are no known systems that provide seamless mounts, for example in the weight port of a golf club or at the end shaft near the handle so as to provide a wireless golf club, configured to capture motion data. Data derived from existing sensors is not saved in a database for a large number of events and is not used relative to anything but the performance at which the motion capture data was acquired.

In addition, for sports that utilize a piece of equipment and a ball, there are no known portable systems that allow the user to obtain immediate visual feedback regarding ball flight distance, swing speed, swing efficiency of the piece of equipment or how centered an impact of the ball is, i.e., where on piece of equipment the collision of the ball has taken place. These systems do not allow for users to play games with the motion capture data acquired from other users, or historical players, or from their own previous performances. Known systems do not allow for data mining motion capture data from a large number of swings to suggest or allow the searching for better or optimal equipment to match a user's motion capture data and do not enable original equipment manufacturers (OEMs) to make business decisions, e.g., improve their products, compare their products to other manufacturers, up-sell products or contact users that may purchase different or more profitable products.

In addition, there are no known systems that utilize motion capture data mining for equipment fitting and subsequent point-of-sale decision making for instantaneous purchasing of equipment that fits an athlete. Furthermore, no known systems allow for custom order fulfillment such as assemble-to-order (ATO) for custom order fulfillment of sporting equipment, for example equipment that is built to customer specifications based on motion capture data mining, and shipped to the customer to complete the point of sales process.

In addition, there are no known systems that use a mobile device and RFID tags for passive compliance and monitoring applications. For example, known systems for counting golf shots are cumbersome and require electronics on each golf club and/or switches that a user is required to operate. In addition, known devices also require active electronics, and therefore batteries in each golf club to operate. There are no known systems that allow a golfer to easily record a shot and location of a shot automatically and/or prompt a user to remember to record each shot for a particular club without a battery and active electronics on the club, for example that is not a practice shot. Known systems do not save the shots per user per course over time in a database and do not contemplate data mining the motion capture data, or shot count and distance data for example to allow for OEMs to purchase access to the database for business decision making for example.

There are no known systems that enable data mining for a large number of users related to their motion or motion of associated equipment to find patterns in the data that allows for business strategies to be determined based on heretofore undiscovered patterns related to motion. There are no known systems that enable obtain payment from OEMs, medical professionals, gaming companies or other end users to allow data mining of motion data. For at least the limitations described above there is a need for a system and method for utilizing motion capture data.

There are no known sensors that reside in a variety of formats and which may make use of a single "app" on a mobile phone for example to obtain motion data from multiple different pieces of equipment or clothing for a particular user.

Known system generally use a single sensor to measure a corresponding physical quantity, such as acceleration or angular velocity. Use of a single sensor for each quantity typically requires trading off sensor range for sensor resolution: very precise sensors generally have limited measurement ranges, and conversely sensors with wide measurement ranges typically have limited precision. There are no known systems that combine multiple sensors for a single physical quantity to achieve the benefits of both wide range and high precision.

BRIEF SUMMARY OF THE INVENTION

Embodiments of the invention enable a motion capture sensor configured to capture any combination of values associated with an orientation, position, velocity, acceleration, proximity, pressure or strain that produces motion capture data based on a sensor personality selected from a plurality of sensor personalities, wherein the sensor personality is configured to control sensor settings to collect the data in an optimal manner with respect to a specific type of movement associated with a specific piece of equipment or type of clothing. Embodiments of the invention are more accurate and power efficient than known devices and provide variations of communications capabilities for local or remote communication. Embodiments provide increased capabilities with optional proximity sensors and may be utilized in conjunction with external devices to provide alarm clock capabilities and other functionality. Embodiments of the invention may be utilized by a user that optionally purchases an application or "app" and purchases a motion capture element. Embodiments may be immediately utilizes with an existing computer or mobile computer, e.g., mobile phone. Embodiments of the invention enable applications in healthcare compliance, sporting, gaming, military, fire, police, virtual reality, industrial, retail loss tracking, security, baby and elderly monitoring and other applications through use of motion capture data obtained from one or more users instrumented pieces of sporting equipment. Embodiments of the invention may produce motion capture data that enables the display of motion information to a monitoring user, or user associated with the motion capture sensor (or motion capture element), or piece of equipment. Embodiments may also display information based on motion analysis data associated with a user or piece of equipment based on (via a function including comparison) previously stored motion capture data or motion analysis data associated with the user or piece of equipment or previously stored motion capture data or motion analysis data associated with at least one other user. This enables sophisticated monitoring, compliance, interaction with actual motion capture data or pattern obtained from other user(s), for example to play a virtual game using real motion data obtained from the user with responses generated based thereon using real motion data capture from the user previously or from other users (or equipment). This capability provides for playing against historical players, for example a game of virtual tennis, or playing against an "average" professional sports person, and is unknown in the art until now.

Embodiments of the invention may be utilized by data mining on the motion capture data to obtain patterns for users, equipment, or use the motion capture data of a given user or other user. Data mining relates to discovering new patterns in large databases wherein the patterns are previously unknown. Many methods may be applied to the data to discover new patterns including statistical analysis, neural networks and artificial intelligence for example. Due to the large amount of data, automated data mining may be performed by one or more computers to find unknown patterns in the data. Unknown patterns may include groups of related data, anomalies in the data, dependencies between elements of the data, classifications and functions that model the data with minimal error or any other type of unknown pattern. Displays of data mining results may include displays that summarize newly discovered patterns in a way that is easier for a user to understand than large amounts of pure raw data. One of the results of the data mining process is improved market research reports, product improvement, lead generation and targeted sales. Generally, any type of data that will be subjected to data mining must be cleansed, data mined and the results of which are generally validated. Businesses may increase profits using data mining. Examples of benefits of embodiments of the invention include customer relationship management to highly target individuals based on patterns discovered in the data. In addition, market basket analysis data mining enables identifying products that are purchased or owned by the same individuals and which can be utilized to offer products to users that own one product but who do not own another product that is typically owned by other users. Other areas of data mining include analyzing large sets of motion data from different users to suggest exercises to improve performance based on performance data from other users. For example if one user has less rotation of the hips during a swing versus the average user, then exercises to improve flexibility or strength may be suggested by the system. In a golf course embodiment, golf course planners may determine over a large amount of users on a golf course which holes should be adjusted in length or difficulty to obtain more discrete values for the average number of shots per hole, or for determining the amount of time between golfers, for example at a certain time of day or for golfers of a certain age. In addition, sports and medical applications of data mining include determining morphological changes in user performance over time, for example versus diet or exercise changes to determine what improves performance the most. Use of motion capture data for a particular user or with respect to other users enables healthcare compliance, for example to ensure a person with diabetes moves a certain amount during the day, and morphological analysis to determine how a user's motion or range of motion has changed over time. Games may be played with motion capture data that enables virtual reality play against historical greats or other users. For example, a person may play against a previous performance of the same person or against the motion capture data of a friend. This allows users to play a game in a historic stadium or venue in a virtual reality environment, but with motion capture data acquired from the user or other users previously for example. Displays that are color coded or show portions of motion that differ from the user's previous motion, or an average of the user's previous motion or the "best" motion from the user's previous motion may be shown on any computer coupled with embodiments of the invention. Military planners may utilize the motion capture data to determine which soldiers are most fit and therefore eligible for special operations, or which ones should retire. Embodiments of the motion capture sensors may be utilized in retail loss applications by wirelessly alerting a server when an item associated with the motion capture sensor has moved to a location outside of a store and may for example wirelessly transmit the location, speed, direction, etc., of the item to law enforcement. Embodiments of the invention may also be utilized for baby and elderly monitors to determine when motion occurs or stops, wherein embodiments of the invention may alert a third party based on the motion or lack thereof.

Embodiments of the invention may be utilized with a system to perform motion capture and/or display with an application for example that optionally executes on mobile device that may include a visual display and an optional camera. Embodiments of the system are configured to obtain motion capture data from at least one motion capture sensor or element such as a visual marker and/or a wireless sensor. The system can also integrate with standalone cameras, or cameras on multiple mobile devices. The system also enables the user to analyze and display the motion capture data in a variety of ways that provide immediate easy to understand graphical information associated with the motion capture data. Motion capture elements utilized in the system intelligently store data for example related to events associated with striking a ball, making a ski turn, jumping, etc., and eliminate false events, and greatly improve memory usage and minimize storage requirements. In addition, the data may be stored for example for more than one event associated with the sporting equipment, for example multiple bat swings or for an entire round of golf or more if necessary at least until the data is downloaded to a mobile device or to the Internet. Data compression of captured data may also be utilized to store more motion capture data in a given amount of memory. Motion capture elements utilized in the system may also be configured to intelligently power down portions of their circuitry to save power, for example power down transceivers until motion is detected of a certain type. Embodiments of the invention may also utilize flexible battery connectors to couple two or more batteries in parallel to increase the time the system may be utilized before replacing the batteries. Motion capture data is generally stored in memory such as a local database or in a network accessible database, any of which enables data mining described above. Any other type of data mining may be performed using embodiments of the invention, including searching for temporal changes of data related to one or more users and or simply searching for data related to a particular user or piece of equipment. Embodiments of the invention may also utilize BLUETOOTH® Low Energy Profiles that further conserve power. In addition, embodiments of the invention may intelligently calculate gravity vectors for orientation at one or more points in time to increase accuracy and change sampling rates as a function of time or acceleration to further increase accuracy over a G-force range. Proximity sensors in one or more embodiments of the invention or coupled with a mobile computer may be utilized to determine whether a piece of sporting equipment has been accidentally left behind or is the piece of equipment being utilized, or may be utilized for shot tracking for certain types of equipment in certain sports. Proximity sensors for example may be combined on an ASIC with embodiments of the motion capture sensor to provide increased capabilities. In addition, a BLE radio may be combined on an ASIC with the motion capture sensor to provide a single chip solution for motion capture. One or more embodiments of the invention may communicate with a mobile computer that is local using local communications protocols or may communicate distally using longer range communications protocols as desired and based on available energy. Embodiments of the invention may be utilized to provide an alarm clock, for example by utilizing motion capture data associated with a mobile computer, wherein the alarm stops when the mobile computer is moved by a user.

Embodiments of the invention may calibrate more than one sensor at a time, either while mounted on a piece of equipment or in a hexapod so that for example a large number of motion capture elements may be calibrated by moving one piece of equipment coupled to the motion capture elements that in turn moves the motion capture elements in the number of desired axes.

Other embodiments may display information such as music selections or music playlists to be played based on the motion related data. This for example enables a performance to be compared to another user's performance and select the type of music the other user plays, or to compare the performance relative to a threshold that determines what type of music selection to suggest or display.

Embodiments of the invention directed at sports for example may couple with RFID tags or passive RFID tags directly or indirectly that are placed on items that a user moves wherein embodiments of the system keep track of the motion. For example, by placing passive RFID tags on particular dumbbells at a gym, and by wearing motion capture elements such as gloves and with a pre-existing mobile device for example an IPHONE®, embodiments of the invention provide automatic fitness and/or healthcare compliance. This is achieved by keeping track of the motion, and via RIFD or passive RFID, the weight that the user is lifting. Proximity detection via power associated with a particular RFID tag or using a proximity detector coupled with the RFID tag or motion sensor may be utilized alone or in combination to better detect the equipment that a user is using. Embodiments of the system may thus add the number of repetitions multiplied by the amount of weight indicated by each RFID tag to calculate the number of calories burned by the user. In another example, an RFID tag coupled with a stationary bike, or wherein the stationary bike can mimic the identifier and/or communicate wirelessly to provide performance data and wherein the mobile computer includes an RFID reader, the number of rotations of the user's legs may be counted. Any other use of RFID or passive RFID is in keeping with the spirit of the invention. This enables doctors to remotely determine whether a user has complied with their medical recommendations. Embodiments may thus be utilized by users to ensure compliance and by doctors to lower their malpractice insurance rates since they are ensuring that their patients are complying with their recommendations, albeit remotely. Embodiments of the system do not require RFID tags for medical compliance, but may utilize them. Embodiments of the system directed at golf also enable golf shots for each club associated with a golfer to be counted through use of an identifier such as RFID tags on each club (or optionally via an identifier associated with motion capture electronics on a golf club or obtained remotely over the radio) and a mobile computer, for example an IPHONE® equipped with an RFID reader that concentrates the processing for golf shot counting on the mobile computer instead of on each golf club. Embodiments of the invention may also allow for the measurement of orientation (North/South, and/or two horizontal axes and the vertical axis) and acceleration using an inertial measurement unit, or accelerometers and/or magnetometers, and/or gyroscopes. This is not required for golf shot counting, although one or more embodiments may determine when the golf club has struck a golf ball through vibration analysis for example and then query a golfer whether to count a shot or not. This functionality may be combined with speed or acceleration threshold or range detection for example to determine whether the golf club was travelling within an acceptable speed or range, or acceleration or range for the "hit" to count. Wavelets may also be utilized to compare valid swing signatures to eliminate count shots or eliminate false strikes for example. This range may vary between different clubs, for example a driver speed range may be "greater than 30 mph" while a putter speed range may be "less than 20 mph", any range may be utilized with any club as desired, or the speed range may be ignored for example. Alternatively or in combination, the mobile computer may only query the golfer to count a shot if the golfer is not moving laterally, i.e., in a golf cart or walking, and/or wherein the golfer may have rotated or taken a shot as determined by a orientation or gyroscope sensor coupled with the mobile computer. The position of the stroke may be shown on a map on the mobile computer for example. In addition, GPS receivers with wireless radios may be placed within the tee markers and in the cups to give daily updates of distances and helps with reading putts and greens for example. The golfer may also wear virtual glasses that allow the golfer to see the golf course map, current location, distance to the hole, number of shots on the current hole, total number of shots and any other desired metric. If the user moves a certain distance, as determined by GPS for example, from the shot without counting the shot, the system may prompt the user on whether to count the shot or not. The system does not require a user to initiate a switch on a club to count a shot and does not require LED's or active or battery powered electronics on each club to count shots. The mobile computer may also accept gestures from the user to count a shot or not count a shot so that the golfer does not have to remove any gloves to operate the mobile computer. For embodiments that utilize position/orientation sensors, the system may only count shots when a club is oriented vertically for example when an impact is detected. The apparatus may also include identifiers that enable a specific apparatus to be identified. The identifiers may be a serial number for example. The identifier for example may originate from an RFID tag on each golf club, or optionally may include a serial number or other identifier associated with motion capture elements associated with a golf club. Utilizing this apparatus enables the identification of a specific golfer, specific club and also enables motion capture and/or display with a system that includes a television and/or mobile device having a visual display and an optional camera and capable of obtaining data from at least one motion capture element such as a visual marker and/or a wireless sensor. The system can also integrate with standalone cameras, or cameras on multiple mobile devices. The system also enables the user to analyze and display the motion capture data in a variety of ways that provide immediate and easy to understand graphical information associated with the motion capture data. The apparatus enables the system to also determine how "centered" an impact is with respect to a ball and a piece of equipment, such as a golf club for example. The system also allows for fitting of equipment including shoes, clubs, etc., and immediate purchasing of the equipment even if the equipment requires a custom assemble-to-order request from a vendor. Once the motion capture data, videos or images and shot count indications are obtained by the system, they may be stored locally, for example in a local database or sent over a telephonic or wireless interface to a remote database for example. Once in a database, the various elements including any data associated with the user, such as age, sex, height, weight, address, income or any other related information may be utilized in embodiments of the invention and/or subjected to data mining. One or more embodiments enable users or OEMs for example to pay for access to the data mining capabilities of the system.

For example, embodiments that utilize motion capture elements allow for analyzing the data obtained from the apparatus and enable the presentation of unique displays associated with the user, such as 3D overlays onto images of the body of the user to visually depict the captured motion data. In addition, these embodiments may also utilize active wireless technology such as BLUETOOTH® Low Energy for a range of up to 50 meters to communicate with a golfer's mobile computer. Embodiments of the invention also allow for display of queries for counting a stroke for example as a result of receiving a golf club ID, for example via an RFID reader or alternatively via wireless communication using BLUETOOTH® or IEEE 802.11 for example. Use of BLUETOOTH® Low Energy chips allows for a club to be in sleep mode for up to 3 years with a standard coin cell battery, thus reducing required maintenance. One or more embodiments of the invention may utilize more than one radio, of more than one technology for example. This allows for a level of redundancy that increases robustness of the system. For example, if one radio no longer functions, e.g., the BLUETOOTH® radio for example, then the IEEE 802.11 radio may be utilized to transfer data and warn the golfer that one of the radios is not functioning, while still allowing the golfer to record motion data and count shots associated with the particular club. For embodiments of the invention that utilize a mobile device (or more than one mobile device) without camera(s), sensor data may be utilized to generate displays of the captured motion data, while the mobile device may optionally obtain images from other cameras or other mobile devices with cameras. For example, display types that may or may not utilize images of the user may include ratings, calculated data and time line data. Ratings associated with the captured motion can also be displayed to the user in the form of numerical or graphical data with or without a user image, for example an "efficiency" rating. Calculated data, such as a predicted ball flight path data can be calculated and displayed on the mobile device with or without utilizing images of the user's body. Data depicted on a time line can also be displayed with or without images of the user to show the relative peaks of velocity for various parts of the equipment or user's body for example. Images from multiple cameras including multiple mobile devices, for example from a crowd of golf fans, may be combined into a BULLET TIME® visual effect characterized by slow motion of the golf swing shown from around the golfer at various angles at normal speed. All analyzed data may be displayed locally, or uploaded to the database along with the motion capture data, images/videos, shot count and location data where it may undergo data mining processes, wherein the system may charge a fee for access to the results for example.

Motion capture data can be displayed in many ways, for example tweeted, to a social network during or after motion capture. For example, if a certain amount of exercise or motion is performed, or calories performed, or a new sports power factor maximum has been obtained, the system can automatically tweet the new information to a social network site so that anyone connected to the Internet may be notified. The data uploaded to the Internet, i.e., a remote database or remote server or memory remote to the system may be viewed, analyzed or data mined by any computer that may obtain access to the data. This allows for remote compliance tweeting and/or compliance and/or original equipment manufacturers to determine for a given user what equipment for compliance or sporting equipment for sports related embodiments is working best and/or what equipment to suggest. Data mining also enables suggestions for users to improve their compliance and/or the planning of sports venues, including golf courses based on the data and/or metadata associated with users, such as age, or any other demographics that may be entered into the system. Remote storage of data also enables medical applications such as morphological analysis, range of motion over time, and diabetes prevention and exercise monitoring and compliance applications as stated. Other applications also allow for games that use real motion capture data from other users, or historical players whether alive or dead after analyzing videos of the historical players for example. Virtual reality and augmented virtual reality applications may also utilize the motion capture data or historical motion data. Military personnel such as commanders and/or doctors may utilize the motion and/or images in determine what type of G-forces a person has undergone from an explosion near an Improvised Explosive Device and automatically route the best type of medical aid automatically to the location of the motion capture sensor. One or more embodiments of the system may relay motion capture data over a G-force or velocity threshold, to their commanding officer or nearest medical personnel for example via a wireless communication link.

In one or more embodiments of the invention, fixed cameras such as at a tennis tournament, football game, baseball game, car or motorcycle race, golf tournament or other sporting event can be utilized with a wireless interface located near the player/equipment having motion capture elements so as to obtain, analyze and display motion capture data. In this embodiment, real-time or near real-time motion data can be displayed on the video for augmented video replays. An increase in the entertainment level is thus created by visually displaying how fast equipment is moving during a shot, for example with rings drawn around a players hips and shoulders. Embodiments of the invention also allow images or videos from other players having mobile devices to be utilized on a mobile device related to another user so that users don't have to switch mobile phones for example. In one embodiment, a video obtained by a first user for a piece of sporting equipment in motion that is not associated with the second user having the video camera equipped mobile phone may automatically transfer the video to the first user for display with motion capture data associated with the first user. Video and images may be uploaded into the database and data mined through image analysis to determine the types/colors of clothing or shoes for example that users are wearing.

Based on the display of data, the user can determine the equipment that fits the best and immediately purchase the equipment, via the mobile device. For example, when deciding between two sets of skis, a user may try out both pairs that are instrumented with motion capture elements wherein the motion capture data is analyzed to determine which pair of skis enables more efficient movement. For golf embodiments, when deciding between two golf clubs, a user can take swings with different clubs and based on the analysis of the captured motion data and quantitatively determine which club performs better. Custom equipment may be ordered through an interface on the mobile device from a vendor that can assemble-to-order customer built equipment and ship the equipment to the user for example. Shaft lengths for putters for example that are a standard length can be custom made for a particular user based on captured motion data as a user putts with an adjustable length shaft for example. Based on data mining of the motion capture data and shot count data and distances for example allows for users having similar swing characteristics to be compared against a current user wherein equipment that delivers longer shots for a given swing velocity for a user of a particular size and age for example may be suggested or searched for by the user to improve performance. OEMs may determine that for given swing speeds, which make and model of club delivers the best overall performance as well. One skilled in the art will recognize that this applies to all activities involving motion, not just golf.

Embodiments of the system may utilize a variety of sensor types. In one or more embodiments of the invention, active sensors may integrate with a system that permits passive or active visual markers to be utilized to capture motion of particular points on a user's body or equipment. This may be performed in a simply two-dimensional manner or in a three-dimensional manner if the mobile device is configured with two or more cameras, or if multiple cameras or mobile devices are utilized to capture images such as video and share the images in order to create triangulated three-dimensional motion data from a set of two-dimensional images obtained from each camera. Another embodiment of the invention may utilize inertial measurement units (IMU) or any other sensors that can produce any combination of orientation, position, velocity and/or acceleration information to the mobile device. The sensors may thus obtain data that may include any combination of one or more values associated with orientation (vertical or North/South or both), position (either via through Global Positioning System, i.e., "GPS" or through triangulation), velocity (in all three axes), acceleration (in all three axes). All motion capture data obtained from the various sensor types may be saved in a database for analysis, monitoring, compliance, game playing or other use and/or data mining, regardless of the sensor type.

In one or more embodiments of the invention, a sensor may be utilized that includes a passive marker or active marker on an outside surface of the sensor, so that the sensor may also be utilized for visual tracking (either two-dimensional or three-dimensional) and for orientation, position, velocity, acceleration or any other physical quantity produced by the sensor. Visual marker embodiments of the motion capture element(s) may be passive or active, meaning that they may either have a visual portion that is visually trackable or may include a light emitting element such as a light emitting diode (LED) that allows for image tracking in low light conditions. This for example may be implemented with a graphical symbol or colored marker at the end of the shaft near the handle or at the opposing end of the golf club at the head of the club. Images or videos of the markers may be analyzed locally or saved in the database and analyzed and then utilized in data mining.

Embodiments of the motion capture sensors may be generally mounted on or near one or more end or opposing ends of sporting equipment, for example such as a golf club and/or anywhere in between (for EI measurements) and may integrate with other sensors coupled to equipment, such as weapons, medical equipment, wristbands, shoes, pants, shirts, gloves, clubs, bats, racquets, balls, etc., and/or may be attached to a user in any possible manner. For example, a rifle to determine where the rifle was pointing when recoil was detected by the motion capture sensor. This data may be transmitted to a central server, for example using a mobile computer such as a mobile phone or other device and analyzed for war games practice for example. In addition, one or more embodiments of the sensor can fit into a weight port of a golf club, and/or in the handle end of the golf club. Other embodiments may fit into the handle of, or end of, a tennis racquet or baseball bat for example. One or more embodiments of the invention may also operate with balls that have integrated sensors as well. One or more embodiments of the mobile device may include a small mountable computer such as an IPOD® SHUFFLE® or IPOD® NANO® that may or may not have integrated displays, and which are small enough to mount on a shaft of a piece of sporting equipment and not affect a user's swing. Alternatively, the system may calculate the virtual flight path of a ball that has come in contact with equipment moved by a player. For example with a baseball bat or tennis racquet or golf club having a sensor integrated into a weight port of other portion of the end of the club striking the golf ball and having a second sensor located in the tip of the handle of the golf club, or in one or more gloves worn by the player, an angle of impact can be calculated for the club. By knowing the loft of the face of the club, an angle of flight may be calculated for the golf ball. In addition, by sampling the sensor at the end of the club at a high enough speed to determine oscillations indicative of where on the face of the club the golf ball was struck, a quality of impact may be determined. These types of measurements and the analysis thereof help an athlete improve, and for fitting purposes, allow an athlete to immediately purchase equipment that fits correctly. Centering data may be uploaded to the database and data mined for patterns related to the bats, racquets or clubs with the best centering on average, or the lowest torsion values for example on a manufacturer basis for product improvement. Any other unknown patterns in the data that are discovered may also be presented or suggested to users or search on by users, or paid for, for example by manufacturers or users.

One or more embodiments of the sensor may contain charging features such as mechanical eccentric weight, as utilized in some watches known as "automatic" or "self-winding" watches, optionally including a small generator, or inductive charging coils for indirect electromechanical charging of the sensor power supply. Other embodiments may utilize plugs for direct charging of the sensor power supply or electromechanical or microelectromechanical (MEMS) based charging elements. Any other type of power micro-harvesting technologies may be utilized in one or more embodiments of the invention. One or more embodiments of the sensor may utilize power saving features including gestures that power the sensor on or off. Such gestures may include motion, physical switches, contact with the sensor, wireless commands to the sensor, for example from a mobile device that is associated with the particular sensors. Other elements that may couple with the sensor includes a battery, low power microcontroller, antenna and radio, heat sync, recharger and overcharge sensor for example. In addition, embodiments of the invention allow for power down of some or all of the components of the system until an electronic signal from accelerometers or a mechanical switch determines that the club has moved for example.

One or more embodiments of the invention enable Elasticity Inertia or EI measurement of sporting equipment and even body parts for example. Placement of embodiments of the sensor along the shaft of a golf club, tennis racquet, baseball bat, hockey stick, shoe, human arm or any other item that is not perfectly stiff enables measurement of the amount of flex at points where sensors are located or between sensors. The angular differences in the each sensor over time allow for not only calculation of a flex profile, but also a flex profile that is dependent on time or force. For example, known EI machines use static weights between to support points to determine an EI profile. These machines therefore cannot detect whether the EI profile is dependent upon the force applied or is dependent on the time at which the force is applied, for example EI profiles may be non-linear with respect to force or time. Example materials that are known to have different physical properties with respect to time include Maxwell materials and non-Newtonian fluids.

A user may also view the captured motion data in a graphical form on the display of the mobile device or for example on a set of glasses that contains a video display. The captured motion data obtained from embodiments of the motion capture element may also be utilized to augment a virtual reality display of user in a virtual environment. Virtual reality or augmented reality views of patterns that are found in the database via data mining are also in keeping with the spirit of the invention.

One or more embodiments utilize a motion capture element that includes a memory, a sensor configured to capture any combination of values associated with an orientation, position, velocity, acceleration, proximity, pressure or strain, an optional radio and a microcontroller coupled with the memory, the sensor and optionally with the optional radio. In one or more embodiments the microcontroller is configured to collect data that includes sensor values from said sensor based on a sensor personality selected from a plurality of sensor personalities, wherein the sensor personality is configured to control sensor settings to collect the data in an optimal manner with respect to a specific type of movement associated with a specific piece of equipment or type of clothing, store the data in memory and transmit the data via said radio or transmit the data over a direct connection to an attached mobile device for example. In one or more embodiments, the motion capture element is configured to decouple from a first mount on a first piece of equipment or clothing and couple with a second mount on a different type of second piece of equipment or clothing and automatically utilize a different sensor personality associated with said second piece of equipment or clothing.

In one or more embodiments, the motion capture element is configured to couple with a piece of sporting equipment having an integrated mount or wherein the motion capture element is configured to couple with a mount that is removable from the piece of sporting equipment. In one or more embodiments, the motion capture element is configured to reside within a SIM card. In other embodiments, the sensor may reside in an integrated format for example with a power source such as a battery. Embodiments may include a motion capture element configured to transmit the data to a mobile device that comprises an application configured to blend at least two trajectories in the data to form a more accurate single trajectory. Other embodiments of the apparatus may be configured to output a motion gesture or circle gesture or number of taps gesture to enable the motion capture element to signify that particular motion capture element that is to be communicated with instead of one or more other motion capture elements within the vicinity of the mobile device. This enables easy pairing of devices in multiple device environments. One or more embodiments may include a motion capture element that further includes an output display for local viewing of motion capture data. This enables local display of acceleration or other motion related parameters without a mobile device and may be utilized within a helmet based mounting scenario so that potential concussions may be displayed locally without requiring any cell phones with apps for example.

Embodiments of the microcontroller may be further configured to recalibrate the sensor through measurement of changes in linear acceleration during a motionless period for the sensor, computation of an average of the linear acceleration along each axis, computation of an average magnitude of the linear acceleration $g_m$, comparison of $g_m$ to g wherein g is 9.8 m/sec², calculation of a scaling factor $s=g/g_m$ and multiplication of a calibration matrix by the scaling factor if a difference between g and $g_m$ exceeds a predefined threshold. Other embodiments of the microcontroller may perform calibration or recalibration through measurement of linear acceleration during a low acceleration time window for at least two axes of the sensor, comparison of differences in linear acceleration in the low acceleration time window and performance of a recalibration using calibration data from a below threshold sensor or transmission of an out of calibration alert.

One or more embodiments of the system may use multiple sensors to measure the same physical quantity; these sensors may have different measurement ranges. For example, one or more embodiments may use multiple sensors to measure a physical quantity such as position, orientation, velocity, acceleration, angular velocity, angular acceleration, or to measure any function of these values. Sensors may be integrated into a motion capture element that collects data and transmits it to a computer for analysis. The receiving computer may combine the sensor data from the multiple sensors to form a combined estimate of the measured physical quantity. Motion analysis may use the combined estimates of each of the physical quantities measured by the motion capture element.

For example, one or more embodiments may incorporate a motion capture element that has a gyroscope to measure angular velocity, and that has two (or more) accelerometers to measure linear acceleration. This configuration is illustrative; one or more embodiments may use multiple sensors for any or all quantities of interest. The two accelerometers may have different measurement ranges; for example, one accelerometer may have an upper measurable value of 16 g or 24 g, and the other may be a high-range accelerometer with an upper measurable value of 100 g or 400 g.

Embodiments may combine individual sensor data or estimates of individual sensor values in any desired manner. For example, one or more embodiments may use one of the sensor's values as the combined estimate when the other sensor or sensors are at the limits of their measurement range (suggesting that the true value may be beyond the range of the other sensor or sensors). If multiple sensors report values that are in the interior of the associated measurement ranges, one or more embodiments may select the value associated with the sensor that has finer measurement resolution. While this approach is simple, it potentially ignores information from other sensors. Therefore, one or more embodiments may combine sensor data using a weighted average, for example with weights that are inversely proportional to the measurement variance of each sensor. Measurement variance may be measured, or one or more embodiments may estimate the measurement variance by assuming that it is proportional to the square of the measurement resolution.

With multiple sensors measuring the same physical quantity, one or more embodiments may compare data across the multiple sensors to detect when one or more of the sensors is out of calibration. For example, one or more embodiments may perform a paired t-test on sensor samples from two sensors that measure the same quantity; when the t-test indicates statistically significant differences, the system may generate an out of calibration signal to indicate that users or the system should recalibrate the sensors.

One or more embodiments may extrapolate sensor data beyond the measurement range of the sensor, for example using linear or polynomial curves that are fit to sensor samples before or after the sensor hits its measurement endpoints. The extrapolated data may then be combined with potentially coarser resolution sensor data from a higher range sensor, to form a combined estimate of a physical quantity. In one or more embodiments the combination may be a weighted average of the extrapolated values from one sensor with the raw sensor data from another sensor. The weights for example may be set to decrease the weight of the extrapolated values as they deviate further from the sensor's measurement range, potentially decreasing to zero weight when the extrapolated values exceed a threshold beyond the measurement limits of the sensor.

BRIEF DESCRIPTION OF THE DRAWINGS

FIG. 1 illustrates an embodiment of the system that enables a system and method for utilizing motion capture data.

FIG. 1A illustrates a logical hardware block diagram of an embodiment of the computer.

FIG. 1B illustrates an architectural view of an embodiment of the database utilized in embodiments of the system.

FIG. 2 illustrates an embodiment of the overall modes of the software programmed to execute on the computer of the mobile device, wherein the computer is configured to recognize the motion capture elements, obtain data, analyze the data and display motion analysis data.

FIG. 10 illustrates an embodiment of the motion capture element implemented with a passive marker and gray scale images thereof to show how the marker can be tracked by obtaining an image and searching for a luminance change from black to white.

FIG. 11 illustrates a hardware implementation of the sensor portion of a motion capture element implemented as a wireless inertial measurement unit, and an embodiment as configured to couple with a weight port of a golf club for example.

FIG. 29A illustrates a display of a user showing a portions of the swing that are color coded in relation to another swing from that user or another user to show relative speed differences at different locations of the swing.

FIG. 29B illustrates a display of the user of FIG. 29A wherein the swing is shown in spatial relation to another swing, or average of swings or "best" swing of that user or another user.

FIG. 37 illustrates one embodiment of the equations used for predicting a golf ball flight path as used to produce displays as shown in FIGS. 27 and 28.

FIG. 41C illustrates a helmet based mount, that enables coupling to a helmet or otherwise retrofit the helmet for determining acceleration of the helmet and/or head for concussion determination applications for example.

FIG. 49A-B illustrate two trajectories in the motion capture data that may be interpolated or otherwise averaged to create a more accurate or smoother trajectory for example or to otherwise smooth the trajectory for any other purpose.

FIG. 50 shows a motion capture system with two accelerometers that have different measurement ranges; a computer receives data from both accelerometers and combines them into an integrated estimate of acceleration.

FIG. 56 shows illustrative weights for combining the extrapolated measurements and the higher range sensor measurements from FIG. 55; the weights for the extrapolated values decrease as they deviate further from the measurable range of the low-range sensor.

DETAILED DESCRIPTION OF THE INVENTION

Figure 1C:
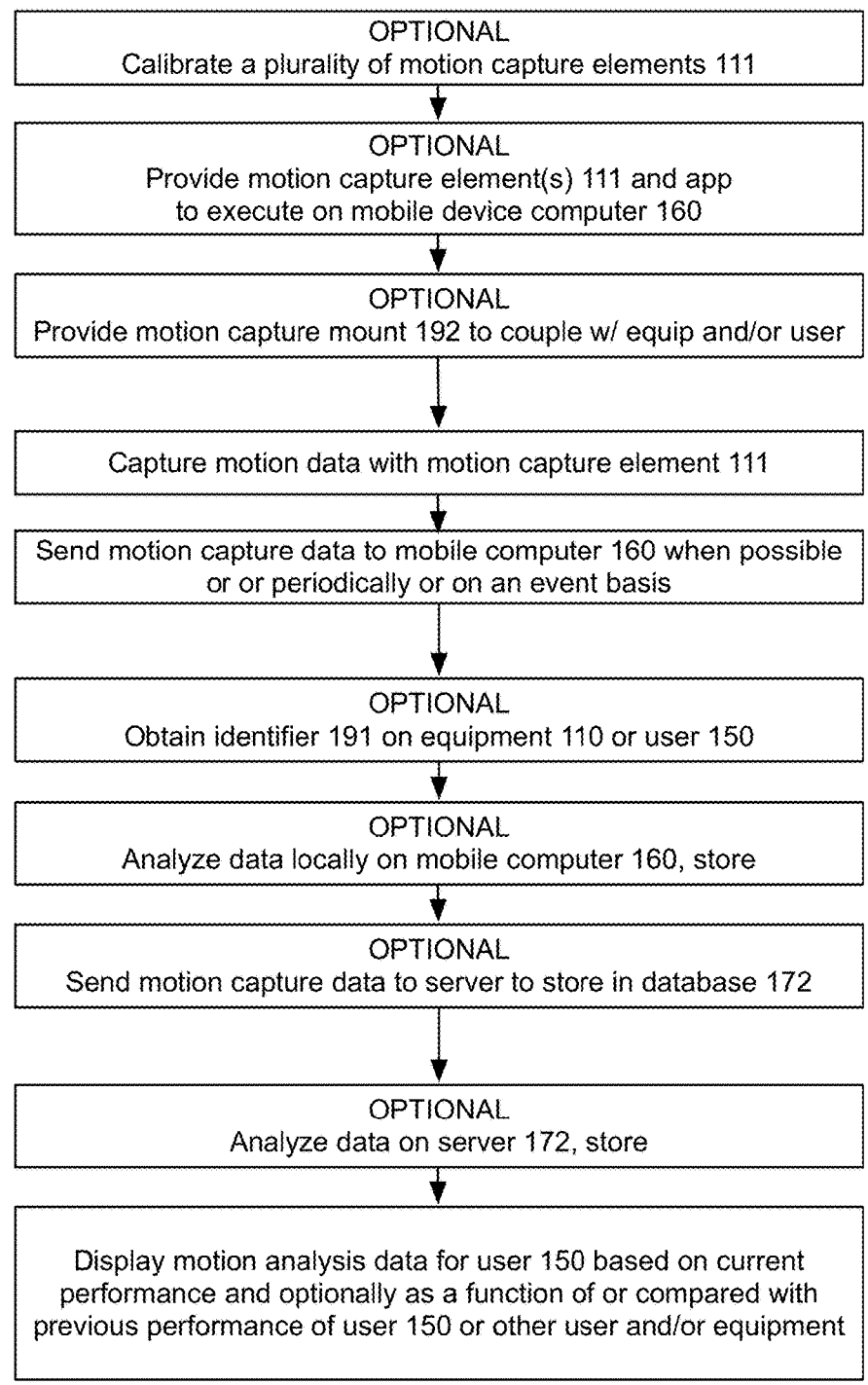
FIG. 1C illustrates a flow chart for an embodiment of the processing performed by embodiments of the computers in the system as shown in FIGS. 1 and 1A.

A motion capture system that combines sensors with different measurement ranges will now be described. In the following exemplary description numerous specific details are set forth in order to provide a more thorough understanding of the ideas described throughout this specification. It will be apparent, however, to an artisan of ordinary skill that embodiments of ideas described herein may be practiced without incorporating all aspects of the specific details described herein. In other instances, specific aspects well known to those of ordinary skill in the art have not been described in detail so as not to obscure the disclosure. Readers should note that although examples of the innovative concepts are set forth throughout this disclosure, the claims, and the full scope of any equivalents, are what define the invention.

FIG. 1 illustrates an embodiment of the invention, namely motion capture element 111 that produces motion capture data that may be analyzed, displayed and otherwise utilized by system that enables a system and method for utilizing motion capture data 100. The system generally includes at least one motion capture element 111 that couples with user 150 or with piece of equipment 110, via mount 192, for example to a golf club, or baseball bat, tennis racquet, hockey stick, weapon, stick, sword, or any other piece of equipment for any sport, or other sporting equipment such as a shoe, belt, gloves, glasses, hat, or any other item. The at least one motion capture element 111 may be placed at one end, both ends, or anywhere between both ends of piece of equipment 110 or anywhere on user 150 and may for example be utilized for EI measurements of any item. Other embodiments may mount in a SIM card slot of any type of device for SIM embodiment implementations, or retrofit existing equipment such as a helmet or other piece of equipment or clothing. One or more embodiments may mount in different types of equipment or clothing by removing the sensor from one and inserting the sensor in any other type of equipment or clothing. Mounts may include integrated mounts, such as built in to a handle or other piece of equipment or couple with the piece of equipment so as to retrofit the existing equipment with motion capture capabilities. This enables a user to instrument or capture data from a variety of items after purchasing a single motion capture sensor. Embodiments of the invention may thus utilize through user selection or automatically utilize a different sensor personality for example based on motion analysis, to optimize the captured motion data associated with a particular type of movement, for example based on a sensor personality selected from a plurality of sensor personalities, wherein the sensor personality is configured to control sensor settings to collect the data in an optimal manner with respect to a specific type of movement associated with a specific piece of equipment or type of clothing. For example, a golf swing and baseball swing have different characteristics, for example level swing versus off-axis planar swing and thus may be detected and analyzed for use of the baseball or golf personality automatically as determined by the microprocessor. The motion capture sensor may also broadcast or otherwise advertise data so that pairing is performed easily in environments with multiple sensors. This enables gestures, circles, taps, etc., to signify a particular sensor that is thus paired for example with a mobile device so that the correct data from the desired piece of equipment is captured. The particular motion may be utilized to alter the personality or data capture automatically, for example to switch from low G to high G sampling or to change the sampling rate near an expected event for example. In addition, the motion capture sensor may include or couple with a display, such as an LED display for example that shows values locally. This may be utilized in helmet or iPod applications that may show the motion capture data proximal to the sensor as opposed to wireless transmission and display of the data on a mobile device. Alternatively, both display methods may be utilized by one sensor in one or more embodiments of the invention. The motion capture element may optionally include a visual marker, either passive or active, and/or may include a wireless sensor, for example any sensor capable of providing any combination of one or more values associated with an orientation (North/South and/or up/down), position, velocity and/or acceleration of the motion capture element. The computer may be configured to obtain data associated with an identifier unique to each piece of equipment 110, e.g., clothing, bat, etc., for example from an RFID coupled with club 110, i.e., identifier 191, and optionally associated with the at least one motion capture element, either visually or wirelessly, analyze the data to form motion analysis data and display the motion analysis data on display 120 of mobile device 101, or alternatively or in combination on mobile computer 105 or on any computer that may access database 172 for example via Internet 171 or network 170 or website 173.

Specifically, one or more embodiments utilize a motion capture element 111 that includes a memory, a sensor configured to capture any combination of values associated with an orientation, position, velocity, acceleration, proximity, pressure or strain, an optional radio and a microcontroller coupled with the memory, the sensor and optionally with the optional radio. In one or more embodiments the microcontroller is configured to collect data that includes sensor values from said sensor based on a sensor personality selected from a plurality of sensor personalities, wherein the sensor personality is configured to control sensor settings to collect the data in an optimal manner with respect to a specific type of movement associated with a specific piece of equipment or type of clothing, store the data in memory and transmit the data via said radio or transmit the data over a direct connection to an attached mobile device for example. For example, a sensor personality may switch a sensor into high rate capture near an expected event, for example based on currently captured motion data. This enables switching of personalities in a dynamic manner. The personalities may be downloaded dynamically or stored local to the sensor for example and switched either based on the motion being captured, or through command by the user, or in any other manner. Personalities may be switched for example to save power, to optimize the captured data for a particular type of sport or equipment or clothing or for any other reason. In one or more embodiments, the personality may be implemented with a "strategy" design pattern for example where the personality is dynamically switched when an event occurs. For example in a baseball scenario, the sensor may be switched into high rate capture if the velocity is over a certain threshold, indicating a real swing and not a swing with a weight on the end of the batter during warm up. Although this example is baseball specific, the personality may be implemented within the motion capture sensor, for example in memory for use by the microcontroller to handle any type of movement or sport for example. This enables processing to be optimized based on the particular motion, which is unknown in the art. In one or more embodiments, the motion capture element is configured to decouple from a first mount on a first piece of equipment or clothing and couple with a second mount on a different type of second piece of equipment or clothing and automatically utilize a different sensor personality associated with said second piece of equipment or clothing.

In one or more embodiments, the motion capture element is configured to couple with a piece of sporting equipment having an integrated mount or wherein the motion capture element is configured to couple with a mount that is removable from the piece of sporting equipment. In one or more embodiments, the motion capture element is configured to reside within a SIM card. In other embodiments, the sensor may reside in an integrated format for example with a power source such as a battery. As shown in FIG. 1, element 190 may also represent a SIM card slot alone or in combination with an RFID reader for example. Embodiments may include a motion capture element configured to transmit the data to a mobile device that comprises an application configured to blend at least two trajectories in the data to form a more accurate single trajectory. Other embodiments of the apparatus may be configured to output a motion gesture or circle gesture or number of taps gesture to enable the motion capture element to signify that particular motion capture element that is to be communicated with instead of one or more other motion capture elements within the vicinity of the mobile device. This enables easy pairing of devices in multiple device environments. One or more embodiments may include a motion capture element that further includes an output display for local viewing of motion capture data. This enables local display of acceleration or other motion related parameters without a mobile device and may be utilized within a helmet based mounting scenario so that potential concussions may be displayed locally without requiring any cell phones with apps for example.

As shown, embodiments of system 100 that may utilize motion capture data produced by motion capture element 111 generally include a mobile device 101 and applications that execute thereon, that includes computer 160, shown as located internally in mobile device 101 as a dotted outline, (i.e., also see functional view of computer 160 in FIG. 1A), display 120 coupled to computer 160 and a wireless communications interface (generally internal to the mobile device, see element 164 in FIG. 1A) coupled with the computer. Since mobile phones having mobile computers are ubiquitous, users of the system may purchase one or more motion capture elements and an application, a.k.a., "app", that they install on their pre-existing phone to implement an embodiment of the system that utilizes an embodiment of motion capture element 111. Motion capture capabilities are thus available at an affordable price for any user that already owns a mobile phone, tablet computer, music player, etc., which has never been possible before. Each mobile device 101, 102, 102a, 102b may optionally include an internal identifier reader 190, for example an RFID reader, or may couple with an identifier reader or RFID reader (see mobile device 102) to obtain identifier 191. Alternatively, embodiments of the invention may utilize any wireless technology in any of the devices to communicate an identifier that identifies equipment 110 to the system.

The motion capture data from motion capture element 111, any data associated with the piece of equipment 110, such as identifier 191 and any data associated with user 150, or any number of such users 150, such as second user 152 may be stored in locally in memory, or in a database local to the computer or in a remote database, for example database 172. Data may be stored in database 172 from each user 150, 152 for example when a network or telephonic network link is available from motion capture element 111 to mobile device 101 and from mobile device 101 to network 170 or Internet 171 and to database 172. One or more embodiments of the motion capture element may communicate directly with network 170 or directly with mobile device 101 or to network 170 via mobile device 101. Embodiments may utilize BLE or other communications devices and/or cellular chips for example to communicate wirelessly in a local or distal manner as desired and based on available power. Data mining is then performed on a large data set associated with any number of users and their specific characteristics and performance parameters. For example, in a golf embodiment of the invention, a club ID is obtained from the golf club and a shot is detected by the motion capture element. Mobile computer 101 stores images/video of the user and receives the motion capture data for the events/hits/shots/motion and the location of the event on the course and subsequent shots and determines any parameters for each event, such as distance or speed at the time of the event and then performs any local analysis and display performance data on the mobile device. When a network connection from the mobile device to network 170 or Internet 171 is available or for example after a round of golf, the images/video, motion capture data and performance data is uploaded to database 172, for later analysis and/or display and/or data mining. In one or more embodiments, users 151, such as original equipment manufacturers pay for access to the database, for example via a computer such as computer 105 or mobile computer 101 or from any other computer capable of communicating with database 172 for example via network 170, Internet 171 or via website 173 or a server that forms part of or is coupled with database 172. Data mining may execute on database 172, for example that may include a local server computer, or may be run on computer 105 or mobile device 101, 102, 102a or 102b and access a standalone embodiment of database 172 for example. Data mining results may be displayed on mobile device 101, computer 105, television broadcast or web video originating from camera 130, 130a and 103b, or 104 or accessed via website 173 or any combination thereof.

One or more embodiments of motion capture element 111 may communicate via BLUETOOTH® and/or Bluetooth Low Energy ("BLE"). BLE technology encompasses new hardware standards to reduce power consumption as well as a new software standard to access information on BLE devices. BLE may utilize one or more Low Energy Profiles that further conserve power. The associated software standard is known as "GATT" (Generic ATTribute profile). Mobile computer 105 and/or mobile device 101 and/or any other device supporting BLE utilizes a compatible hardware radio and adapter as well as the GATT-enabled software. Apps running on mobile device 101 for example having GATT software, use that software to communicate with BLE devices, such as a BLE embodiment of motion capture element 111. GATT is a relatively simple protocol that defines the features of BLE devices as a set of services, each of which includes of a set of characteristics that describe the data values associated with that service. An app communicating with a BLE device using GATT can perform essentially three operations: (1) Read the value of a characteristic from the device, (2) Send a new value for a characteristic to the device and (3) Command the device to notify the app whenever the value of a characteristic changes. The GATT software on mobile device 101 and in motion capture element 111 handles all of the low-level details of establishing a link to and exchanging messages to synchronize mobile device 101 and the motion capture element 111. This protocol simplifies the implementation of the app software. Using GATT enables developers to create custom Profiles for these services. There are some profiles that are approved by the Bluetooth Special Interest Group (SIG) related to battery, heart rate, temperature, etc. Devices implementing the appropriate profile will be compatible with software that implements the profile. BLE also allows for the development of proprietary profiles that are not adopted by the Bluetooth SIG. This is possible when the implementer of the profile controls the software on the master device and slave device. In one or more embodiments, a TEXAS INSTRUMENTS® TICC2540 chip is utilized as the BLE solution.

This chip allows master or slave mode to be switched programmatically to enable each motion capture element 111 to become a master or slave as desired. In one or more embodiments, if the mobile device 101 is unavailable for a predetermined amount of time, then a fallback master is arbitrated by each chip, for example by sending a time stamp wherein the largest time stamp sent becomes the master. The master then coordinates between chips to save data until communications is restored to mobile device 101 for example. Any other mechanism for utilizing master and slave modes of the BLE device is in keeping with the spirit of the invention.

One or more embodiments of the invention utilize a custom proprietary profile in compliance with GATT but which is generic as follows. One embodiment utilizes GATT to define a unique 128-bit UUID (universally unique identifier) service. Under this profile a single characteristic is defined that enables the sending and receiving of a string of bytes. Embodiments thus utilize GATT to define a profile that behaves much like a serial port, wherein the port and you is configured to send and receive data. The software or device on either end of this GATT profile can then decode the message that is being sent through the single characteristic. One or more embodiments of the invention also may utilize a custom proprietary profile using GATT. This profile includes a set of services and characteristics specific for the application. This includes the following services: battery, accelerometer, gyroscope, magnetometer, time, temperature. Asserting characteristics associated with these services enables communication of associated values. This may occur on an event or timed basis via motion capture element 111 or as polled effectively by mobile computer 105 or mobile device 101 for example. In one or more embodiments of the invention, any motion capture element 111 may switch automatically from master to slave mode and/or relay messages to any other motion capture element for transmittal to mobile device 101 or any other computer that may wirelessly communicate with motion capture element 111.

One or more embodiments of the invention are configured to update firmware wirelessly. In one or more embodiments, the microcontroller coupled with the sensors includes a boot loader in memory, for example non-volatile memory. The boot loader interacts with the wireless transceiver (or transmitter and receiver) to obtain a new firmware image for the microcontroller. The firmware is stored in the memory at which time there are two firmware code sets stored in the memory, i.e., the old firmware and the new firmware. Once the firmware is validated, for example via any type of validity check, e.g., CRC check (cyclic redundancy check), then the boot loader begins to execute the new firmware and frees the memory associated with the old firmware. The boot loader may optionally assert that the firmware has successfully been updated.

In one or more embodiments of the communication protocol utilized on the wireless interface coupled with the microcontroller, may include BLE Notifications. For example, communications between the remote computer 101, 105, etc., having the firmware, i.e., sender of the firmware and the receiver of the firmware, i.e., motion capture element 111 may be via BLE Notifications. The server sends notifications with the handle of its own characteristic 128-bit UUID, which the target will be looking for because it will have done service discovery for this well known 128-bit characteristic after pairing. The server, for example mobile device 101 performs discovery for this 128-bit characteristic on motion capture element 111, because responses will be received from this motion capture element 111 as Notifications with that handle.

This profile, identified by 128-bit UUID, is referred to herein as the GSP Profile (for Generic Serial Protocol, similar to a mini-BLE equivalent to the BlueTooth SPP profile). However, the protocol can do include significantly more functionality than firmware download. The same profile may be utilized to rapidly and efficiently obtain motion capture data as well, which provides saving in code size and complexity.

128-Bit Service UUID:

This service may be implemented with one characteristic, which sends and receives Notifications (it does not do read, or write, etc.), and the characteristic may be implemented with its own 128-bit UUID. For example, packets sent through this GSP pipe may utilize this structure:

<SOP><CMD LSB><CMD MSB><LEN LSB><LEN MSB><DATA><CHK>

The Command MSB and the Length LSB and MSB and Data are all optional and vary according to the Command LSB.

For firmware operations, everything is simplified by the fact that Command MSB and Length LSB/MSB are not required to be used, i.e., in one or more embodiments, the commands and responses have known lengths. In this case, the OAD packets will be one of two formats:

<SOP><CMD LSB><DATA><CHK>
<SOP><CMD LSB><CHK>

Wherein the "SOP" is a start-of-packet indicator which may be implemented as having a value of 0xFE. The "CHK", i.e., packet checksum, may be implemented for example as the byte-wise sum of all bytes, excluding the SOP, subtracted from 0x100. Any other type of checksum may be utilized as desired. In the example described herein, the sum of all bytes, excluding the SOP and FCS, added to the FCS should result in zero for a valid packet that has not been corrupted.

A subset of the 65536 commands that this pipe can handle may be reserved for firmware download as follows, namely commands 0x70-0x7F.

define GSP_OAD_REQ_ID 0x70//Len=0 Request the RC image Id.
define GSP_OAD_REQ_BEG 0x71//Len=0 Get ready to begin a DL transfer.
define GSP_OAD_REQ_CHK 0x72//Len=0 Calculate the CRC over the DL image.
define GSP_OAD_CMD_DAT 0x77//Len=128 128-byte chunk of DL image.
define GSP_OAD_CMD_JMP 0x78//Len=0 Jump to boot loader; instantiate DL.
define GSP_OAD_CMD_ADR 0x79//Len=2 Set server address back as specified.
define GSP_OAD_RSP_CHK 0x7D//Len=1 True/false response to check DL.
define GSP_OAD_RSP_BEG 0x7E//Len=0 Ready to receive a DL transfer.
define GSP_OAD_RSP_ID 0x7F//Len=4 Response with the RC image Id.

Notifications from the server, i.e., source of the firmware, are 0x70, 0x71, 0x72, 0x77 and 0x78, which are described in further detail below:

0x70—a server should request the image Id to determine if motion capture element 111 it has paired with
 a) needs this image
 b) is compatible with this image In one or more embodiments, a 4-byte image Id may be utilized to identify classes of devices, and within each class, the s/w version, etc.

Notification from Server to Target:
FE 70 90

0x71—server commands motion capture element 111 to get ready to receive a download, the target pre-erases the memory, for example flash pages used to store the firmware so that the transfer is faster

FE 71 8F

0x72—server finished uploading the firmware to motion capture element 111 and now commands the motion capture element 111 to perform a CRC calculation over the image stored in memory to ensure that it is acceptable to provide to the boot loader to instantiate in memory as the new firmware to execute.

FE 72 8E

0x77—server feeds 128 bytes at a time. This number can be increased or decreased if desired. Whatever this number is, it generally should be an even multiple of both the memory word size, for example flash word size (4) and the flash bank size (32 kb). The payload of this packet starts with the relative offset of the 128-bytes, in LSB, MSB order. The image to send is a monolithic binary image with code gaps filled with 0xFF so there is no addressing information in it. As the firmware is divided into 128-byte chunks and sent, the offset is prepended into this monolithic image. The offset for example is calculated as the "Actual Offset/Flash Word Size".

In one or more embodiments, standard flash word size is 4. The reason for the division is that it allows the entire image to be indexed with a unit 16, and because the Addr/4 is what is used to write to internal flash locations anyway. This identifies the relative chunk, i.e., the relative index into the monolithic image. So the 2nd 128-byte chunk will be identified as 128/4→0x0020, and appears in the packet below like this:

FE 77 20 00 . . . 128 bytes of monolithic binary data . . . CHKSUM where the CHKSUM is again optionally the byte-wise sum of all 128 binary data bytes, plus 0x77, 0x20, 0x00, and then subtracted from 0x100.

0x78—when server receives the 0x7D check image response with success, the server commands motion capture element 111 to act on this new image by resetting into the boot loader which instantiates the downloaded firmware image as the new run-code image.

FE 78 88

Responses from the OAD target are 0x7D, 0x7E and 0x7F

0x7D—acting on this command takes a microcontroller such as the SILICON LABS® 8051 about a minute to do the byte-wise CRC of the downloaded image and compare it to the CRC in the message. This response has 1 byte, a Boolean where 1 (True) means that the CRC matches and the image is good, 0 otherwise:

FE 7D 00 83 on fail to match

FE 7D 01 82 on success

0x7E—acting on the command to prepare to receive and download, the target pre-erases all of the memory, for example flash pages, that will be used to store the downloaded firmware image and responds with success when done with the following message:

FE 7E 01 81

0x7F—responding with the 4-byte image Id of the currently running image. Consider the image Id of 0x01020304:

FE 7F 04 03 02 01 77

In the case of motion capture element 111 receiving a corrupted notification, motion capture element 111 may force the server to backup and restart sending the image from a given address, so a command from motion capture element 111 to the server in this case may be implemented as 0x79:

0x79—when a bad notification is detected, the microcontroller keeps track of the last good packet that was received. The microcontroller will then request the relative offset into the monolithic image where transmission should start again by requesting and receiving 0x77 commands. Thus the two-byte payload in LSB, MSB order is the equivalent of the offset being prepended to the 0x77 data. For example if the last good packet had relative offset 0x1240, and after recovering parsing after a bad notification, the address is far past that, the target will request to go back to 0x1260 (the next 128-byte chunk that is required to continue the contiguous valid data):

FE 79 60 12 15

One or more embodiments are also configured to conserve battery power by maintaining a link between the radio in the motion capture element and the radio in the mobile computer or other external device wherein the link includes a connection interval. The connection interval is the preconfigured interval at which the two radios communicate with one another to inform one another that the communication link is still alive. In this manner the radios may minimize transmissions so that the link is maintained, or otherwise dropped if no response occurs over a given threshold. For example if connection interval is set to 1 second, then every second a communication may occur from one radio to the other and or in both directions to inform one or both devices that the link is alive. Generally, the longer the connection interval, the less power utilized. In one or more embodiments, the connection interval may be changed or throttled based on the amount of data being transferred, or based on motion capture sensor values. For example, a long connection interval may be utilized while maintaining a link with a mobile computer, such as a mobile phone wherein there is no motion capture data to transfer, for example if no swing event, etc., has occurred. If however an event has occurred or for any other reason, a shorter connection interval may be switched to, so that the link is maintained during transfer with for example shorter intervals between data messages for example. The longer connection interval may be switched to when there is no data to send, yet the two devices still desire to maintain the link between them. In one or more embodiments the motion capture element microcontroller for example maintains a communication link between the radio and a second radio through transmission of information via the radio at a first communication interval when no valid event has occurred over a predetermined first period wherein the first communication interval between transmission of information is longer than a time interval between transmission of packets related to a valid event or other motion capture data.

In addition, embodiments of the invention may intelligently calculate or estimate a gravity vector for orientation at one or more points in time to increase accuracy and change sampling rates as a function of time or acceleration to further increase accuracy over a particular G-force range for example. One or more embodiments of motion capture element 111 measure acceleration directly via accelerometers, which do not directly measure speed. Acceleration is the rate of change of velocity and angular velocity is the rate of change of orientation. One or more embodiments of motion capture element 111 and/or mobile device 101 include program code configured to implement an algorithm on a computer to estimate initial velocity and initial orientation. The measured data is then integrated via an "inertial navigation" algorithm to derive speed. This integration algorithm utilizes the estimate of the initial velocity and initial orientation of motion capture element 111 at the beginning of integration.

One or more embodiments of motion capture element 111 may also not directly measure the initial conditions, i.e., the initial velocity and initial orientation. However under certain conditions the initial velocity and initial orientation can be estimated indirectly from the motion capture data. The simplest approach is to presume, a period of time during which motion capture element 111 and/or piece of equipment 110 and/or user 150 having is at rest. In this case the accelerometer readings reflect the tilt of the sensor, but not the heading, and the initial orientation of motion capture element 111 can be derived from the accelerometer. Note that in one or more embodiments, heading is presumed since an accelerometer cannot directly measure heading. The initial velocity in this case is assumed to be zero since motion capture element 111 is presumed to be at rest.

As follows, boldface lower case letters represent vectors, and upper case letters represent matrices. A superscript on a vector indicates the reference frame for the vector: $u^W$ is vector u measured in the world reference frame, while $u^B$ is the vector u measured in the "body frame" of the sensor. If no subscript is provided, the vector is measured in the world reference frame. The following quantities are listed below and are utilized in one or more embodiments of the algorithm to estimate initial velocity and initial orientation at the beginning of integration:

$s^B$ The reading from the accelerometer on motion capture element 111. s is "specific force"; it measures the combination of acceleration and gravity.

$\overline{s^B}$ Average of accelerometer readings over some time period.

g The gravity vector. In the world reference frame g points in the −z direction.

Q The orientation of the sensor relative to the world reference frame. This is an orthogonal, or "rotation" matrix that transforms vectors measured in the sensor reference frame into equivalent vectors measured in the world reference frame. Thus for a vector u we have $Qu^B = u^W$ $Q_0$ The initial orientation of motion capture element 111, prior to the inertial navigation integration.

v Velocity of motion capture element 111, measured in the world reference frame.

$v_0$ The initial velocity of motion capture element 111, prior to the inertial navigation integration.

The simplest initialization is performed presuming that motion capture element 111 is at rest for some period of time, is to find $Q_0$ so that $$Q_0 \overline{s^B} = -g$$

and to set $v_0=0$. The equation $Q_0 s^B=-g$ signifies that the accelerometer is measuring gravity only (actually the negative of gravity), assuming there is no motion. However the accelerometer measures gravity in the accelerometer's reference frame, so the motion capture data is transformed to the global frame via matrix $Q_0$ to recover the gravity vector. This approach is simple, but it may not give good results if the assumption of no motion during the initialization period is false. Hence, one or more embodiments of the invention may utilize a more sophisticated initialization algorithm that attempts to compensate for possible motion during the initialization period. To describe this algorithm the core differential equations involved in inertial navigation are explained below along with the following additional quantities:

$\omega^B$ The angular velocity reading from the gyro in motion capture element 111.

$\omega^W$ The angular velocity of motion capture element 111 in the world reference frame.

$S(\omega)$ The skew-symmetric matrix corresponding to the cross-product with $\omega$: $S(\omega)u = \omega \times u$ a Acceleration of motion capture element 111, measured in the world reference frame. Note that this is not the same as the accelerometer reading, since (1) it is in the world frame, not the sensor frame ($a=a^W$); and (2) it does not include the effect of gravity.

The dynamic state of motion capture element 111, at any point in time, may be defined by the quantities Q, v, a, $\omega$. These are functions of time. They are linked by the differential equations:

$$\frac{dv}{dt} = a$$

$$\frac{dQ}{dt} = S(\omega)Q$$

Since one or more embodiments of motion capture element 111 measures $s^B$ and $\omega^B$ rather than $a^W$ and $\omega^W$, these differential equations are transformed to use the motion capture data from motion capture element 111:

$$\frac{dv}{dt} = Qs^B + g$$

$$\frac{dQ}{dt} = QS(\omega^B)$$

Note that the transformation of the second differential equation is non-obvious, but rather follows from the identity $S(Q\omega) = QS(\omega)Q^T$.

If the initial conditions $v_0$, $Q_0$ are known, then in principle it is possible to integrate the gyro and accelerometer readings and calculate velocity and orientation throughout motion of motion capture element 111, for example during a swing of piece of equipment 110. If Q(t) is found by integrating the second equation, then the first equation may be integrated as follows:

$v(t) = v_0 + \int_0^t (Qs^B + g)dt = v_0 + \int_0^t Qs^B dt + gt$

Determining Q(t) is performed by integrating $$\frac{dQ}{dt} = QS(\omega^B),$$

which is straightforward, however the initial condition $Q(0) = Q_0$, i.e., the starting orientation, is generally unknown. It is possible to "factor out" $Q_0$ as follows: By defining P(t) by $Q(t) = Q_0 P(t)$, then P satisfies the same differential equation:

$$\frac{dQ}{dt} = Q_0 \frac{dP}{dt} = QS(\omega^B) = Q_0 PS(\omega^B)$$

$$\Rightarrow \frac{dP}{dt} = PS(\omega^B)$$

And the initial condition for P is simply P(0)=I. P represents the net change in orientation from a particular starting orientation, which may be unknown. The equation may then be integrated to find P(t). The transformation is then applied to the equation for velocity:

$v(t) = v_0 + \int_0^t Q_0 Ps^B dt + gt = v_0 + Q_0 \int_0^t Ps^B dt + gt$

Here $Q_0$ have been "factored out" from the velocity integral. The notation is simplified by defining $u(t) = \int_0^t Ps^B dt$; which yields:

$v(t) = v_0 + Q_0 u(t) + gt$

This expression provides a simple way to calculate $Q_0$, provided that $v_0$ and $v(t)$ are known at some point in time. In general $v_0$ is unknown, and in fact is unknowable in embodiments of motion capture element 111 that include only an accelerometer and a gyro as sensors. However a point in time may be identified, for example during "address", e.g., when a golf club is placed near a golf ball before a swing. At this point in time, it is possible to estimate that $v_0$ is very small. If we find a second such point at a different time, t, then it is possible to use $v_0 \approx v(t) \approx 0$ to solve for $Q_0$ using $$Q_0 u(t) = -gt$$

The advantage of this approach is that the assumption for initialization is less strict than a simple "average accelerometer reading" approach. By finding two points in time, for example during "address" where linear velocity is small, then it is possible to integrate between these points to find the initial orientation.

Note that the simple approach is a special case of the more sophisticated method. If in fact motion capture element 111 is completely at rest during the initialization interval, then $P(t) \equiv 1$, and $u(t) = \int_0^t s^B dt = t\overline{s^B}$. So $Q_0 u(t) = -gt$ implies $Q_0 \overline{s^B} = -g$, which is the simplest method for finding initial orientation as previously described.

Embodiments of the microcontroller may be further configured to recalibrate the sensor through measurement of changes in linear acceleration during a motionless period for the sensor, computation of an average of the linear acceleration along each axis, computation of an average magnitude of the linear acceleration $g_m$, comparison of $g_m$ to g wherein g is 9.8 m/sec$^2$, calculation of a scaling factor $s = g/g_m$ and multiplication of a calibration matrix by the scaling factor if a difference between g and $g_m$ exceeds a predefined threshold. Other embodiments of the microcontroller may perform calibration or recalibration through measurement of linear acceleration during a low acceleration time window for at least two axes of the sensor, comparison of differences in linear acceleration in the low acceleration time window and performance of a recalibration using calibration data from a below threshold sensor or transmission of an out of calibration alert.

Proximity sensors may be coupled with an embodiment of motion capture element 111 or identification tag 191 or mount 192 or mobile device 101 or any combination thereof, and may be utilized to determine whether a piece of sporting equipment has been accidentally left behind or is the piece of equipment being utilized, or may be utilized for shot tracking for certain types of equipment in certain sports. Proximity sensors for example may be combined on an ASIC with embodiments of motion capture element 111 to provide increased capabilities. In addition, a BLE radio may be combined on an ASIC with motion capture element 111 to provide a single chip solution for motion capture, for example by adding a gyro and accelerometer, e.g., 3 axes each. One or more embodiments of the invention may communicate with a mobile computer that is local using local communications protocols or may communicate distally using longer range communications protocols as desired and based on available energy. For example, if user 150 has two or more pieces of equipment 110 and the proximity sensor in mobile device 101 indicates that a first piece of equipment is closer than a second piece of equipment or simply reads that the first piece of equipment is within a predetermined range, while the second piece of equipment is not, then the first piece of equipment may be accepted by mobile device 101 as the piece of equipment being utilized by user 150. Any other algorithm using proximity sensors coupled with motion capture element 111 or identification tag 191 or mount 192 or mobile device 101 is in keeping with the spirit of the invention. In one or more embodiments of the motion capture element, if the orientation of the piece of equipment is upside down, then the piece of equipment is for example in a bag, e.g., a golf bag, and then the proximity detection may take this into account to discount the closest value.

Embodiments of the invention may be utilized to provide an alarm clock, or integrate with an alarm clock for example on mobile device 101 for example by utilizing motion capture data associated with motion capture element 111 coupled with user 150 or in mobile device 101 coupled with user 150, wherein the alarm stops when the motion capture element coupled with user 150 is moved when user 150 moves. In one or more embodiments of the invention, this enables user 150 to "gesture" an alarm off signal, or a sleep signal. I.e., by waving a hand having motion capture element, for example coupled with a watch band, an "off signal" may be gestured, while rotating a hand axially may be accepted by the system to indicate a "5 minute sleep" assertion. Any other motion of motion capture element 111 to interact with an alarm clock is in keeping with the spirit of the invention. For example, user 150 may twist the foot having motion capture element 111 and/or mount 192 which sends motion capture data to mobile device 101 that is transmitting an audible or tactile alarm via an alarm app that is executing on computer 160 for example. By receiving a first type or motion (slow shake) or a second type of motion (fast shake), the command associated with the first motion or second motion may be interpreted by the app to turn the alarm off or sleep for a predetermined amount of time respectively. Again, any type of motion for a gesture may be associated with a desired command related to an alarm including "drawing" a number of minutes to sleep with a hand for example. I.e., slowing moving in a "1" shape from top to bottom, then quickly moving to the top of a "0" and slowly moving the hand in a "zero" shape, to indicate 10 minutes more of sleep.

One or more embodiments of the system may utilize a mobile device that includes at least one camera 130, for example coupled to the computer within the mobile device. This allows for the computer within mobile device 101 to command the camera 130 to obtain an image or images, for example of the user during an athletic movement. The image(s) of the user may be overlaid with displays and ratings to make the motion analysis data more understandable to a human for example. Alternatively, detailed data displays without images of the user may also be displayed on display 120 or for example on the display of computer 105. In this manner two-dimensional images and subsequent display thereof is enabled. If mobile device 101 contains two cameras, as shown in mobile device 102, i.e., cameras 130*a* and 130*b*, then the cameras may be utilized to create a three-dimensional data set through image analysis of the visual markers for example. This allows for distances and positions of visual markers to be ascertained and analyzed. Images and/or video from any camera in any embodiments of the invention may be stored on database 172, for example associated with user 150, for data mining purposes. In one or more embodiments of the invention image analysis on the images and/or video may be performed to determine make/models of equipment, clothes, shoes, etc., that is utilized, for example per age of user 150 or time of day of play, or to discover any other pattern in the data.

Alternatively, for embodiments of mobile devices that have only one camera, multiple mobile devices may be utilized to obtain two-dimensional data in the form of images that is triangulated to determine the positions of visual markers. In one or more embodiments of the system, mobile device 101 and mobile device 102a share image data of user 150 to create three-dimensional motion analysis data. By determining the positions of mobile devices 101 and 102 (via position determination elements such as GPS chips in the devices as is common, or via cell tower triangulation and which are not shown for brevity but are generally located internally in mobile devices just as computer 160 is), and by obtaining data from motion capture element 111 for example locations of pixels in the images where the visual markers are in each image, distances and hence speeds are readily obtained as one skilled in the art will recognize.

Camera 103 may also be utilized either for still images or as is now common, for video. In embodiments of the system that utilize external cameras, any method of obtaining data from the external camera is in keeping with the spirit of the system including wireless communication of the data, or via wired communication as when camera 103 is docked with computer 105 for example, which then may transfer the data to mobile device 101.

In one or more embodiments of the system, the mobile device on which the motion analysis data is displayed is not required to have a camera, i.e., mobile device 102b may display data even though it is not configured with a camera. As such, mobile device 102b may obtain images from any combination of cameras on mobile device 101, 102, 102a, camera 103 and/or television camera 104 so long as any external camera may communicate images to mobile device 102b. Alternatively, no camera is required at all to utilize the system.

For television broadcasts, motion capture element 111 wirelessly transmits data that is received by antenna 106. The wireless sensor data thus obtained from motion capture element 111 is combined with the images obtained from television camera 104 to produce displays with augmented motion analysis data that can be broadcast to televisions, computers such as computer 105, mobile devices 101, 102, 102a, 102b or any other device configured to display images. The motion analysis data can be positioned on display 120 for example by knowing the location of a camera (for example via GPS information), and by knowing the direction and/or orientation that the camera is pointing so long as the sensor data includes location data (for example GPS information). In other embodiments, visual markers or image processing may be utilized to lock the motion analysis data to the image, e.g., the golf club head can be tracked in the images and the corresponding high, middle and low position of the club can be utilized to determine the orientation of user 150 to camera 130 or 104 or 103 for example to correctly plot the augmented data onto the image of user 150. By time stamping images and time stamping motion capture data, for example after synchronizing the timer in the microcontroller with the timer on the mobile device and then scanning the images for visual markers or sporting equipment at various positions, simplified motion capture data may be overlaid onto the images. Any other method of combining images from a camera and motion capture data may be utilized in one or more embodiments of the invention. Any other algorithm for properly positioning the motion analysis data on display 120 with respect to a user (or any other display such as on computer 105) may be utilized in keeping with the spirit of the system.

One such display that may be generated and displayed on mobile device 101 include a BULLET TIME® view using two or more cameras selected from mobile devices 101, 102, 102a, camera 103, and/or television camera 104 or any other external camera. In this embodiment of the system, the computer is configured to obtain two or more images of user 150 and data associated with the at least one motion capture element (whether a visual marker or wireless sensor), wherein the two or more images are obtained from two or more cameras and wherein the computer is configured to generate a display that shows slow motion of user 150 shown from around the user at various angles at normal speed. Such an embodiment for example allows a group of fans to create their own BULLET TIME® shot of a golf pro at a tournament for example. The shots may be sent to computer 105 and any image processing required may be performed on computer 105 and broadcast to a television audience for example. In other embodiments of the system, the users of the various mobile devices share their own set of images, and or upload their shots to a website for later viewing for example. Embodiments of the invention also allow images or videos from other players having mobile devices to be utilized on a mobile device related to another user so that users don't have to switch mobile phones for example. In one embodiment, a video obtained by a first user for a piece of equipment in motion that is not associated with the second user having the video camera mobile phone may automatically transfer the video to the first user for display with motion capture data associated with the first user.

FIG. 1A shows an embodiment of computer 160. In computer 160 includes processor 161 that executes software modules, commonly also known as applications, generally stored as computer program instructions within main memory 162. Display interface 163 drives display 120 of mobile device 101 as shown in FIG. 1. Optional orientation/position module 167 may include a North/South or up/down orientation chip or both. Communication interface 164 may include wireless or wired communications hardware protocol chips and/or an RFID reader or an RFID reader may couple to computer 160 externally or in any other manner for example. In one or more embodiments of the system communication interface may include telephonic and/or data communications hardware. In one or more embodiments communication interface 164 may include a Wi-Fi™ or other IEEE 802.11 device and/or BLUETOOTH® wireless communications interface or ZigBee® wireless device or any other wireless technology. BLUETOOTH® class 1 devices have a range of approximately 100 meters, class 2 devices have a range of approximately 10 meters. BLUETOOTH® Low Power devices have a range of approximately 50 meters. Any wireless network protocol or type may be utilized in embodiments of the system so long as mobile device 101 or any other computer in the system and motion capture element 111 can communicate with one another. Processor 161, main memory 162, display interface 163, communication interface 164 and orientation/position module 167 may communicate with one another over communication infrastructure 165, which is commonly known as a "bus". Communications path 166 may include wired or wireless medium that allows for communication with other wired or wireless devices over network 170. Network 170 may communicate with Internet 171 and/or database 172. Database 172 may be utilized to save or retrieve images or videos of users, or motion analysis data, or users displayed with motion analysis data in one form or another. The data uploaded to the Internet, i.e., a remote database or remote server or memory remote to the system may be viewed, analyzed or data mined by any computer that may obtain access to the data. This allows for original equipment manufacturers to determine for a given user what sporting equipment is working best and/or what equipment to suggest. Data mining also enables the planning of golf courses based on the data and/or metadata associated with users, such as age, or any other demographics that may be entered into the system. Remote storage of data also enables medical applications such as morphological analysis, range of motion over time, and diabetes prevention and exercise monitoring and compliance applications. Data mining based applications also allow for games that use real motion capture data from other users, or historical players whether alive or dead after analyzing videos of the historical players for example. Virtual reality and augmented virtual reality applications may also utilize the motion capture data or historical motion data. The system also enables uploading of performance related events and/or motion capture data to database 172, which for example may be implemented as a social networking site. This allows for the user to "tweet" high scores, or other metrics during or after play to notify everyone on the Internet of the new event.

FIG. 1B illustrates an architectural view of an embodiment of database 172 utilized in embodiments of the system. As shown tables 180-185 include information related to N number of users, M pieces of equipment per user, P number of sensors per user or equipment, S number of sensor data per sensor, T number of patterns found in the other tables, and D number of data users. All tables shown in FIG. 1B are exemplary and may include more or less information as desired for the particular implementation. Specifically, table 180 includes information related to user 150 which may include data related to the user such as age, height, weight, sex, address or any other data. Table 181 include information related to M number of pieces of equipment 110, which may include clubs, racquets, bats, shirts, pants, shoes, gloves, helmets, etc., for example the manufacturer of the equipment, model of the equipment, and type of the equipment. For example, in a golf embodiment, the manufacturer may be the name of the manufacturer, the model may be a name or model number and the type may be the club number, i.e., 9 iron, the equipment ID may be identifier 191 in one or more embodiments of the invention. Table 182 may include information related to P number of sensors 111 on user 150 or equipment 110 or mobile computer 101. The sensors associated with user 150 may include clothing, clubs, etc., the sensors associated with equipment 110 may for example be motion capture data sensors, while the sensors associated with mobile computer 101 may include sensors 167 for position/orientation and sensors 130 for images/video for example. Table 183 may include information related to S number of sensor data per user per equipment, wherein the table may include the time and location of the sensor data, or any other metadata related to the sensor data such as temperature, weather, humidity, etc., or the sensor data may include this information or any combination thereof. The table may also contain a myriad of other fields, such as ball type, i.e., in a golf embodiment the type of golf ball utilized may be saved and later data mined for the best performing ball types, etc. Table 184 may include information related to T number of patterns that have been found in the data mining process for example. This may include fields that have been searched in the various tables with a particular query and any resulting related results. Any data mining results table type may be utilized in one or more embodiments of the invention as desired for the particular implementation. This may include search results of any kind, including EI measurements, which also may be calculated on computer 160 locally, or any other search value from simple queries to complex pattern searches. Table 185 may include information related to D number of data mining users 151 and may include their access type, i.e., full database or pattern table, or limited to a particular manufacturer, etc., the table may also include payment requirements and/or receipts for the type of usage that the data mining user has paid for or agreed to pay for and any searches or suggestions related to any queries or patterns found for example. Any other schema, including object oriented database relationships or memory based data structures that allow for data mining of sensor data including motion capture data is in keeping with the spirit of the invention. Although exemplary embodiments for particular activities are given, one skilled in the art will appreciate that any type of motion based activity may be captured and analyzed by embodiments of the system using a motion capture element and app that runs on a user's existing cell phone 101, 102 or other computer 105 for example.

There are a myriad of applications that benefit and which are enabled by embodiments of the system that provide for viewing and analyzing motion capture data on the mobile computer or server/database, for example for data mining database 172 by users 151. For example, users 151 may include compliance monitors, including for example parents, children or elderly, managers, doctors, insurance companies, police, military, or any other entity such as equipment manufacturers that may data mine for product improvement. For example in a tennis embodiment by searching for top service speeds for users of a particular size or age, or in a golf embodiment by searching for distances, i.e., differences in sequential locations in table 183 based on swing speed in the sensor data field in table 183 to determine which manufacturers have the best clubs, or best clubs per age or height or weight per user, or a myriad of other patterns. Other embodiments related to compliance enable messages from mobile computer 101 or from server/database to be generated if thresholds for G-forces, (high or zero or any other levels), to be sent to compliance monitors, managers, doctors, insurance companies, etc., as previously described. Users 151 may include marketing personnel that determine which pieces of equipment certain users own and which related items that other similar users may own, in order to target sales at particular users. Users 151 may include medical personnel that may determine how much movement a sensor for example coupled with a shoe, i.e., a type of equipment, of a diabetic child has moved and how much this movement relates to the average non-diabetic child, wherein suggestions as per table 185 may include giving incentives to the diabetic child to exercise more, etc., to bring the child in line with healthy children. Sports physicians, physiologists or physical therapists may utilize the data per user, or search over a large number of users and compare a particular movement of a user or range of motion for example to other users to determine what areas a given user can improve on through stretching or exercise and which range of motion areas change over time per user or per population and for example what type of equipment a user may utilize to account for changes over time, even before those changes take place. Data mining motion capture data and image data related to motion provides unique advantages to users 151. Data mining may be performed on flex parameters measured by the sensors to determine if sporting equipment, shoes, human body parts or any other item changes in flexibility over time or between equipment manufacturers or any combination thereof.

To ensure that analysis of user 150 during a motion capture includes images that are relatively associated with the horizon, i.e., not tilted, the system may include an orientation module that executes on computer 160 within mobile device 101 for example. The computer is configured to prompt a user to align the camera along a horizontal plane based on orientation data obtained from orientation hardware within mobile device 101. Orientation hardware is common on mobile devices as one skilled in the art will appreciate. This allows the image so captured to remain relatively level with respect to the horizontal plane. The orientation module may also prompt the user to move the camera toward or away from the user, or zoom in or out to the user to place the user within a graphical "fit box", to somewhat normalize the size of the user to be captured. Images may also be utilized by users to prove that they have complied with doctors orders for example to meet certain motion requirements.

Embodiments of the system are further configured to recognize the at least one motion capture element associated with user 150 or piece of equipment 110 and associate at least one motion capture element 111 with assigned locations on user 150 or piece of equipment 110. For example, the user can shake a particular motion capture element when prompted by the computer within mobile device 101 to acknowledge which motion capture element the computer is requesting an identity for. Alternatively, motion sensor data may be analyzed for position and/or speed and/or acceleration when performing a known activity and automatically classified as to the location of mounting of the motion capture element automatically, or by prompting the user to acknowledge the assumed positions.

One or more embodiments of the computer in mobile device 101 is configured to obtain at least one image of user 150 and display a three-dimensional overlay onto the at least one image of user 150 wherein the three-dimensional overlay is associated with the motion analysis data. Various displays may be displayed on display 120. The display of motion analysis data may include a rating associated with the motion analysis data, and/or a display of a calculated ball flight path associated with the motion analysis data and/or a display of a time line showing points in time along a time axis where peak values associated with the motion analysis data occur and/or a suggest training regimen to aid the user in improving mechanics of the user. These filtered or analyzed data sensor results may be stored in database 172, for example in table 183, or the raw data may be analyzed on the database (or server associated with the database or in any other computer or combination thereof in the system shown in FIG. 1 for example), and then displayed on mobile computer 101 or on website 173, or via a television broadcast from camera 104 for example. Data mining results may be combined in any manner with the unique displays of the system and shown in any desired manner as well.

Embodiments of the system may also present an interface to enable user 150 to purchase piece of equipment 110 over the wireless interface of mobile device 101, for example via the Internet, or via computer 105 which may be implemented as a server of a vendor. In addition, for custom fitting equipment, such as putter shaft lengths, or any other custom sizing of any type of equipment, embodiments of the system may present an interface to enable user 150 to order a customer fitted piece of equipment over the wireless interface of mobile device 101. Embodiments of the invention also enable mobile device 101 to suggest better performing equipment to user 150 or to allow 150 to search for better performing equipment as determined by data mining of database 172 for distances of golf shots per club for users with swing velocities within a predefined range of user 150. This allows for real life performance data to be mined and utilized for example by users 151, such as OEMs to suggest equipment to user 150, and be charged for doing so, for example by paying for access to data mining results as displayed in any computer shown in FIG. 1 or via website 173 for example. In one or more embodiments of the invention database 172 keeps track of OEM data mining and is configured to bill users 151 for the amount of access each of users 151 has purchased and/or used for example over a giving billing period. See FIG. 1B for example.

Embodiments of the system are configured to analyze the data obtained from at least one motion capture element and determine how centered a collision between a ball and the piece of equipment is based on oscillations of the at least one motion capture element coupled with the piece of equipment and display an impact location based on the motion analysis data. This performance data may also be stored in database 172 and used by OEMs or coaches for example to suggest clubs with higher probability of a centered hit as data mined over a large number of collisions for example.

While FIG. 1A depicts a physical device, the scope of the systems and methods set forth herein may also encompass a virtual device, virtual machine or simulator embodied in one or more computer programs executing on a computer or computer system and acting or providing a computer system environment compatible with the methods and processes implementing the disclosed ideas. Where a virtual machine, process, device or otherwise performs substantially similarly to that of a physical computer system of the system, such a virtual platform will also fall within the scope of a system of the disclosure, notwithstanding the description herein of a physical system such as that in FIG. 1A.

FIG. 1C illustrates a flow chart for an embodiment of the processing performed and enabled by embodiments of the computers utilized in the system. In one or more embodiments of the system, optionally a plurality of motion capture elements are calibrated (see FIG. 11B for an example of a multiple motion capture element mounting device that may be moved in a specific manner to calibrate multiple sensors at once for mass production). In some embodiments this means calibrating multiple sensors on a user or piece of equipment to ensure that the sensors are aligned and/or set up with the same speed or acceleration values for a given input motion. In other embodiments of the invention, this means placing multiple motion capture sensors on a calibration object that moves and calibrates the orientation, position, speed, acceleration, or any combination thereof at the same time. The next optional step involves providing motion capture elements and an app for example that allows a user with an existing mobile phone or computer to utilize embodiments of the system to obtain motion capture data, and potentially analyze and/or send messages based thereon. In one or more embodiments, users may simply purchase a motion capture element and an app and begin immediately using the system. One or more embodiments of the system also allow optionally for providing motion capture mounts for the particular desired mounting location on a user or equipment. The system captures motion data with motion capture element(s) and sends the motion capture data to a mobile computer 101, 102 or 105 for example, which may include an IPOD®, ITOUCH®, IPAD®, IPHONE®, ANDROID® Phone or any other type of computer that a user may utilize to locally collect data. One or more mounts may be utilized, include for an embodiment of the mobile computer, for example a small format IPOD® as per FIG.

41A. This minimizes the complexity of the sensor and offloads processing to extremely capable computing elements found in existing mobile phones and other electronic devices for example. The transmitting of data from the motion capture elements to the user's computer may happen when possible, periodically, on an event basis, when polled, or in any other manner as will be described in various sections herein. This saves great amount of power compared to known systems that continuously send raw data in two ways, first data may be sent in event packets, within a time window around a particular motion event which greatly reduces the data to a meaningful small subset of total raw data, and secondly the data may be sent less than continuously, or at defined times, or when asked for data so as to limit the total number of transmissions. The main intelligence in the system is generally in the mobile computer or server where more processing power may be utilized and so as to take advantage of the communications capabilities that are ubiquitous in existing mobile computers for example. In one or more embodiments of the system, the mobile computer may optionally obtain an identifier from the user or equipment, such as a passive RFID or active RFID or other identifier, which may be utilized by the mobile computer to determine what weight as user is lifting, or what shoes a user is running with, or what weapon a user is using, or what type of activity a user is using based on the identifier of the equipment. The mobile computer may analyze the motion capture data locally and display, i.e., show or send information such as a message for example when a threshold is observed in the data, for example when too many G-forces have been registered by a soldier or race car driver, or when not enough motion is occurring (either at the time or based on the patterns of data in the database as discussed below based on the user's typical motion patterns or other user's motion patterns for example.) In other embodiments, once a user has performed a certain amount of motion, a message may be sent to compliance monitor(s), including for example parents, children or elderly, managers, doctors, insurance companies, police, military, or any other entity such as equipment manufacturers. The message may be an SMS message, or email, or tweet or any other type of electronic communication. If the particular embodiment is configured for remote analysis or only remote analysis, then the motion capture data may be sent to the server/database. If the implementation does not utilize a remote database, the analysis on the mobile computer is local. If the implementation includes a remote database, then the analysis may be performed on the mobile computer or server/database or both. Once the database obtains the motion capture data, then the data may be analyzed and a message may be sent from the server/database to compliance personnel or business entities as desired. Embodiments of the invention make use of the data from the mobile computer and/or server for gaming, morphological comparing, compliance, tracking calories burned, work performed, monitoring of children or elderly based on motion or previous motion patterns that vary during the day and night, safety monitoring for troops when G-forces exceed a threshold or motion stops, local use of running, jumping throwing motion capture data for example on a cell phone including virtual reality applications that make use of the user's current and/or previous data or data from other users, or play music or select a play list based on the type of motion a user is performing or data mining. For example if motion is similar to a known player in the database, then that user's playlist may be sent to the user's mobile computer 101. The processing may be performed locally so if the motion is fast, fast music is played and if the motion is slow, then slow music may be played. Any other algorithm for playing music based on the motion of the user is in keeping with the spirit of the invention. Any use of motion capture data obtained from a motion capture element and app on an existing user's mobile computer is in keeping with the spirit of the invention, including using the motion data in virtual reality environments to show relative motion of an avatar of another player using actual motion data from the user in a previous performance or from another user including a historical player for example. Display of information is generally performed via three scenarios, wherein display information is based on the user's motion analysis data or related to the user's piece of equipment and previous data, wherein previous data may be from the same user/equipment or one or more other users/equipment. Under this scenario, a comparison of the current motion analysis data with previous data associated with this user/equipment allows for patterns to be analyzed with an extremely cost effective system having a motion capture sensor and app. Under another scenario, the display of information is a function of the current user's performance, so that the previous data selected from the user or another user/equipment is based on the current user's performance. This enables highly realistic game play, for example a virtual tennis game against a historical player wherein the swings of a user are effectively responded to by the capture motion from a historical player. This type of realistic game play with actual data both current and previously stored data, for example a user playing against an average pattern of a top 10 player in tennis, i.e., the speed of serves, the speed and angle of return shots, for a given input shot of a user makes for game play that is as realistic as is possible. Television images may be for example analyzed to determine swing speeds and types of shots taken by historical players that may no longer be alive to test one's skills against a master, as if the master was still alive and currently playing the user. Compliance and monitoring by the user or a different user may be performed in a third scenario without comparison to the user's previous or other user's previous data wherein the different user does not have access to or own for example the mobile computer. In other words, the mobile phone is associated with the user being monitored and the different user is obtaining information related to the current performance of a user for example wearing a motion capture element, such as a baby, or a diabetes patient.

Figure 1D:
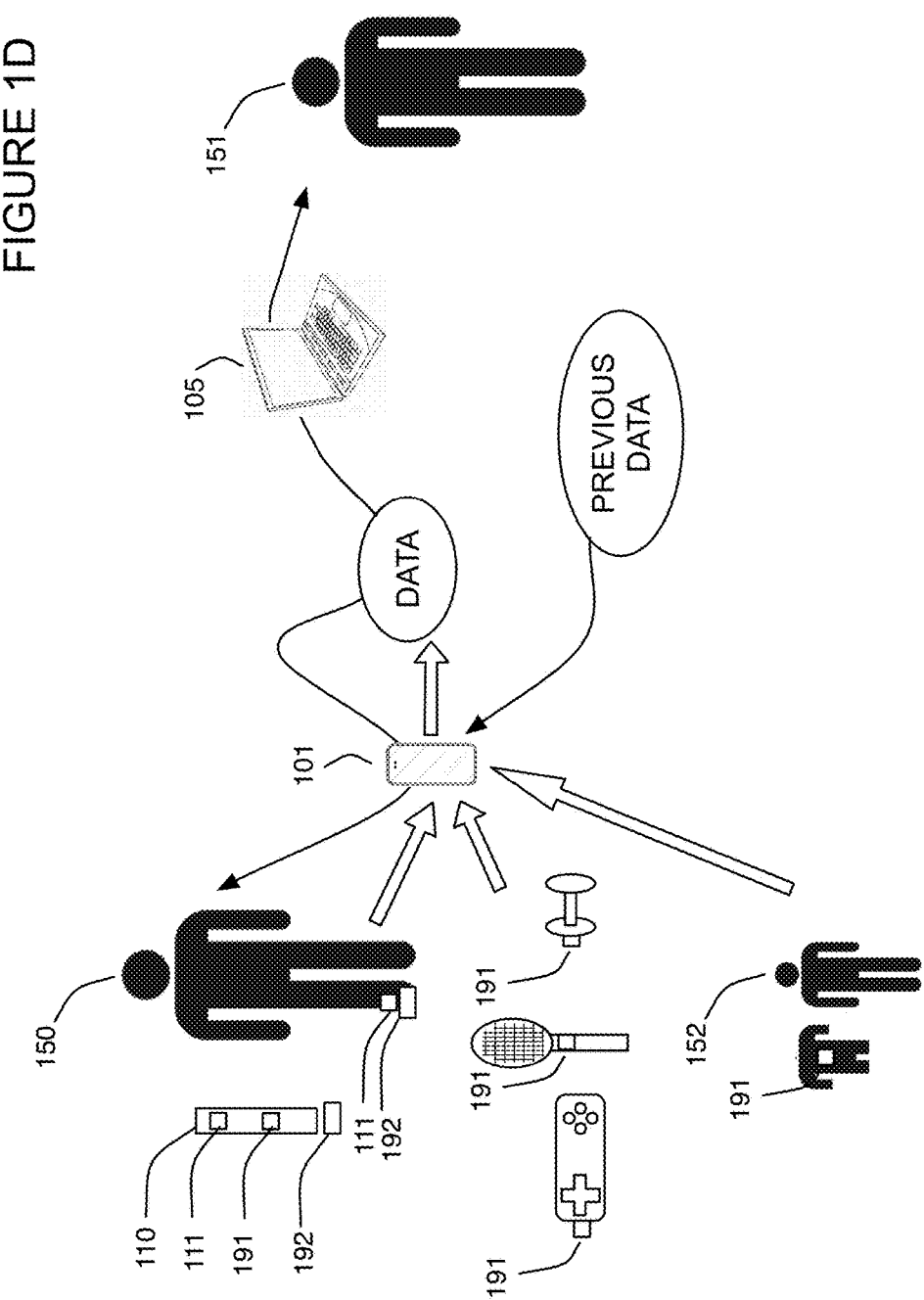
FIG. 1D illustrates a data flow diagram for an embodiment of the system.

FIG. 1D illustrates a data flow diagram for an embodiment of the system. As shown motion capture data is sent from a variety of motion capture elements 111 on many different types of equipment or associated with user 150. The equipment or user may optionally have an identifier 191 that enables the system to associate a value with the motion, i.e., the weight being lifted, the type of racquet being used, the type of electronic device being used, i.e., a game controller or other object such as baby pajamas associated with baby 152. In one or more embodiments, elements 191 in the figure may be replaced or augmented with motion capture elements 111 as one skilled in the art will appreciate. In one or more embodiments of the system, mobile computer 101 receives the motion capture data, for example in event form and for example on an event basis or when requested by mobile computer 101, e.g., after motion capture elements 111 declares that there is data and turns on a receiver for a fix amount of time to field requests so as to not waste power, and if no requests are received, then turn the receiver off for a period of time. Once the data is in mobile computer 101, then the data is analyzed, for example to take raw or event based motion capture data and for example determine items such as average speed, etc., that are more humanly understandable in a concise manner. The data may be stored, shown to the right of mobile computer 101 and then the data may be displayed to user 150, or 151, for example in the form of a monitor or compliance text or email or on a display associated with mobile computer 101 or computer 105. This enables users not associated with the motion capture element and optionally not even the mobile computer potentially to obtain monitor messages, for example saying that the baby is breathing slowly. Under other scenarios, the breathing rate, i.e., the motion of the motion capture element on the baby's pajamas may be compared to previous data related to the baby to determine if the baby is breathing faster than normal, or compared to other baby's previous data to determine if the baby is breathing faster than the average baby. These sophisticated comparisons enable determination of when a baby is becoming ill before known solutions. In gaming scenarios, where the data obtained currently, for example from user 150 or equipment 110, the display of data, for example on virtual reality glasses may make use of the previous data from that user/equipment or another user/equipment to respond to the user's current motion data, i.e., as a function of the user's input. The previous data may be stored anywhere in the system, e.g., in the mobile computer 101, computer 105 or on the server or database 172 (see FIG. 1).

FIG. 2 illustrates an embodiment of the overall modes of the software programmed to execute on the computer of the mobile device, wherein the computer is configured to optionally recognize the motion capture elements, obtain data, analyze the data and display motion analysis data. Mode 201 shows mobile device 101 having display 120 that displays a user with highlighted points on the user and/or piece of equipment. In this mode, each sensor is identified and assigned one by one to a particular area of the user or piece of equipment so as to recognize which sensors correspond to which movements of the user and/or piece of equipment. Mode 202 is the mode where the computer in mobile device obtains data associated with at least one motion capture element as recognized in mode 201. Mode 203 is the mode where the data is analyzed to form motion analysis data and display the motion analysis data optionally in conjunction with at least one image of the user. Mode 204 is the mode where the motion analysis data and optional at least one image of the user is saved, or retrieved to display at a later time. The images may be automatically captured from a second user's mobile device and transferred to the user's mobile device who swung the golf club so that they user's don't have to switch phones while playing to obtain image data for themselves. One algorithm embodiment detects a motion capture element data for a club that is not associated with the user of the video camera based mobile phone and queries nearby mobile devices to determine if they will accept the video. The mobile device of the user who performed the swing may automatically transfer the video so that after the user has swung, the user can look at their own phone and see their image overlaid with motion capture data without having users switch phones to capture video for each other. The motion capture data may be automatically stored in database 172 which for example may be in the form of a social network, in which case the transfer of data (for example a new maximum power score), may be automatically "tweeted" to Internet 171 and/or database 172 to notify everyone connected to the Internet of the new event. The upload of sensor data including any images/video and/or motion capture data may occur whenever a telephonic or other wireless link is available to database 172 for example. I.e., the motion capture sensors may store data until they have a wireless link to mobile computer 101, and mobile computer 101 may also buffer data including any analyzed motion capture data until a link to database 172 is available. Alternatively, the data transfers may occur at defined times, upon events such as a shot occurrence or distance moved by the mobile computer and hence the user, or polled by the database or in any other manner. Once the data is in database 172 it may be data mined as previously discussed.

Figure 3:
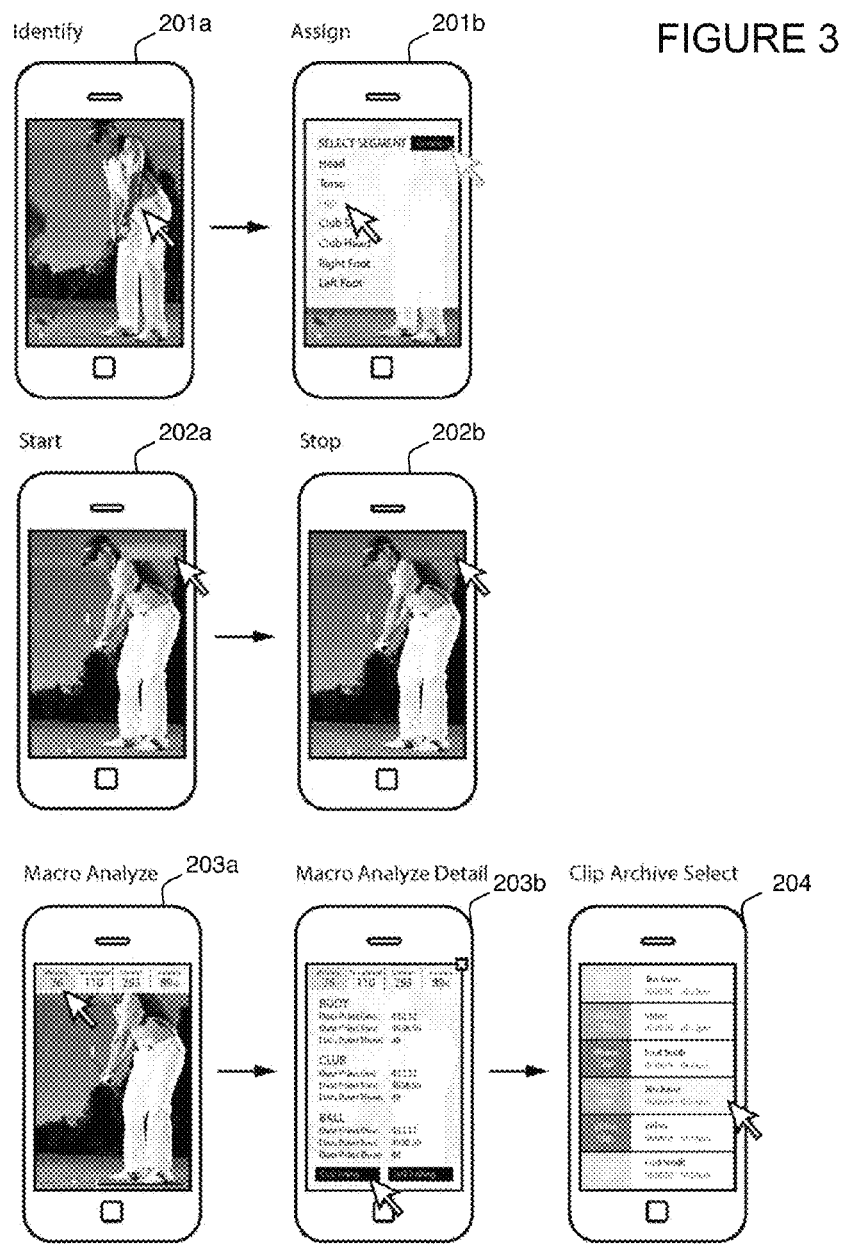
FIG. 3 illustrates displays associated with FIG. 2 in greater detail.

FIG. 3 illustrates displays associated with FIG. 2 in greater detail. Mode 201 includes sub-modes 201*a* where each motion capture element is asserted, moved, switched on or other wise identified. Data and/or metadata associated with the user such as age, height, weight, equipment manufacturer or model number and size may also be input in this screen. Alternatively, website 173 may be utilized to input this data or any other user related data for example. This allows for data mining the data and/or metadata and associated motion capture data later. Owners of database 172 may charge a fee for this service. Sub-mode 201*b* allows for assignment of the motion capture element so asserted to a particular body part of the user, or a location on the piece of equipment. Mode 202 includes sub-modes 202*a* where the computer obtains data associated with at least one motion capture element, either via image capture of one or more motion capture elements implemented as visual markers, or via wireless sensors, or both visual markers and wireless sensors. Mode 203 includes sub-mode 203*a* where main motion analysis data items may be displayed, and sub-mode 203*b* where detailed motion analysis data items may be displayed. Mode 204 shows selection of an archive name to store archive motion capture data, i.e., the motion analysis data and any images of the user. Mode 204 also allows for retrieval of an archived motion capture data by selected a list item on the display of the mobile device. In one or more embodiments, the motion capture archived data may be stored on the mobile device or remotely on computer 105, or in database 172 accessed via network 170 and/or via Internet 171.

Figure 4:
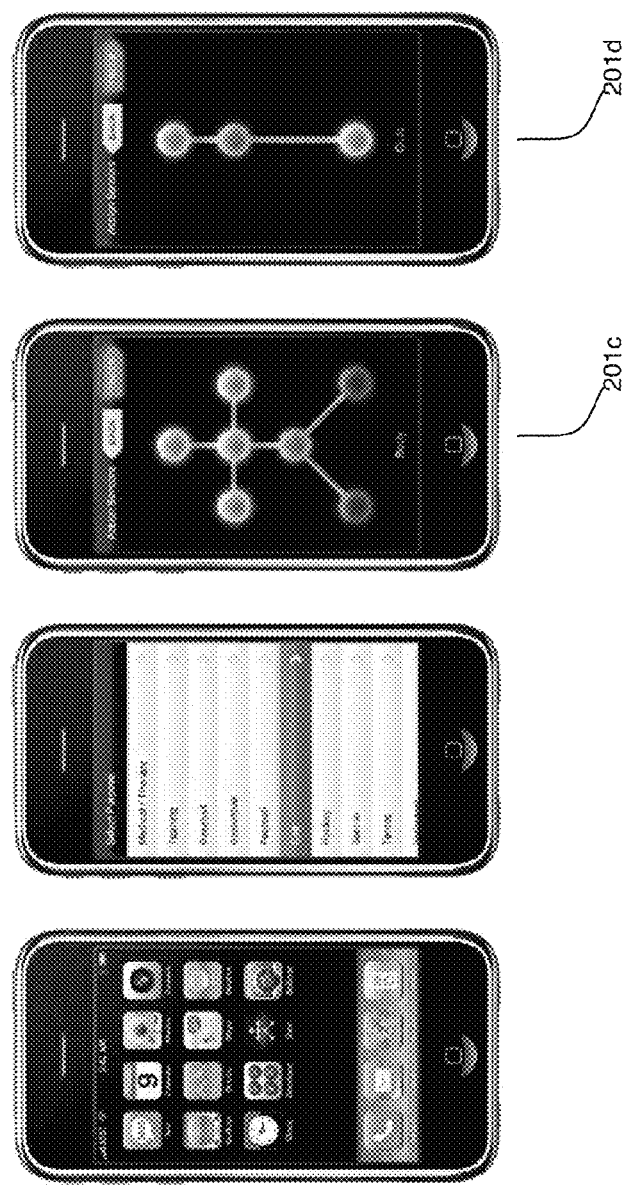
FIG. 4 illustrates and embodiment of the recognition module that is configured to assign particular sensors to particular locations on an athlete and/or on a piece of equipment.

FIG. 4 illustrates and embodiment of the recognition module that is configured to assign particular sensors to particular locations on an athlete and/or on a piece of equipment. In this simplified interface for mode 201, a mobile application is selected from the interface in the far left screen shot that then displays a number of activities or sports that can be motion captured by embodiments of the system. Selecting the desired sport via a finger gesture or any other manner in this display shows sub-mode screen 201*c* that allows for the assignment of sensors to areas of the user's body, and/or sub-mode screen 201*d* that allows for the assignment of sensors to areas on the equipment for the particular sport selected in the second screen from the left in the figure. Automatic determination of the assigned sensor locations is also possible based on analyzing the spatial data obtain from a golf swing. For example by determining the positions, or speed of the various sensors, an automatic assignment may be made, for example by taking the fastest moving component and assigning that to the golf club head, while taking the next fastest component and assigning that component to the hands, etc. Any other technique for automatically assigning sensors to locations of embodiments of the invention is in keeping with the spirit of the invention. In embodiments of the invention that utilize RFID or other identifier mechanism coupled with the golf club, such as a unique identifier per motion capture element for example, the user may enter a golf club number associated with a particular golf club so that the system knows which club is in proximity to the mobile computer or which golf club number for example has been moved through a golf swing. For baseball, the thick end of the bat generally moves faster and travels farther than the handle, and the system can automatically determine which sensor is which by analyzing the speed for example or total distance travelled when the bat is moved in a substantially horizontal plane. This automatic assignment makes the system easy to use and applies to all types of equipment as one skilled in the art will appreciate.

Figure 5:
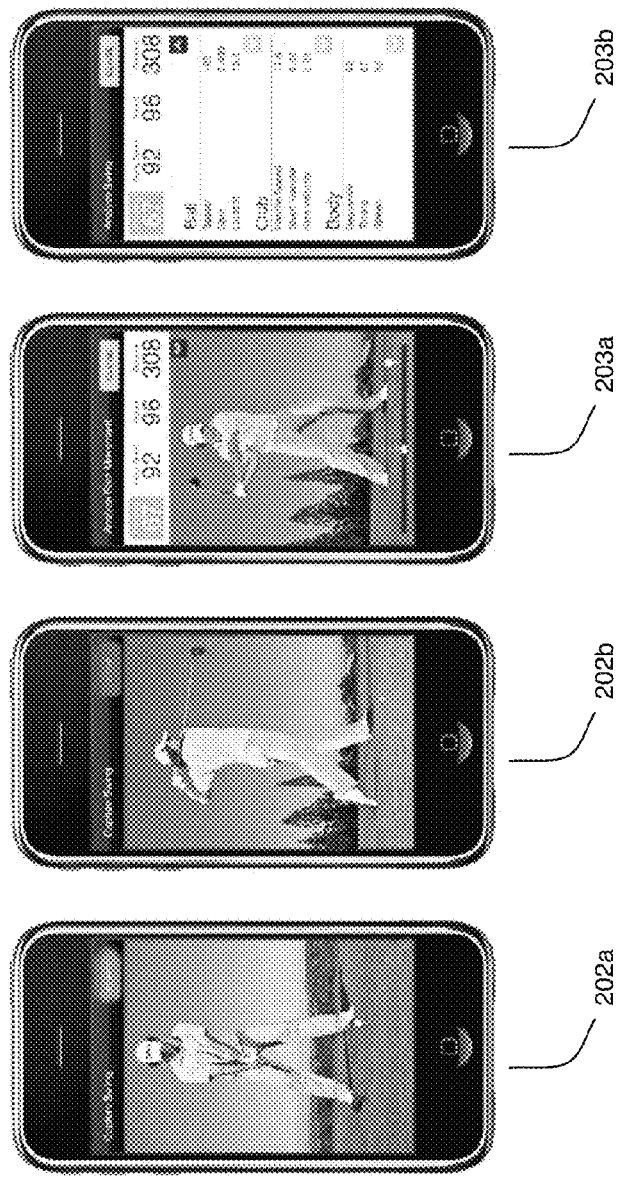
FIG. 5 illustrates an embodiment of the obtain data module that is configured to obtain data from a camera (optionally on the mobile device or obtain through another camera or camera on another mobile device), data from motion capture elements, i.e., any combination of visual markers or sensors as assigned to particular portions of the user's body or piece of equipment. In addition, the figure shows displays data analyzed by the analysis module and generated by the display module to show either the user along with motion analysis data, or with motion analysis data alone.

FIG. 5 illustrates an embodiment of the obtain data module that is configured to obtain data from a camera (optionally on the mobile device or obtain through another camera or camera on another mobile device) through asserting the "start" button on the display. Any other method of initiating the computer within the mobile device to obtain data is in keeping with the spirit of the system including user gestures such as moving the piece of equipment in a particular manner or in any other way. This is shown as sub-mode 202a. When motion data capture is to be terminated, any user gesture may be performed via the display of the mobile device, via the piece of equipment or via audio input to the mobile device for example. Any other method of informing the computer to no longer obtain data is in keeping with the spirit of the system. Sub-mode 203a where main motion analysis data items may be displayed, and sub-mode 203b where detailed motion analysis data items may be displayed are shown with "close" buttons, so that the data can be ignored for example. In addition, a slider in sub-mode 203a allows for precise control of the speed and/or location of the playback so that slow motion analysis may be utilized to better understand the analysis and display of motion analysis data. In addition, the figure shows displays data analyzed by the analysis module and generated by the display module to show either the user along with motion analysis data, or with motion analysis data alone. Double clicking or tapping on a detailed item may optionally display a list of exercises that a user may perform to increase the user's performance.

Figure 6:
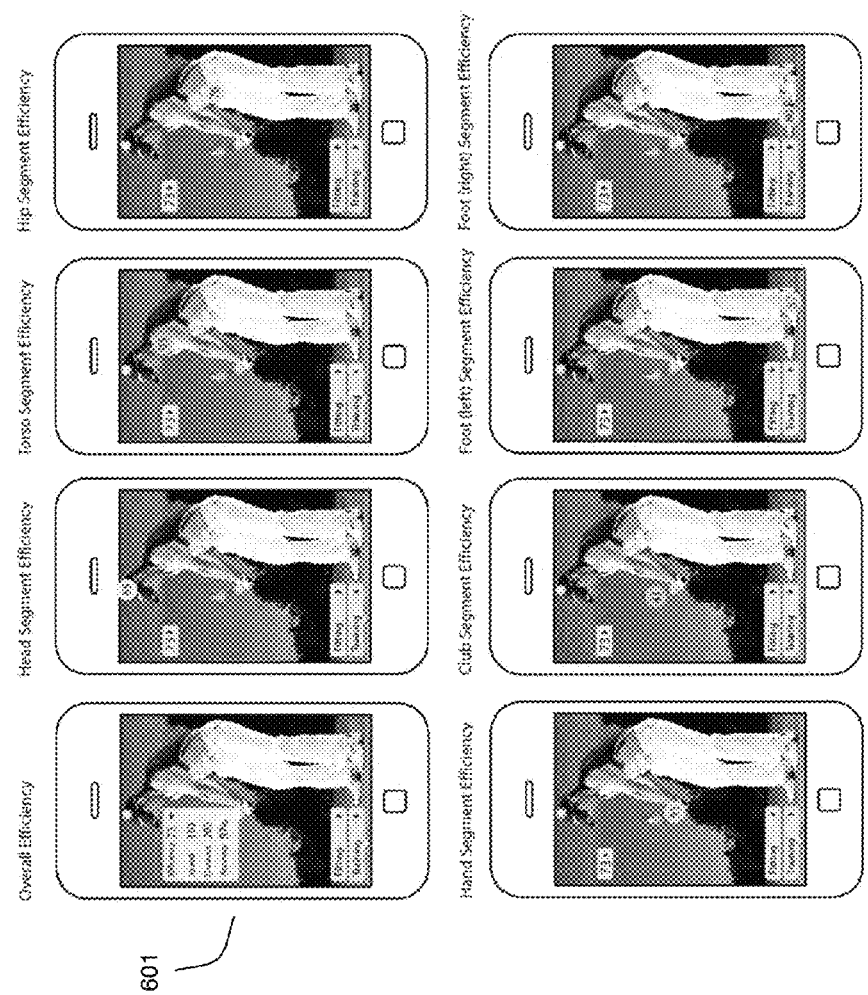
FIG. 6 illustrates a detailed drill down into the motion analysis data to display including overall efficiency, head, torso, hip, hand, club, left and right foot segment efficiencies. Embodiments of the invention thus enable physical training specific to the area that a user needs as determined by the analysis module.

FIG. 6 illustrates a detailed drill down into the motion analysis data to display including overall efficiency, head, torso, hip, hand, club, left and right foot segment efficiencies. Embodiments of the system thus enable physical training specific to the area that a user needs as determined by the analysis module. For example, asserting, double clicking or tapping, or clicking on the "training" button on the bottom of each efficiency screen as shown may display video, audio, or a list of exercises that a user may perform to increase the user's performance specific to that segment. In addition, by asserting the "fitting" button on each segment display, a detailed list of pieces of equipment that may perform better for the user based on the motion analysis data may be viewed. For example, if the user is swing too stiff of a golf club, then the golf club may be taking power out of the swing by slowing down before impacting a golf ball, while a more flexible shaft would speed up before impacting a golf ball. By asserting the "fitting" button, and based on the motion analysis data, for example club head speed or if multiple sensors are fitted on the shaft, then by the flexing of the shaft, then alternate golf clubs may be displayed to the user. The user may then press the purchase button, as will be detailed later, to purchase or custom order equipment that is better suited to the user. The displays shown in FIG. 6 or any of the other figures that display data associated with the user may also include data mining results or comparisons or suggestions or fields for searching and performing data mining. For example, the power factor achieved for a given swing may be compared against average users or professional users and suggest other equipment that may improve performance as per data mining patterns discovered in database 172 and stored for example in table 184.

Figure 7:
FIG. 7 illustrates a close up display of motion analysis data associated with a user, without use of an image associated with a user.

FIG. 7 illustrates a close up display of motion analysis data associated with a user, without use of an image associated with a user. In this close-up of sub-mode 203b, the efficiency, swing speed, release speed, face alignment angle and other quantities associated with the motion analysis data are displayed. Any data that is obtained or that can be analyzed and derived may be displayed. This includes any data previously saved in database 172 or data mined from database 172 for example.

Figure 8:
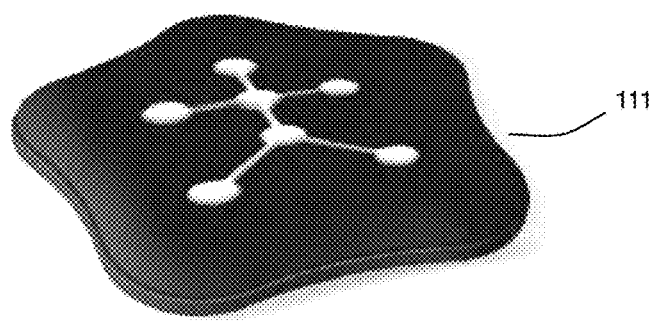
FIG. 8 illustrates an embodiment of the motion capture element that optionally includes a visual marker and/or sensor.

FIG. 8 illustrates an embodiment of the motion capture element that optionally includes a visual marker and/or sensor. One or more embodiments of the sensors are small, for example 12 mm or less in diameter and 4 mm or less thick in one embodiment. In addition, the sensors are inexpensive, lightweight, for example less than 5 grams in one or more embodiments. The sensors may utilize known wireless communications protocols such as BLUETOOTH® with a range of approximately 10 meters for Bluetooth class 2, or 100 meters for Bluetooth class 1. Embodiments of the sensor may sample at 1200 times per second or higher or lower depending on the desired performance requirements. The sensors may be sealed for water resistance or proofing and while some embodiments may be opened, for example to replace a battery held inside the sensor housing. Any other sensor having dimensions or capabilities that allow for measurement of any combination of one or more of orientation, position, velocity and/or acceleration that may couple to a piece of equipment or user may be utilized in one or more embodiments as a motion capture element.

Figure 9:
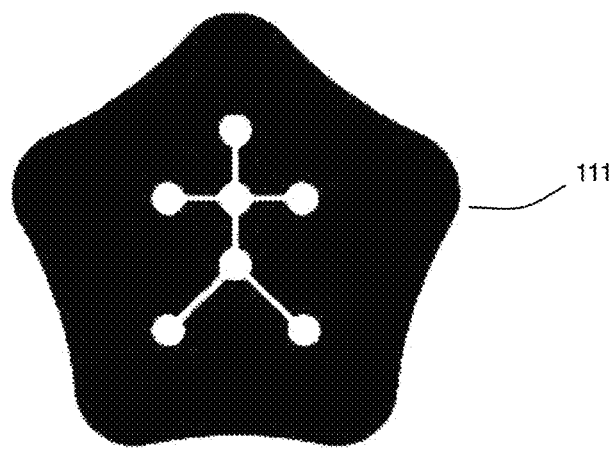
FIG. 9 illustrates a front view of FIG. 8.

FIG. 9 illustrates a front view of FIG. 8. In this figure, the visual marker is shown from above and signifies an instrumented user. The contrast between black and white allows for ease of capture.

FIG. 10 illustrates an embodiment of motion capture element 111 implemented with a single white circle on a black passive marker and gray scale images thereof to show how the marker can be tracked by obtaining an image and searching for a luminance change from black to white as shown at point 1001. Any other image processing algorithm may be utilized to find an embodiment of the motion capture element within an image as one skilled in the art will recognize, for example based on a color difference or gradient detected in an image in the area of an embodiment of motion capture element 111.

Figure 38:
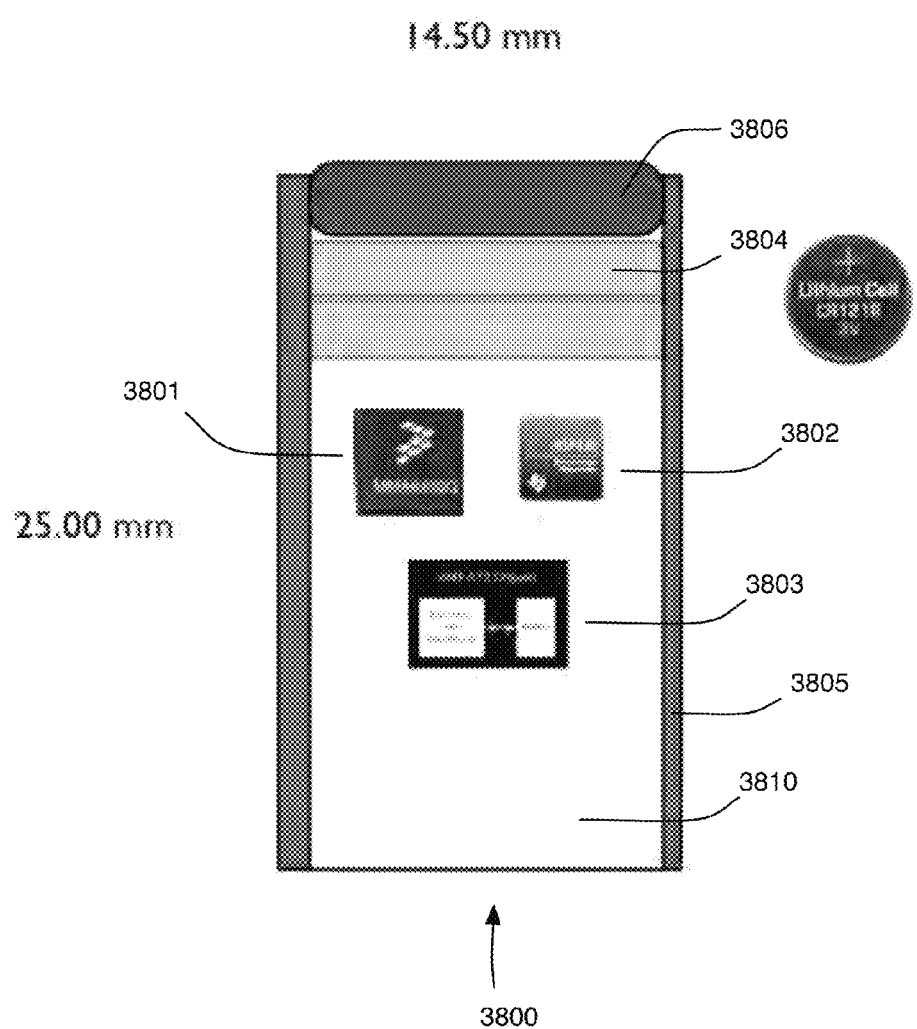
FIG. 38 shows elements of an embodiment of the motion capture element configured to fit into the end of a golf shaft.

FIG. 11 illustrates a hardware implementation of the sensor portion of a motion capture element implemented as a wireless inertial measurement unit, and an embodiment as configured to couple with a weight port of a golf club for example. Printed circuit board (PCB) may be utilized to hold the various components of the sensor including any orientation, position, velocity and/or accelerometers. Hole 1101 may be utilized as a screw hole or other coupling point for coupling motion capture element 111 to a piece of equipment, such as into a weight port of a golf club. Alternatively, threads at location 1102 or at location 1103 may be utilized to screw motion capture element 111 onto the piece of equipment. Any other method of coupling motion capture element to a piece of equipment or user is in keeping with the spirit of the invention. Embodiments of the invention may also be placed near the head of a golf club, in the handle of a golf club, or in any other piece of equipment. When placing an embodiment of the invention near the golf club head or handle, an adapter may be utilized so as to fit the apparatus to the specific make and/or model of the golf club. Each manufacturer has multiple types of weight port sizes, locations and shapes and any adapter that can for example screw into a weight port hole and also fit threads at location 1102 may be utilized as an adapter. For handles, any tube size for a given make or model of a club may be utilized as an adapter so long as it allows the components of embodiments of the invention to fit inside the golf club and withstand the forces involved with a golf club swing. See also FIGS. 38-42. In a wired embodiment of the golf club, apparatus 111 for example as mounted near a golf club head may electrically couple to another apparatus 3800 as shown in FIG. 38 so as to allow wired recharging of both apparatus in one golf club simultaneously.

Figure 11A:
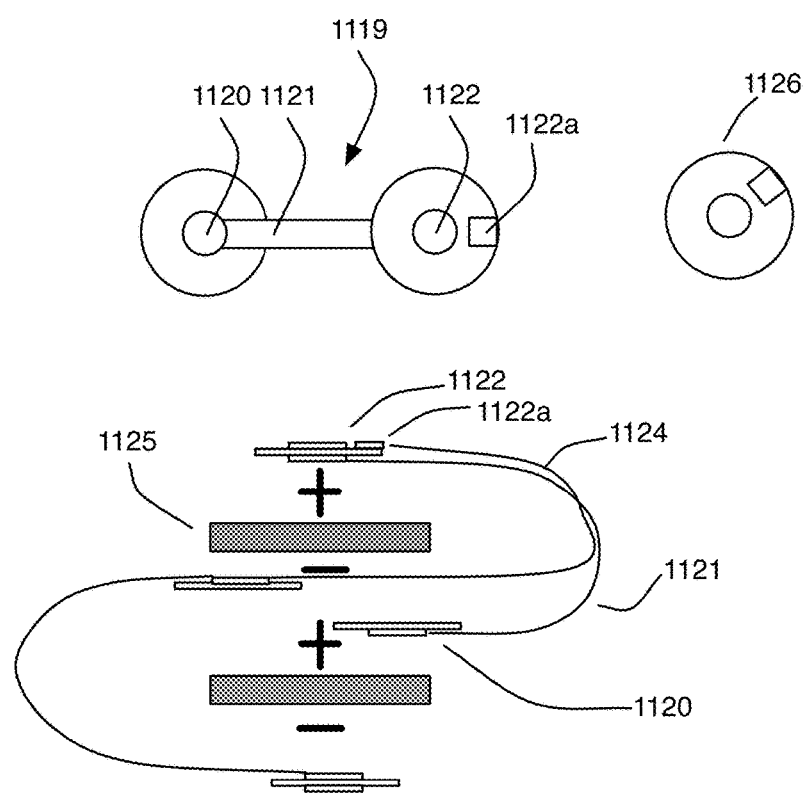
FIG. 11A illustrates and embodiment of a multiple battery arrangement wherein a plurality of batteries may be coupled in parallel and still be arranged physically on top of one another.

FIG. 11A illustrates and embodiment of a multiple battery arrangement wherein a plurality of batteries may be coupled in parallel and still be arranged physically on top of one another. Batteries 1125 (of which two are shown from side view on top of one another) as shown in the lower portion of the figure are coupled in parallel using battery coupler 1119. Battery coupler 1119 includes a pass-thru connector 1122 on each side of an insulating circular element that is coupled with an insulated conductor 1121 to another insulating circular element having a single sided connector 1120. Optional opposing polarity pad 1122a may also be located on the first circular element to allow for rotating cap 1126 to make contact with elements 1122 and 1122a when rotated into the on position thereby making contact with both elements. As shown in the lower part of the figure, two battery couplers 1119 are wrapped around respective batteries wherein the pass-thru connectors are on opposing sides of the pair of batteries, while the single sided connectors 1120 are situated pointing away from one another to insulate the respective poles from one another in the inner portion of the battery pair. Wire 1124 may be utilized to provide a contact to element 1122a if desired, in which case the bottom pass thru contact of shown in the bottom of the figure may be implemented as one sided, i.e., if both positive and negative are to brought to the top of the stack at 1122 and 1122a respectively. This enables standard coin batteries to be utilized in parallel to double, or multiply the capacity by N if more battery couplers 1119 are utilized, so that N batteries in parallel for example.

Figure 11B:
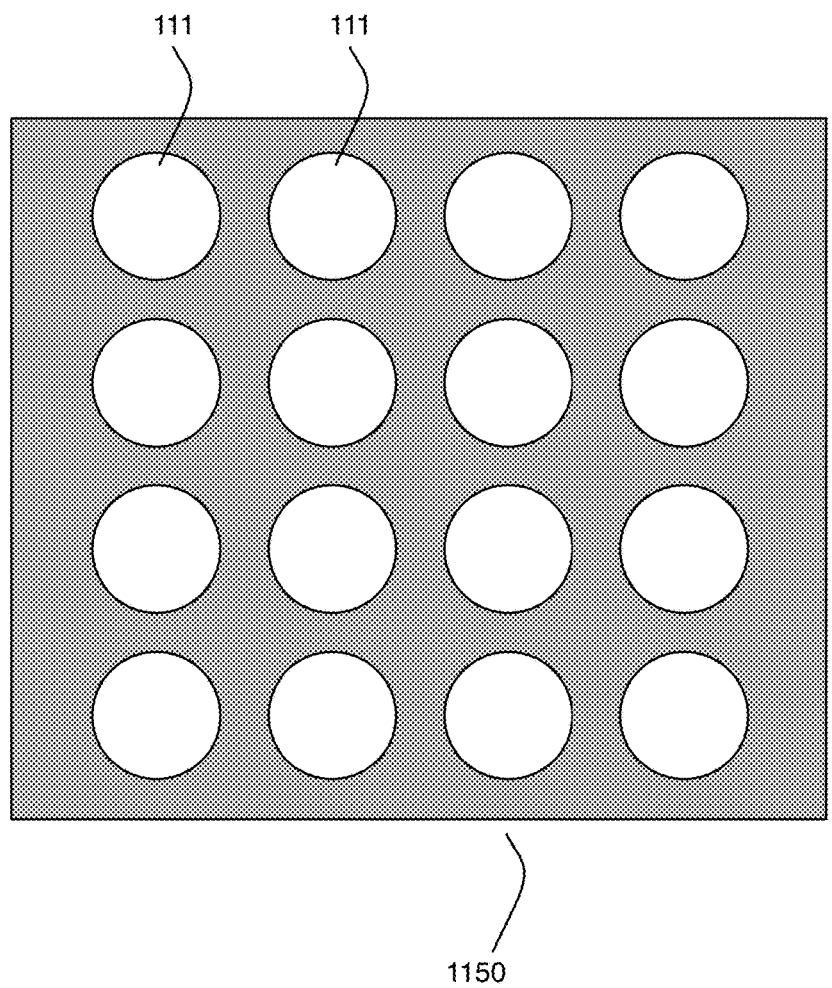
FIG. 11B illustrates and embodiment of a multiple motion capture element calibration element for calibrating multiple motion capture elements at once.

FIG. 11B illustrates and embodiment of a multiple motion capture element calibration element for calibrating multiple motion capture elements at once. By placing multiple motion capture elements on the calibration element 1150 and moving or orienting the elements for example on a hexapod in a known manner, then all of the motion capture elements may be calibrated at once. In this manner, the electrical functional as well as the calibration of the various sensors may be performed rapidly. A hexapod is but one embodiment of a test bed that may be utilized to calibrate motion related parameters on multiple motion capture elements at once. Any other method of positioning, moving, accelerating or otherwise orienting more than one motion capture element at once is in keeping with the spirit of the invention.

Figure 12:
FIG. 12 illustrates an embodiment of the motion capture element as configured to couple with different golf club types and a shoe.

FIG. 12 illustrates an embodiment of the motion capture element as configured to couple with different golf club types and a shoe. As shown in the leftmost figure, motion capture element 111 can couple directly to a piece of equipment such as a golf club in the rear portion of the club head. As the second from left figure illustrates, motion capture element 111 may couple onto the bottom of a piece of equipment, such as a golf putter. In addition, as the third figure from the left illustrates, motion capture element 111 may couple into the weight port of a piece of equipment, such as a driver. Furthermore, motion capture element may couple with a piece of equipment that is worn by the user, effectively coupling with the user as shown in the rightmost figure.

Figure 13:
FIG. 13 illustrates a close-up of the shoe of FIG. 12 along with a pressure map of a shoe configured with a pressure matt inside the shoe configured to output pressure per particular areas of the shoe.

FIG. 13 illustrates a close-up of the shoe of FIG. 12 along with a pressure map of a shoe configured with a pressure matt inside the shoe configured to output pressure per particular areas of the shoe. In this embodiment, motion capture element may also interface to a pressure sensing mat capable of producing pressure map 1301 from inside of the shoe and relay the pressure information to the mobile device for analysis. Alternatively, pressure sensors may be placed through the shoe, for example in a grid, to provide weight bearing information to the mobile device, for example wirelessly via the motion capture element. Each pressure sensor may couple to a transceiver or contain its own transceiver, or couple via wires or wirelessly to the motion capture element in order to transmit pressure data, for example to display on display 120. By color coding the map and displaying the map on display 120, a color graphic rating is thus obtained, which may include numerical ratings of the pressure signature when compared to saved pressure maps which resulted in good swings for example.

Figure 14:
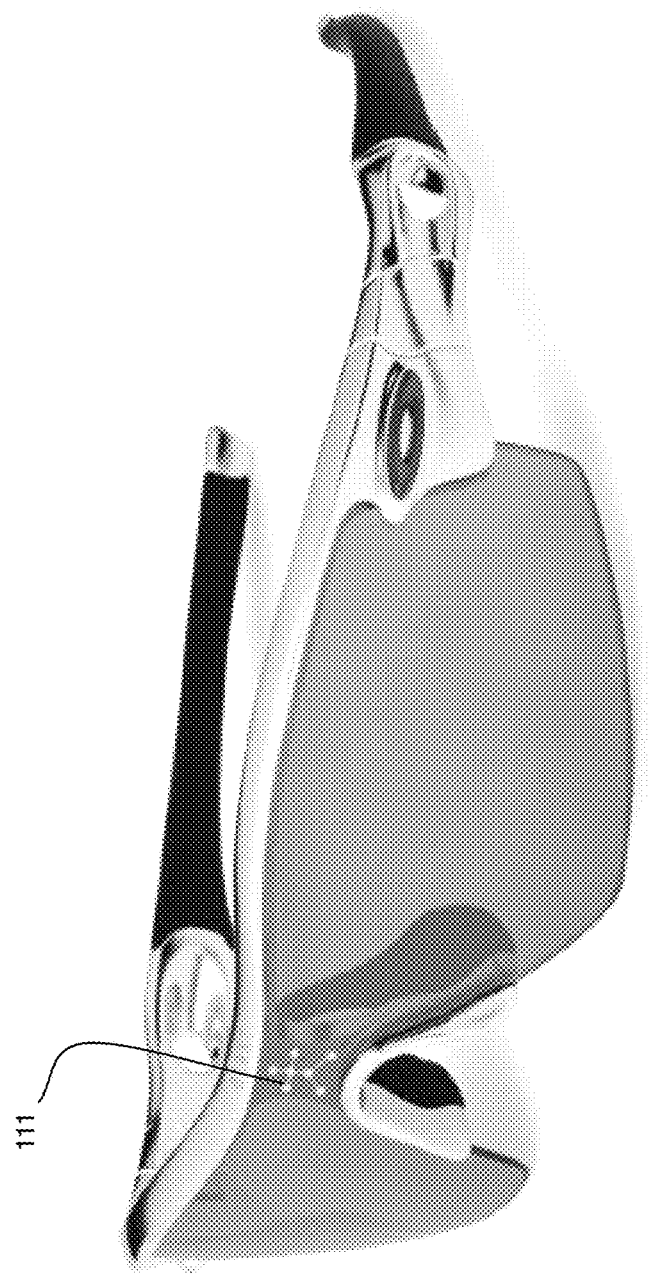
FIG. 14 illustrates an embodiment of sunglasses configured with an embodiment of the motion capture element.

FIG. 14 illustrates an embodiment of sunglasses configured with a motion capture element. In addition, the sunglasses may also include a video viewing device that may be utilized for display 120 so that the user may watch images of the user with motion analysis data via the sunglasses. In this manner, any computer 160, 105, or any other computer coupled to network 170 or Internet 171 may be utilized to obtain data and analyze data so that the resulting motion analysis data may be displayed on the sunglasses, for example for virtual reality and/or augmented virtual reality display. Viewing past performance data in the form of avatars that move according to motion capture data held in database 172 for example enables a user to view relative performance, i.e., a user would see a faster user's avatar running in front of the current user for example, or to play a game, i.e., tennis for example with an avatar of another user or the given user moving according to motion capture data in database 172. Playing games using actual stored motion capture data provides the most realistic virtual reality possible.

Figure 15:
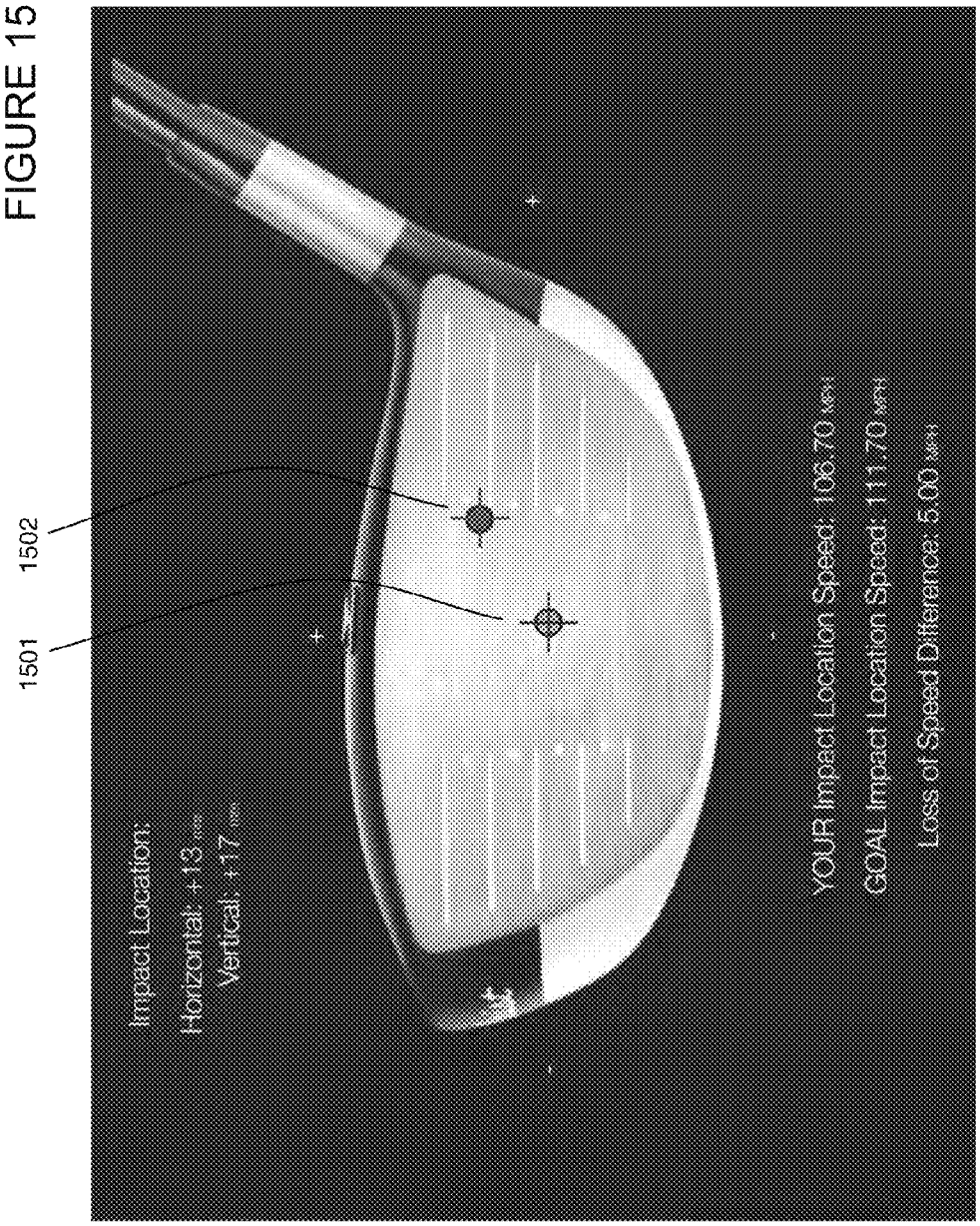
FIG. 15 illustrates an embodiment of a display that depicts the location of a golf ball strike as determined by the oscillations in the golf club face during and/or after the golf club impacts a golf ball.

FIG. 15 illustrates an embodiment of a display that depicts the location of a golf ball strike as determined by the oscillations in the golf club face during and/or after the golf club impacts a golf ball. In one or more embodiments of the invention, if the golf ball impacts the club at location 1501, then a particular frequency response is obtained via orientation or velocity sensors in motion capture element 111 that is coupled with the club shown. If the golf ball impacts the club at location 1502, then a distinct frequency response is obtained via the motion capture element 111 coupled to the club. One embodiment for determining where a ball impacts a club involves recording impacts from a variety of locations at a range of speeds and using the resulting frequency responses to determine which one is the closest to the impact detected. Impacts that occur high or low on the club face tend to produce a vertical axis oscillation of greater amplitude than impacts that occur at location 1501. Impacts that occur closer to the shaft tend to produce lower amplitude oscillations in the horizontal axis than impacts that occur further from the shaft. Hence, another method for determining impact is to form a ratio of the amplitude of horizontal to vertical axis frequency amplitude and then search for the closest match from a saved set of impact frequency responses and retrieve the x and y locations on the club face where the closest match has occurred. In another embodiment of the system, a series of impacts is recording at the center of the club and at 4 points away from the center along the positive x axis, (away from the shaft), positive z axis (above the center point of the face), negative x axis (near the shaft) and negative z axis (below the center point of the face) wherein the motion capture element transmits x, y and z velocities associated with the impact. The velocities are converted into the frequency domain and saved. Then, when determining an impact location for a test swing, an interpolation between the impact in question and the center point and 4 other points is performed to determine the location of the impact. Any other method of determining the impact location that does not require other sensors besides the motion capture element coupled to the club is in keeping with the spirit of the invention.

Figure 16:
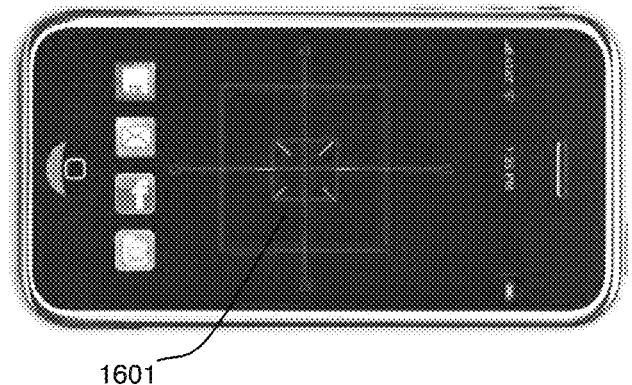
FIG. 16 illustrates a camera alignment tool as utilized with embodiments of the system to create normalized images for capture data mining.
Figure 17:
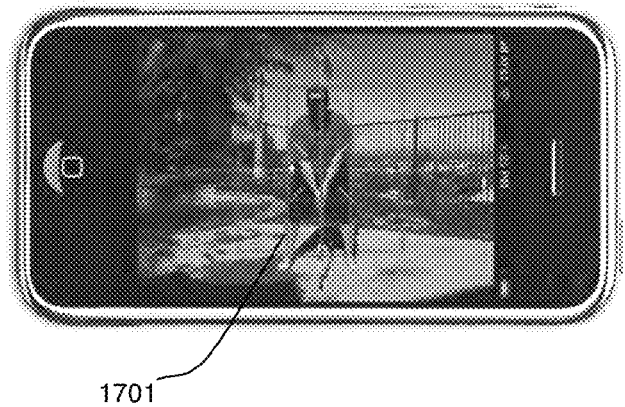
FIG. 17 illustrates a balance box and center alignment line to aid in centering a user to obtain image data.
Figure 18:
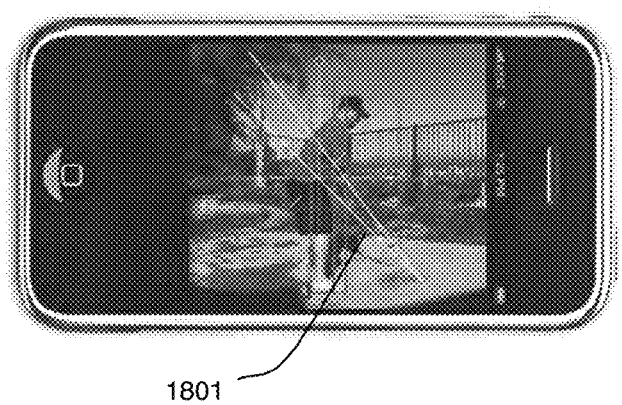
FIG. 18 illustrates a balance box and center alignment line, along with primary and secondary shaft lines to aid in centering and analyzing images of the user.

FIG. 16 illustrates a camera alignment tool as utilized with embodiments of the system to create normalized images for capture data mining. In this figure, level lines 1601 are shown that for example become brighter when the mobile device is level. Any other manner of displaying that the mobile device is level may also be utilized. Icons on the left side of the screen show that the motion capture data and images may be saved, emailed, or sent to popular social networking sites such as FACEBOOK® and TWITTER®. FIG. 17 illustrates a balance box and center alignment line to aid in centering a user to obtain image data. FIG. 18 illustrates a balance box and center alignment line, along with primary and secondary shaft lines to aid in centering and analyzing images of the user for use in capturing data from the side of the user. Once the user is centered, the computer may obtain data and images that are normalized to the horizontal plane.

Figure 19:
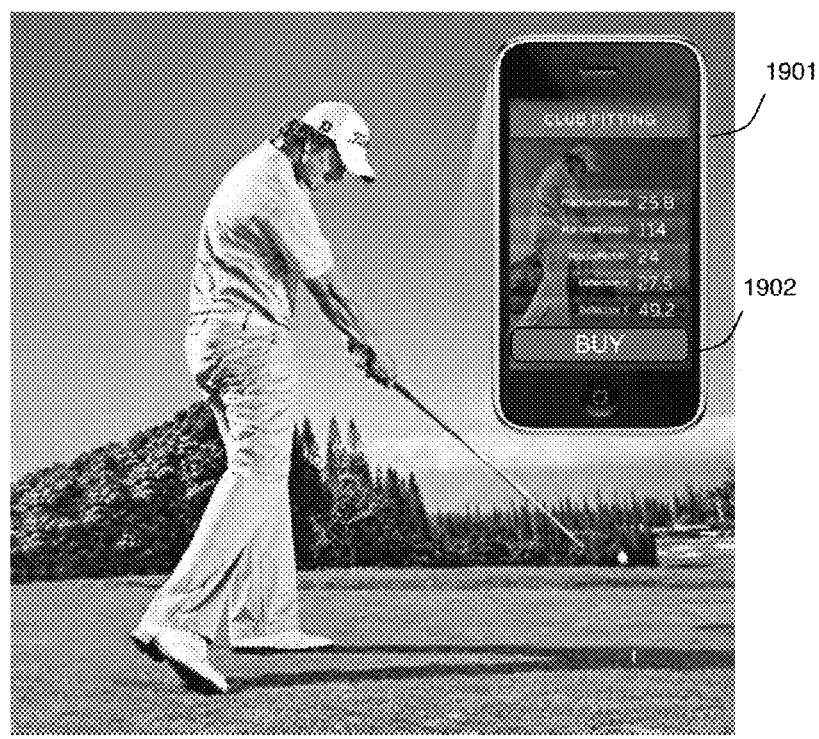
FIG. 19 illustrates an embodiment of the display configured to aid in club fitting for a user, wherein a user may test multiple clubs and wherein the display shows motion analysis data. For embodiments of the invention may be utilized to obtain sensor data that is utilized for purchase and order fulfillment options, buttons such as "purchase" and "customer order" may be utilized.

FIG. 19 illustrates an embodiment of the display configured to aid in club fitting for a user, wherein a user may test multiple clubs and wherein the display shows motion analysis data. For embodiments of the system that include purchase and order fulfillment options, buttons such as "purchase" and "customer order" may be utilized. Alternatively, a "buy" button 1902 may be shown in "club fitting" mode 1901 that enables a user to buy or custom order a custom club that the user is working with. In one or more embodiments of the invention the equipment identifier may be sent over Internet 171 to an Internet based drop shipper (or via website 173 for a salesperson to receive and communicate with the user, or in any other manner as one skilled in the art will appreciate including but not limited to text messaging, emails or phone calls to a sales person directly from the mobile computer with telephonic interface) along with user information for example on mobile computer 101 or in table 180 of FIG. 1B to ship the equipment to the address associated with the user. Table 180 may also include credit card information or other payment information for example.

Figure 20:
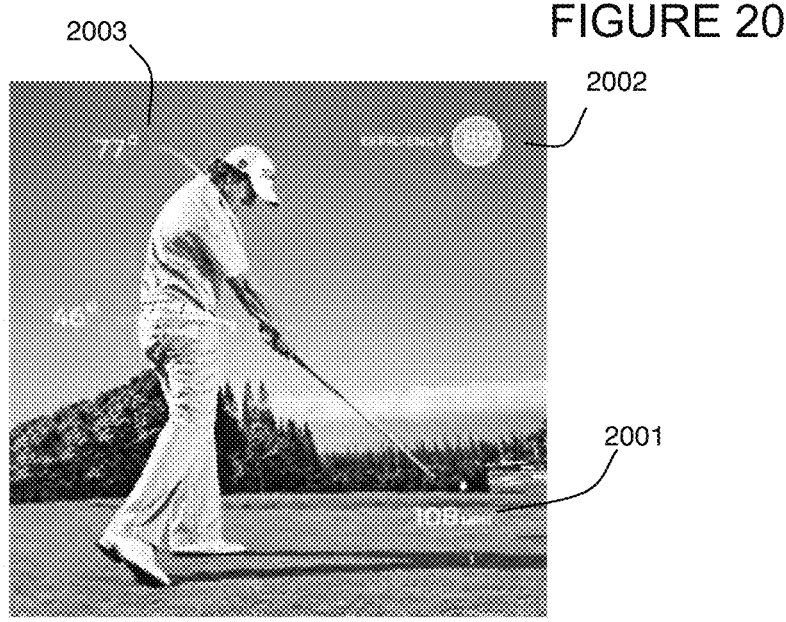
FIG. 20 illustrates an embodiment of the display configured to display motion analysis data along with the user, some of which is overlaid onto the user to aid in understanding the motion analysis data in a more human understandable format. In addition, motion analysis data associated with the user can be shown numerically as shown for example as "efficiency" of the swing, and the velocity of the swing.

FIG. 20 illustrates an embodiment of the display configured to display motion analysis data along with the user, some of which is overlaid onto the user to aid in understanding the motion analysis data in a more human understandable format. For example, rotation rings 2003 may be shown overlaid on one or more images of the user to shown the angle of the axis of rotation of portions of the user's body, such as shoulders and hips. In addition, motion analysis data associated with the user can be shown numerically as shown for example as "efficiency" of the swing 2002, and velocity of the swing 2001. The motion capture data and images may be saved to database 172 and later utilized to play a game against another player for example on a virtual reality golf course. The player may be a historical player whose performance data has been analyzed and stored in the database for later game playing for example.

Figure 21:
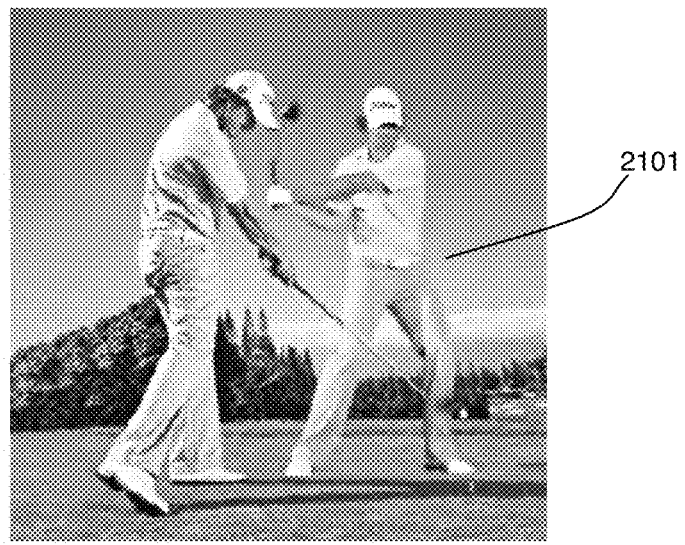
FIG. 21 illustrates an embodiment of the system configured to display a user from multiple angles when multiple cameras are available. One or more embodiments of the system may show one image of the user at a time in slow motion as the user moves, while changing the angle of the view of the user in normal time, which is known as BULLET TIME (11).

FIG. 21 illustrates an embodiment of the system configured to display a user from multiple angles 2101 when multiple cameras are available. Any algorithm that may process images to eliminate backgrounds for example may be utilized to show multiple instances of the user on one background. Alternatively, one or more embodiments of the system may show one image of the user at a time in slow motion as the user moves, while changing the angle of the view of the user in normal time, which is known as BULLET TIME®.

Figure 22:
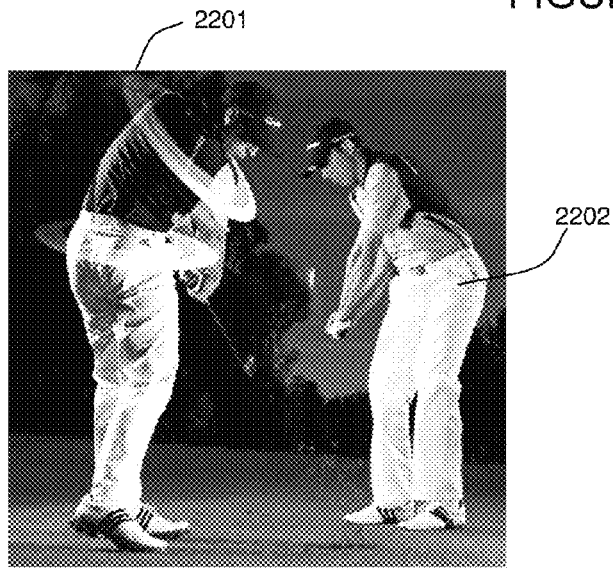
FIG. 22 illustrates another embodiment of the multi-angle display as is also shown in FIG. 21 wherein this figure also includes three-dimensional overlay graphics to aid in understanding the motion analysis data in a more human understandable manner.

FIG. 22 illustrates another embodiment of the multi-angle display as is also shown in FIG. 21. This figure also includes three-dimensional overlay graphics 2201 to aid in understanding the motion analysis data in a more human understandable manner. Second instance of the user 2202 may or may not be shown with the same overlay from a different angle.

Figure 23:
FIG. 23 shows an embodiment of the system configured to display motion analysis data on a mobile computer, personal computer, IPAD® or any other computer with a display device large enough to display the desired data.

FIG. 23 shows an embodiment of the system configured to display motion analysis data on a mobile computer, personal computer, IPAD® or any other computer with a display device large enough to display the desired data.

In any embodiments detailed herein, efficiency may be calculated in a variety of ways and displayed. For embodiments of the invention that utilize one motion capture element, then the motion capture element associated with the club head may be utilized to calculate the efficiency. In one or more embodiments of the invention, efficiency may be calculated as:

$$\text{Efficiency} = (90 - \text{angle of club face with respect to direction of travel}) * V_c/V_{max}$$

Figure 24:
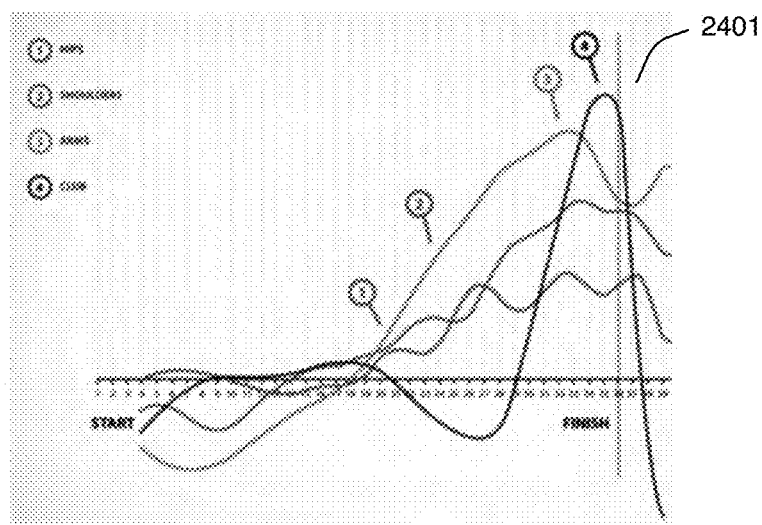
FIG. 24 illustrates a timeline display of motion analysis data that shows multiple sensor angular velocities in reference to the world or for example to a portion of the piece of equipment or object to hit or a virtual spine or a boney landmark, as obtained from sensors on a user and/or on a piece of equipment.
Figure 25:
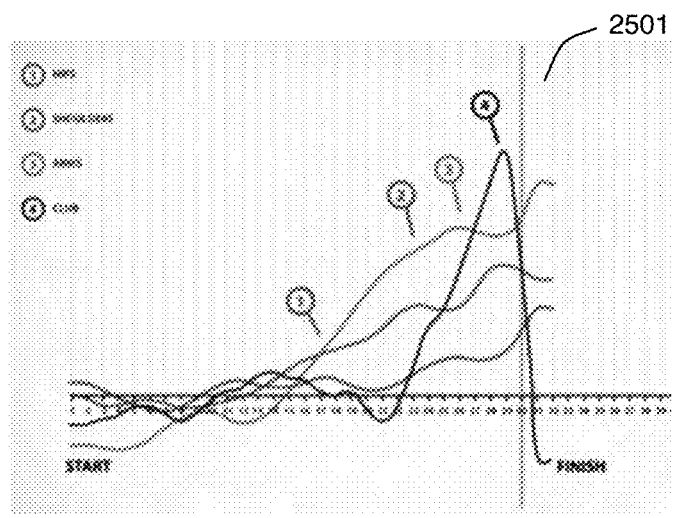
FIG. 25 illustrates a timeline display of motion analysis data that shows multiple sensor angular speeds obtained from multiple sensors on a second user and on a piece of equipment. Efficient movement pattern of body segments know as a kinetic chain and of kinematic segmental sequencing.

As more sensors are added further from the piece of equipment, such as in this case a club, the more refined the efficiency calculation may be. FIG. 24 illustrates a timeline display of motion analysis data that shows multiple sensor angular speeds obtained from multiple sensors on a user and on a piece of equipment. FIG. 25 illustrates a timeline display of angular speed of a second user. One or more embodiments of the system may calculate an efficiency based on relative times of the peaks of the hips, shoulders, arms and club for example. In one or more embodiments of the invention utilizing more than one motion capture element, for example on the handle and club head, the angular velocity Wa of the handle is divided by the angular velocity We of the club head to calculate efficiency with more information. By obtaining a large number of timelines from various professional athletes and determining average amplitudes of angular velocities of various body parts and/or timings, then more refined versions of the efficiency equation may be created and utilized.

$$\text{Efficiency} = (90 - \text{angle of club face with respect to direction of travel}) * V_c/V_{max} * W_a/W_e * 1.2$$

Figure 26:
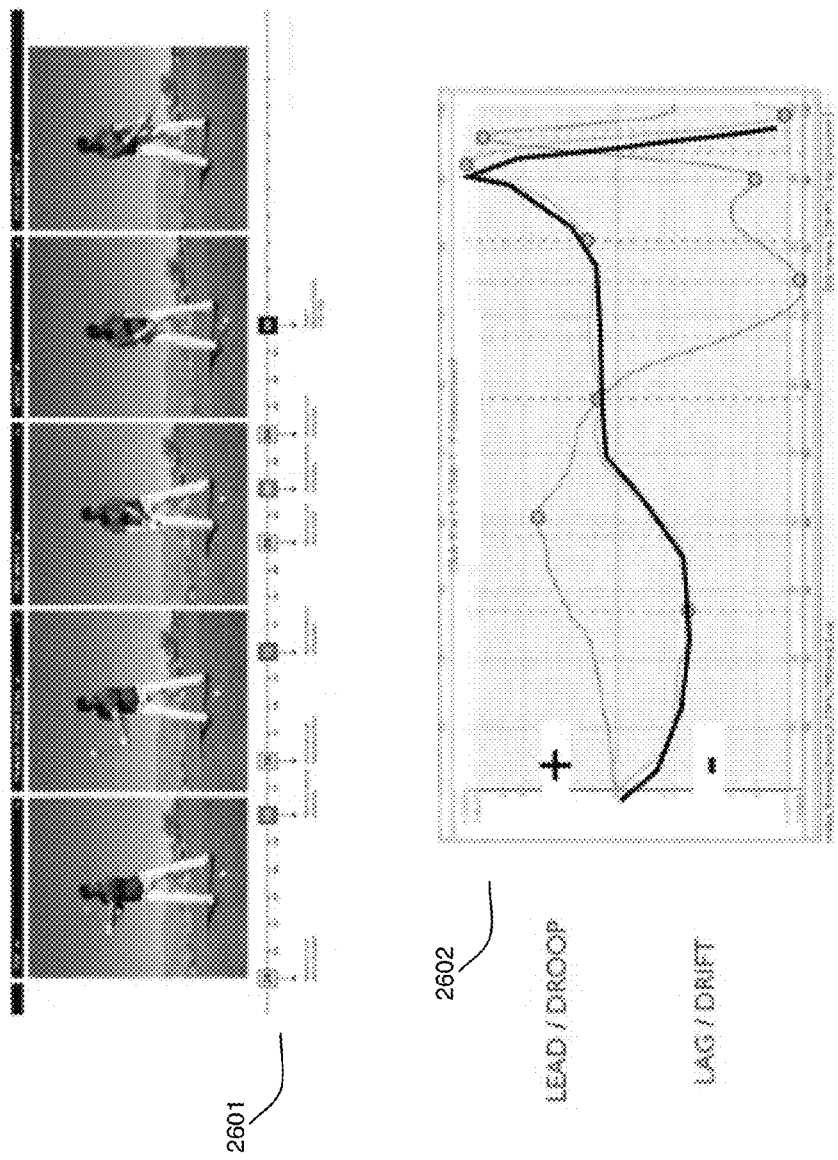
FIG. 26 illustrates a timeline display of a user along with peak and minimum angular speeds along the timeline shown as events along the time line instead of as Y-axis data as shown in FIGS. 24 and 25. In addition, a graph showing the lead and lag of the golf club along with the droop and drift of the golf club is shown in the bottom display wherein these values determine how much the golf club shaft is bending in two axes as plotted against time.

FIG. 26 illustrates a timeline display of a user along with peak and minimum angular speeds along the timeline shown as events along the time line instead of as Y-axis data as shown in FIGS. 24 and 25. In this unique view, the points in time where the peaks of the graphs of FIGS. 24 and 25 are shown as colored boxes that correspond to the colors of the graphs in FIGS. 24 and 25, yet in a more human understandable format that shows the relative timing of the peaks. In addition, at the bottom of FIG. 26 a graph showing the lead and lag of the golf club along with the droop and drift of the golf club is shown wherein these values determine how much the golf club shaft is bending in two axes as plotted against time.

One or more embodiments of the system may analyze the peaks and/or timing of the peaks in order to determine a list of exercises to provide to a user to improve the mechanics of the user. For example, if the arms are rotating too late or with not enough speed, a list can be provided to the user such as:

TABLE 1

| Arm Speed | Exercise |
| --- | --- |
| 1000-1500 degrees/sec | Impact Bag Drawbacks |
| 1501-1750 degrees/sec | Drawbacks |
| 1751-2000 degrees/sec | No drills |

The list of exercises may include any exercises for any body part and may displayed on display 120. For example, by asserting the "Training" button on the displays shown in FIG. 6, a corresponding body part list of exercises may be displayed on display 120.

Figure 27:
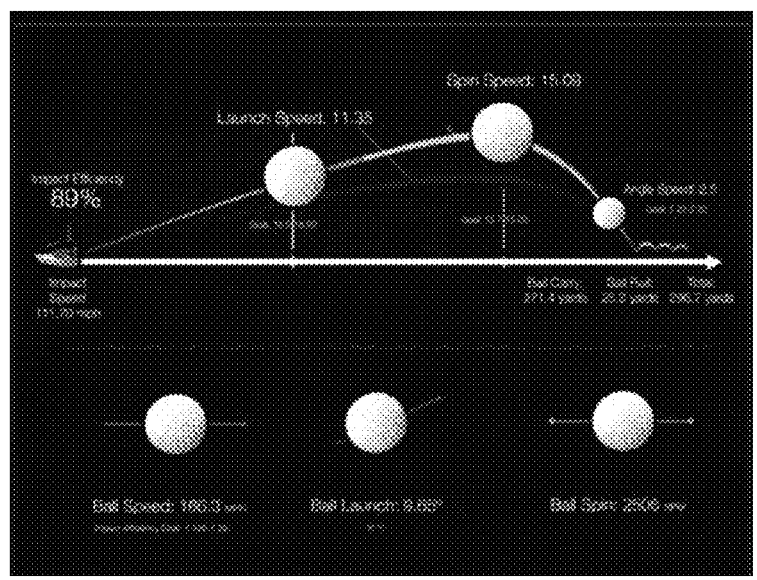
FIG. 27 illustrates a display of the calculated flight path of a ball based on the motion analysis data wherein the display is associated with any type of computer, personal computer, IPAD® or any other type of display capable of displaying images.
Figure 28:
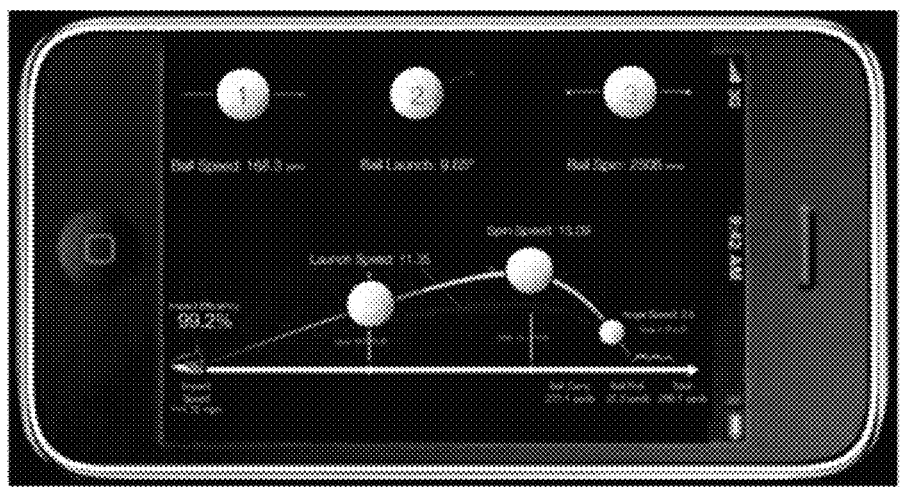
FIG. 28 illustrates a display of the calculated flight path of a ball based on motion analysis data wherein the display is coupled with a mobile device.

FIG. 27 illustrates a display of the calculated flight path 2701 of a ball based on the motion analysis data wherein the display is associated with any type of computer, personal computer, IPAD® or any other type of display capable of displaying images. FIG. 28 illustrates a display of the calculated flight path 2801 of a ball based on motion analysis data wherein the display is coupled with a mobile device. After a swing of a golf club, and based on the club head speed as determined by motion capture element 111, the loft of the club and the angle at which the club strikes the ball (meaning that there is another motion capture element in the handle or near the hands of the user), a flight path may be calculated and displayed. Any model may be utilized as is known in the art to calculate the trajectory based on the club velocity as measure via motion capture element 111, one such model is described in a paper by MacDonald and Hanzely, "The physics of the drive in golf", Am. J. Phys 59 (3) 213-218 (1991). In addition, the actual distances calculated and store in the database, for example as differences between locations of shots for example in table 183 in database 172 may be used to verify or refine the model and may take into account the type of equipment, club and ball for example utilized to refine the model, for example with regression analysis, or in any other manner. See FIG. 37 for one embodiment of the equation used to calculate the accelerations in the x, y and z axes wherein:

x=laterally sideways (right is positive, left is negative)
y=down the fairway (always positive)
z=vertically upwards (up is positive, down is negative)
B=a constant dependent on the conditions of the air, an appropriate value=0.00512
u=vector of relative velocity between the ball and the air (i.e. wind), $u=v-v_w$
Cd=coefficient of drag which depends on the speed and spin of the ball
Cl=coefficient of drag which depends on the speed and spin of the ball
a=the angle between the vertical and the axis of rotation of the spinning ball
g=the acceleration due to gravity=32.16 ft/s2

Figure 29:
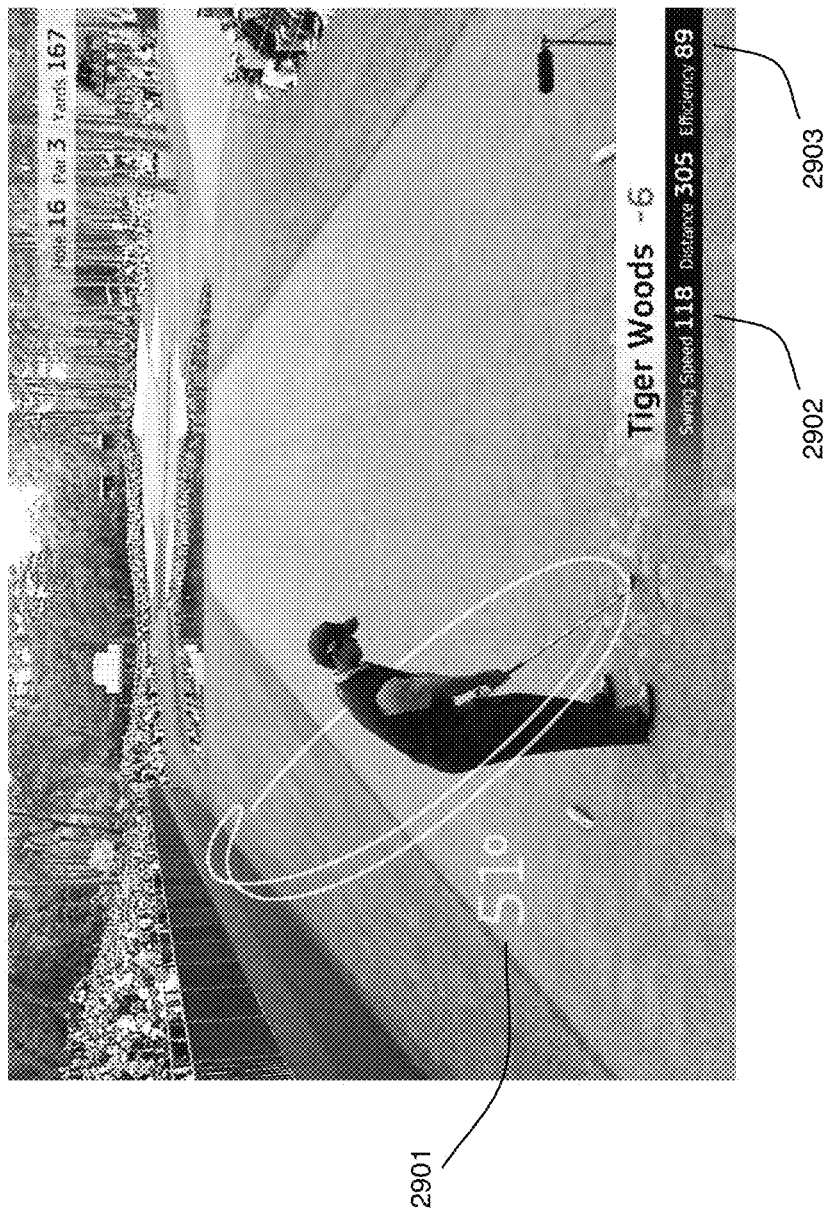
FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane in which the swing takes place versus the horizontal plane. In addition, other motion analysis data may be shown such as the swing speed, distance (calculated or actual) and efficiency.

A numerical form of the equations may be utilized to calculate the flight path for small increments of time assuming no wind and a spin axis of 0.1 radians or 5.72 degrees is as follows:

$x$ acceleration$=-0.00512*(vx^2+vy^2+vz^2)^{\wedge}(1/2)*$
$((46.0/(vx^2+vy^2+vz^2)^{\wedge}(1/2))*(vx)+(33.4/(vx^2+vy^2+vz^2)^{\wedge}(1/2))*(vy)*\sin(0.1))$ $y$ acceleration$=-0.00512*(vx^2+vy^2+vz^2)^{\wedge}(1/2)*$
$((46.0/(vx^2+vy^2+vz^2)^{\wedge}(1/2))*(vy)-(33.4/(vx^2+vy^2+vz^2)^{\wedge}(1/2))*((vx)*\sin(0.1)-(vz)*\cos(0.1)))$ $z$ acceleration$=-32.16-0.00512*(vx^2+vy^2+vz^2)^{\wedge}(1/2)*(46.0/(vx^2+vy^2+vz^2)^{\wedge}(1/2))*(vz)-(33.4/(vx^2+vy^2+vz^2)^{\wedge}(1/2))*(vy)*\cos(0.1))$ FIG. 29 illustrates a display of a broadcast television event wherein at least one motion capture element in the form of a motion sensor is coupled with the golf club and optionally the user. The display can be shown in normal time after the athlete strikes the ball, or in slow motion with motion analysis data including the three-dimensional overlay of the position of the sensor on the end of the club shown as a trace line and including the angle of the plane 2901 in which the swing takes place versus the horizontal plane. In addition, other motion analysis data may be shown such as the swing speed 2902, distance (calculated or actual) and efficiency 2903. This information or information in any other display described herein may be shown with or relative to data mining results of past performances of the player or other player for example based in any manner.

FIG. 29A illustrates a display of a user showing a portions of the swing, for example the locus of points that define the path of the motion sensor as projected onto a two-dimensional view, that are color coded in relation to another swing from that user or another user to show relative speed differences at different locations of the swing. For example, segment 2950 may be drawn in one color or with one line type or in any other manner that shows the relative speed difference at that particular spatial or time segment of a swing. Segment 2951 may be displayed in a second color or second line type or in any other manner for example that shows that the speed during that portion of the swing is higher or lower than another saved swing that has been saved from that user or another user or with respect to an average or "best" swing from that or another user. This display for example may display the second swing, i.e., saved swing that is being compared against, see FIG. 29B, or alternatively as shown, by showing only one swing, i.e., the current swing that is highlighted along its path to show the differences in speed at each point in time or space with respect to the comparison swing. In one embodiment, the current swing data as projected onto two-dimensional space is compared by breaking down the swing into segments from address to the highest point or rotation and back through the location of the ball. By normalizing at least one portion of the swing with respect to the time versus the comparison swing, one-to-one comparisons of velocity may be made at each data point of the current swing versus an interpolated set of speeds from the comparison swing since the number of samples may differ. Any other method of comparing two swings, for example by comparing velocity of each point in the current swing versus the speed at various heights that are normalized to the comparison swing is in keeping with the spirit of the invention. Displays that are color coded or show portions of motion that differ from the user's previous motion, or an average of the user's previous motion or the "best" motion from the user's previous motion may be shown on any computer coupled with embodiments of the invention. Although velocity is utilized in this example, any other parameter such as shaft bend, or grip pressure or foot weight distribution or any other measure parameter may be displayed or highlighted to show differences in the parameter versus any number of other swings from user 150 or any other user. This enables a user to compare practice swings to real swings taken on a golf course during play on mobile device 101 or at a later time, for example on mobile device 101 or computer 105 or via website 173, etc.

FIG. 29B illustrates a display of the user of FIG. 29A wherein the swing is shown in spatial relation to another swing, or average or swings or "best" swing of that user or another user. Swing path 2952, shown as a dotted line for ease of viewing, may represent another swing from the user or another user such as a historical player, or for example may represent the average spatial path of any set of swings from user 150. One method of calculating the average spatial swing is to take all swings from the user and normalize the swings with respect to the location of impact or horizontal orientation of the piece of equipment, e.g., club in this case and then average the location at each orientation or between the time points from the club highest negative orientation and lowest point or most vertical and lowest orientation. Any other method of determining an average swing path, or any other maximum, minimum, mean, median or other mathematical value from a plurality of swings and displaying the current swing in relation to the other mathematical value is in keeping with the spirit of the invention. See also FIG. 36A. In one or more embodiments of the system, random or any other mathematical construct of one or more swings may be utilized to play a game with a real user, for example that is actually playing golf on a course with respect to a virtual opponent that for example tees off after the user has teed off and calculates the location of the virtual ball for example based on a historical golfer's average swing for a particular distance to the hole. As the game progresses, the score of the real user and the virtual opponent is updated until the game is complete. Alternatively, one player may be playing the golf course while another player is swinging on a driving range and wirelessly exchanging motion capture data, or ball flight information to calculate distance to the hole after each shot. This enables real game play from two distally located players, one of which is on a particular golf course, the other not. Embodiments of the invention enable two distally located players to wager against one another where legal by accepting a bet and optional credit card or other bank account information and transferring the money using ACH or other monetary transfer mechanism to settle the account after the game finishes.

Figure 30:
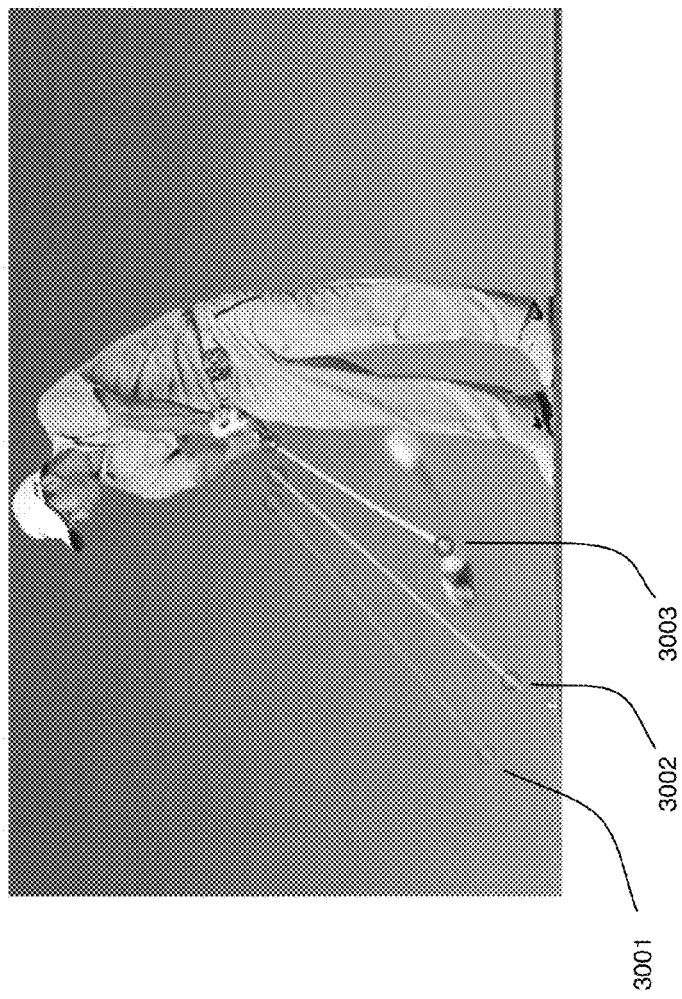
FIG. 30 illustrates a display of the swing path with a strobe effect wherein the golf club in this example includes sensors on the club head and near the handle, or optionally near the hands or in the gloves of the user. Optionally, imaged based processing from a high speed camera may be utilized to produce the display. The swing path for good shots can be compared to swing paths for inaccurate shots to display the differences in a human understandable manner.

FIG. 30 illustrates a display of the swing path with a strobe effect wherein the golf club in this example includes sensors on the club head and near the handle, or optionally near the hands or in the gloves of the user. Optionally, imaged based processing from a high speed camera may be utilized to produce the display. A line or captured portion of the actual shaft from images may be displayed at angle 3001, 3002 and 3003 for example. The swing path for good shots can be compared to swing paths for inaccurate shots to display the differences in a human understandable manner.

Figure 31:
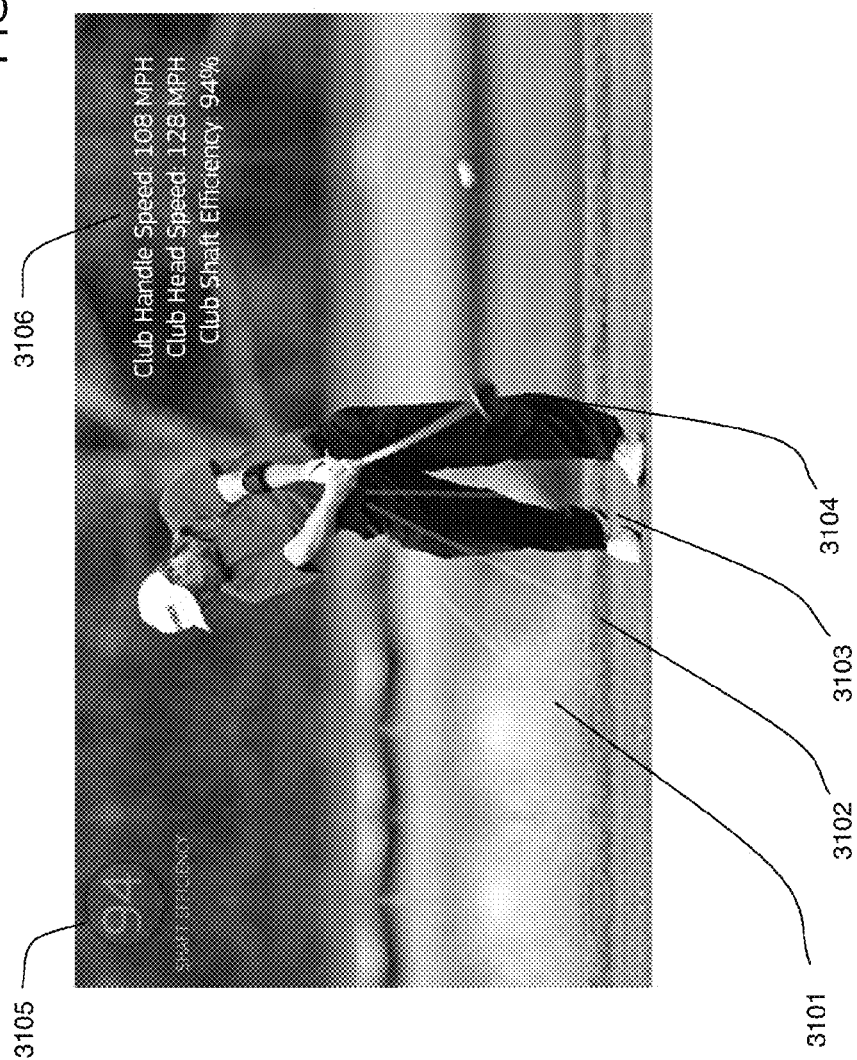
FIG. 31 illustrates a display of shaft efficiency as measured through the golf swing. For example, by obtaining motion capture data near the club head and club handle, graphical strobe effects and motion analysis data can show the club head speed, club handle speed and club shaft efficiency in normal time or slow motion.

FIG. 31 illustrates a display of shaft efficiency 3105 as measured through the golf swing. For example, by obtaining motion capture data near the club head and club handle, graphical strobe effects and motion analysis data can show the club head through time at 3101, 3102, 3103 and 3104 and also display speed, club handle speed and club shaft efficiency at 3106 in normal time or slow motion.

Figure 32:
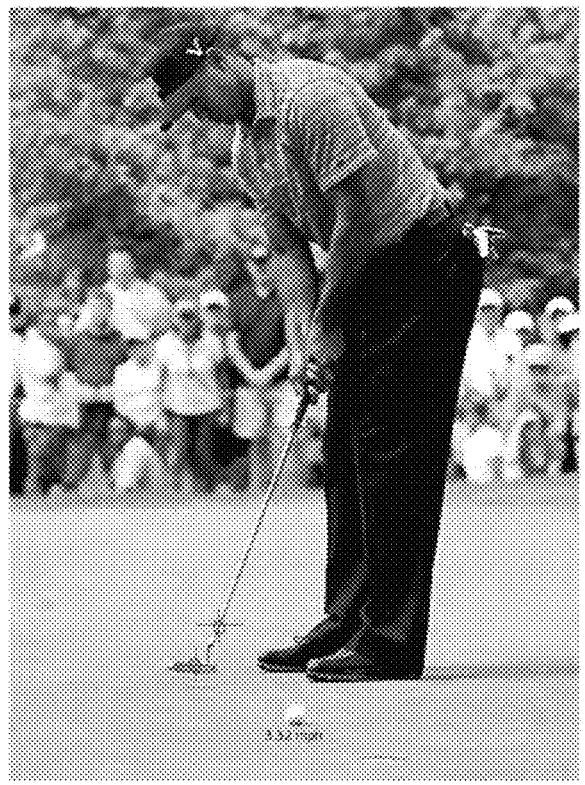
FIG. 32 illustrates a display of putter head acceleration based on at least one sensor near the putter head, for example as coupled into the weight port of a putter. The various quantities from the motion analysis data can be displayed to aid in understanding acceleration patterns for good putts and bad putts to help viewers understand acceleration in a more human understandable manner.

FIG. 32 illustrates a display of putter head speed and/or acceleration based on at least one sensor near the putter head, for example as coupled into the weight port of a putter. The various quantities from the motion analysis data can be displayed at 3201 to aid in understanding speed and/or acceleration patterns for good putts and bad putts to help viewers understand speed and/or acceleration in a more human understandable manner.

Figure 33:
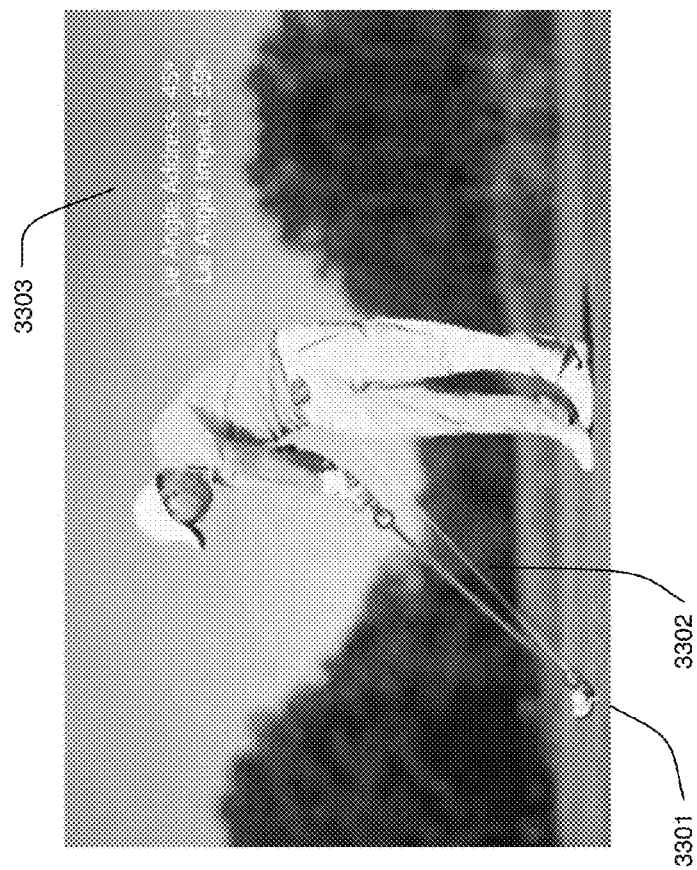
FIG. 33 illustrates a display of dynamic lie angle, wherein the lie angle of the player at address before swinging at the ball can be compared to the lie angle at impact to help the viewer understand how lie angle effects loft and ball flight.

FIG. 33 illustrates a display of dynamic lie angle, wherein the lie angle of the player at address 3302 before swinging at the ball can be compared to the lie angle at impact 3301 to help the viewer understand how lie angle effects loft and ball flight, while quantitatively showing the values at 3303.

Figure 34:
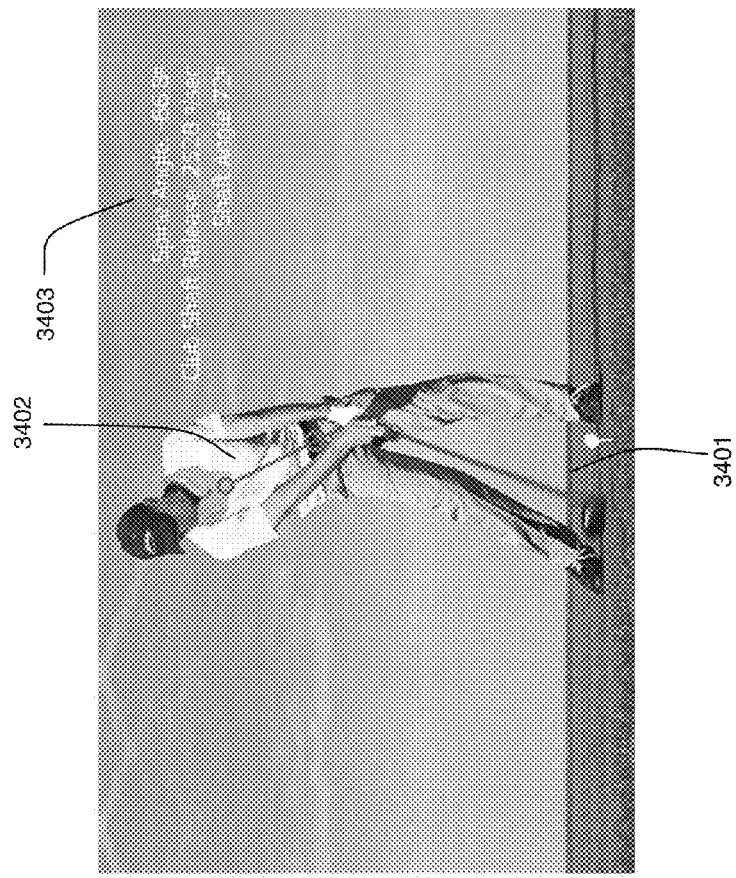
FIG. 34 illustrates a display of shaft release, wherein the angular release velocity of the golf shaft is a large component of the efficiency of a swing. As shown, a display of a golfer that has sensors near his waist and hips and sensors on the golf club head and handle, or as determined through image processing with or without visual markers, is shown with the motion analysis data.

FIG. 34 illustrates a display of shaft release, wherein the angular release velocity of the golf shaft is a large component of the efficiency of a swing. As shown, a display of a golfer that has sensors near his waist and hips (to produce spine angle 3402) and sensors on the golf club head and handle (to produce shaft angle 3401), or as determined through image processing with or without visual markers, is shown along with the motion analysis data including club shaft release in degrees per second at 3403.

Figure 35:
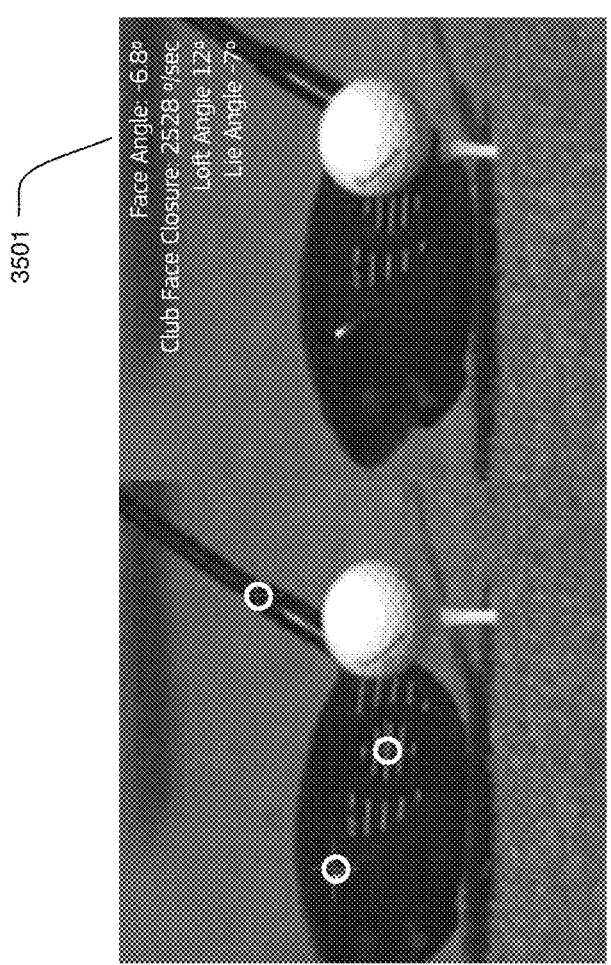
FIG. 35 illustrates a display of rotational velocity wherein the face angle, club face closure in degrees per second, the loft angle and lie angle are shown as obtained from a motion capture element on the club head for example.
Figure 36:
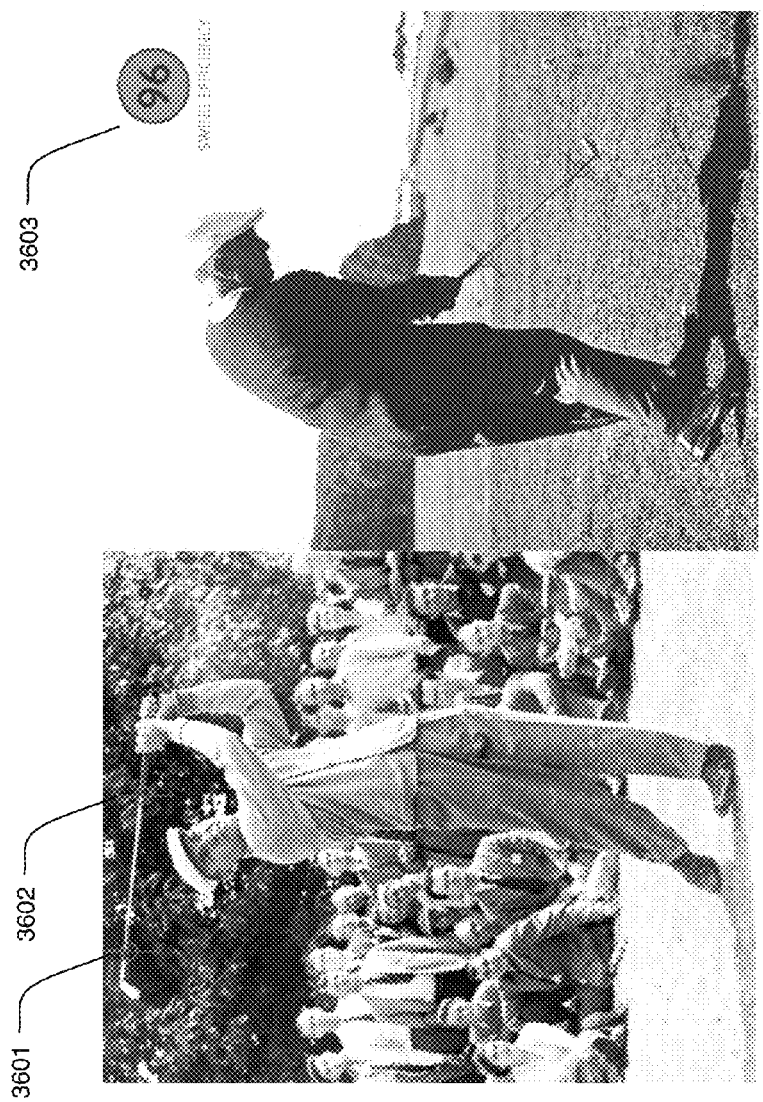
FIG. 36 illustrates a display of historical players with motion analysis data computed through image processing to show the performance of great players.

FIG. 35 illustrates a display of rotational velocity wherein the face angle, club face closure in degrees per second, the loft angle and lie angle are determined from a motion capture sensor coupled with the club head for example and numerically shown at 3501. In one or more embodiments of the invention, a piece of equipment that includes two motion capture elements on opposing ends of the equipment, for example in the club head and handle of a golf club may include a calibration stage wherein the club face angle which is known and the angular orientations of the mounted motion capture sensors are calibrated so that their exact offsets for example with respect to the orientation of the shaft of the golf club is taken into account. In this manner, fitting experts and performance data in general related to the club can be normalized to the actual orientation of the club to ensure consistent data FIG. 36 illustrates a display of historical players with motion analysis data computed through image processing to show the performance of great players. By tracing and determining the locations of two points 3601 and 3602 on each player's golf club as shown and knowing the height of the players and/or lengths of their clubs and angle at which the images where taken, distances and thus velocities of the golf clubs may be determined to calculate numerical values as shown at 3603. This information may be stored posthumously in database 172 and data mining may be performed using the data as previously described. Users 150 may be compared against the greats and displayed on any computer described herein for example so long as the computer includes a display.

Figure 36A:
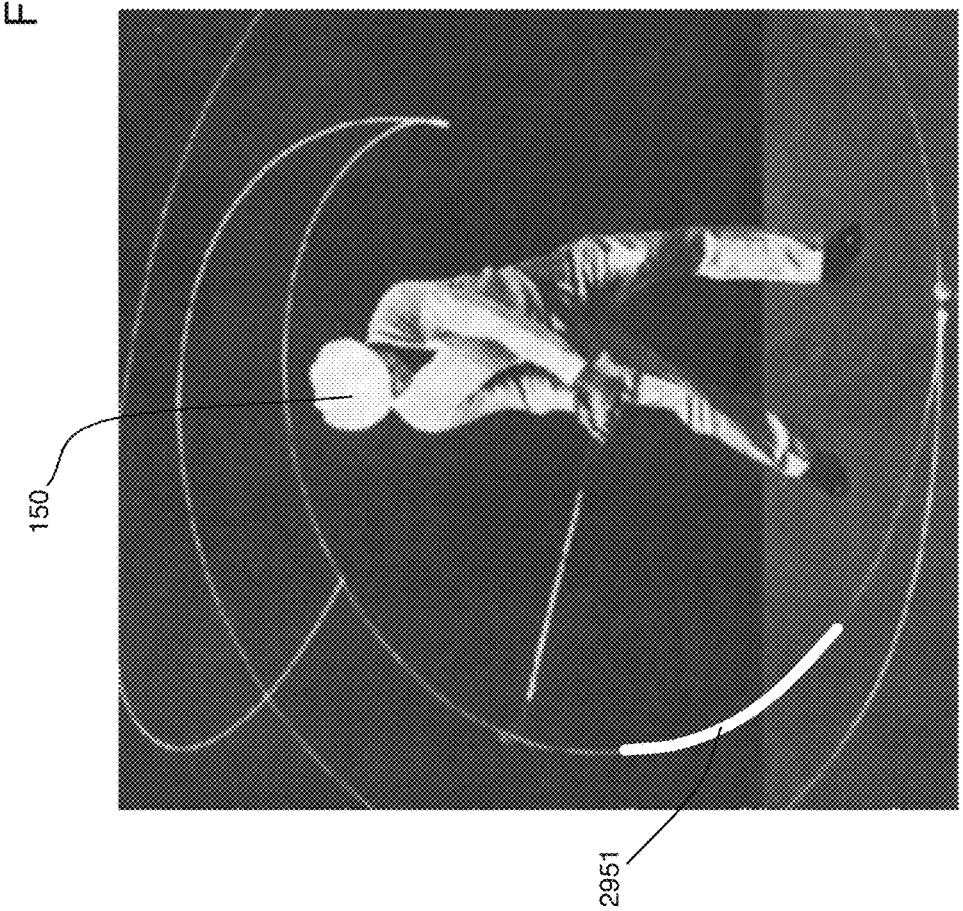
FIG. 36A illustrates a display of a historical player showing the motion from a motion capture sensor or as calculated through image processing and which may be compared to or contrasted with a given user's swing (see also FIGS. 29A and 29B).

FIG. 36A illustrates a display of historical player 150 showing the motion from a motion capture sensor or as tracked or calculated through image processing and which may be compared to or contrasted with a given user's swing (see also FIGS. 29A and 29B) or against other swings or a combined mathematical value associated with two or more swings from the historical player or any other player. Segment 2951 is shown as a thick white line to indicate that the current swing differs in relation to other swings from the historical player or any other user for example. In one embodiment, given the position difference between the club head in subsequent frames and knowing the frame rate at which the film was captured, enables velocity to be calculated at points along the swing path. Based on the relatively low number of samples, a large number of current swing samples from a particular user may be normalized in space or time to enable one-to-one comparison at numerous points along the swing path. Points may be interpolated in any manner to provide more points or averaged along the path to make the comparison easier to calculate as desired and to the level of accuracy desired. See also FIGS. 29A and 29B.

FIG. 37 illustrates one embodiment of the equations used for predicting a golf ball flight path as used to produce displays as shown in FIGS. 27 and 28.

FIG. 38 shows elements of an embodiment of the invention 3800 configured to fit into the end of a golf shaft. (See also FIG. 11 for another embodiment that may fit into a golf shaft or couple near the head of a golf club). Sensor 3801 may include spatial sensors that obtain data associated with orientation, position, velocity, acceleration (or any other derivative with respect to position and time). For example, accelerometer(s) may be utilized that obtain acceleration data in one or more axes. Alternatively, or in combination, the sensors may include gyroscope(s) that allow for orientation with respect to the horizon to be accurately determined. Alternatively, or in combination, the sensors may include magnetometers that allow for orientation with respect to North/South to be accurately determined. Any combination of these sensor types may be utilized to obtain spatial data that may be utilized by embodiments of the system described to analyze and display the spatial data in a user-friendly manner. Embodiments of the apparatus may include microcontroller 3802, i.e., a programmable computer element is small form factor, for example a low power microcontroller. One or more embodiments of the apparatus may include a unique identifier that identifies the particular instance of the apparatus. The identifier may be stored in the memory of microcontroller 3802 or in a separate chip (not shown for brevity and since microcontroller 3801 may include memory) or may be received by the microcontroller from an external system, i.e., programmed. In combination or alternatively, an identifier may be stored on identifier 191, for example implemented as an RFID tag that may be mounted on the end of the club or on the handle or under the handle of the club or in any other position on the club so long as the identifier may be read, for example by the computer on the mobile device. One or more embodiments of the invention may utilize passive RFID tags so that no battery is required to identify the specific club, or for example the club number of a particular club. Any other mechanism for obtaining a unique identifier that may be utilized with embodiments of the invention is in keeping with the spirit of the invention. The apparatus may also include radio and antenna 3803 (or separately as per FIGS. 40 3803a and 4001) to enable wireless communication of the unique identifier and spatial data, for example via a communication mechanism that for example minimizes or eliminates communication interference so that multiple clubs from one or more players may be used in the same vicinity without communication interference. One or more embodiments of the radio may comprise BLUETOOH®, adaptive frequency hopping spread spectrum, or code division multiple access (CDMA) or other wireless communications technologies having for example multiple channels of communication to allow for multiple radios to operate in a given location without interference. Power for the apparatus may derive from one or more batteries 3804. For example one or more CR1216 batteries may be utilized to double the amount of time that the club may be utilized. Embodiments of the apparatus may utilize mounting board 3810, for example a printed circuit board to mount the various components to. In addition, adapter 3805 may be utilized to house sensor 3801, microcontroller 3802, radio/antenna 3803, battery or batteries 3804 directly or via mounting board 3810 that may couple with these elements. Adapter 3805 may be unique to each golf club, manufacturer, model or any available standard, for example a handle standard size. In one or more embodiments adapter 3805 may comprise a 25 mm deep and 14.5 mm in diameter tube structure, for example made of epoxy or plastic or any other material strong enough to hold the various components in place and withstand the force involved with a golf swing. In addition, embodiments of the invention may also utilize cap 3806, for example a closure cap that is utilized to cover mounting board 3810 within the club handle (or club head). Closure cap 3806 may include a visual marker as is shown in FIGS. 9, 10 and 12 for example, for visual processing. In addition, cap 3806 may include a push switch to power the apparatus on and/or off. One or more embodiments of the invention power off automatically, or go into a hibernation mode after a particular amount of time the golf club has not moved over a certain speed for example. This may include mechanical and/or electronic indications that the club has moved and hence power should be restored. In addition, some or all of the components may be powered down and up periodically or until motion occurs or to check for a communications link for example. Any other power saving features may be implemented as desired to save more power based on the design requirements for a desired application as one skilled in the art will appreciate. In addition, by obtaining the spatial data from multiple apparatus coupled with a particular club for example enables the automatic determination of which apparatus is located in a handle and which apparatus is located at the golf club head based on the differences in speed during a swing for example. Any other method for automatically determining the assigned location of each apparatus on a given golf club is in keeping with the spirit of the invention. Example spatial sensor 3801 embodiments follow. One or more embodiments of the invention may utilize a MEMS digital output motion sensor LIS331HH ultra low-power high full-scale 3-axes "nano" accelerometer, or any other accelerometer for example. One or more embodiments of the invention may utilize a AK8975/AK8975C 3-axis electronic compass, or any other compass for example. One or more embodiments of the invention may utilize a L3GD20 MEMS motion sensor three-axis digital output gyroscope or any other gyroscope for example. One or more embodiment of microcontroller 3802 may be implemented with MICROCHIP® PIC24FJ256GA110 general purpose flash microcontroller or any other microcontroller. One or more embodiments of radio and antenna 3803 may be implemented with a BLUECORE®6-ROM single-chip BLUETOOTH® v2.1 EDR system, and/or a BLUECORE® CSR1000™ QFN BLUETOOTH® low energy single-mode chip, or any other communications chip. Any type of micro-power harvesting technology may be utilized internally to charge a battery coupled to the microcontroller to minimize the changing or charging of batteries with an external charger.

In addition, embodiments of mount may utilize the mount specified in the priority chain application U.S. Ser. No. 13/191,309 which has been incorporated by reference above in the priority claim.

Embodiments of the invention using a unique identifier may be utilized as a lost club alarm, so that if contact is lost with one of the clubs associated with a player, an alarm may be presented by one or more embodiments of the system. Embodiments of the system that include a three-axis accelerometer enable analysis and display of swing speed, tempo, handle versus head speed, swing efficiency, durability counter and shot by shot analysis. Embodiments of the invention that include a three axis gyroscope enable analysis and display of alignment, lie angle, loft angle, handle release and 3-D angular velocity. Embodiments of the invention that include a magnetometer enable analysis and display of swing tracer, swing path, impact location, ball flight, 3-D impact, shaft deflection, shaft efficiency and 3-D video overlay. Any other displays that make use of the different type of spatial sensors is in keeping with the spirit of the invention.

Figure 39:
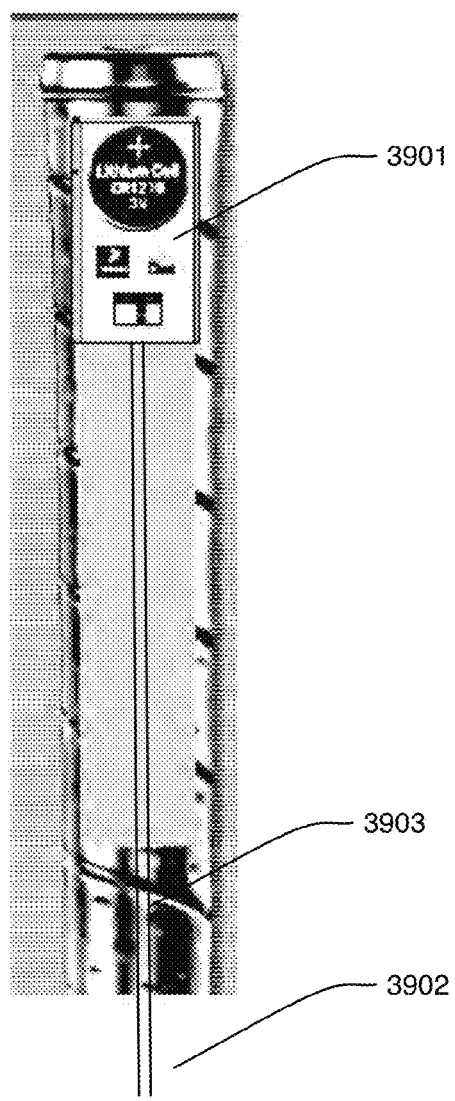
FIG. 39 shows an embodiment of the apparatus of FIG. 38 integrated into the handle of a golf club.

FIG. 39 shows an embodiment of the apparatus of FIG. 38, here designated 3901 as integrated into the handle of golf club 3902. Optional electrical connection 3903 enables the coupling of an embodiment of the invention situated in a handle of a golf club to an embodiment of the invention situated near the golf club head so as to allow for simultaneous recharging of both apparatus. Cap 3806 may include an inductive coil to allow for wireless charging (as is common in electric toothbrushes for example), or may include any type of power coupling interface or outlet, as one skilled in the art will appreciate. Any type of mechanical charging element, for example common in some watches, may also be coupled to the motion capture elements that do not require power. In addition, automatic power up and power down passive or active sensors or switches may be utilized to power microcontroller 3802 on or off.

Figure 39A:
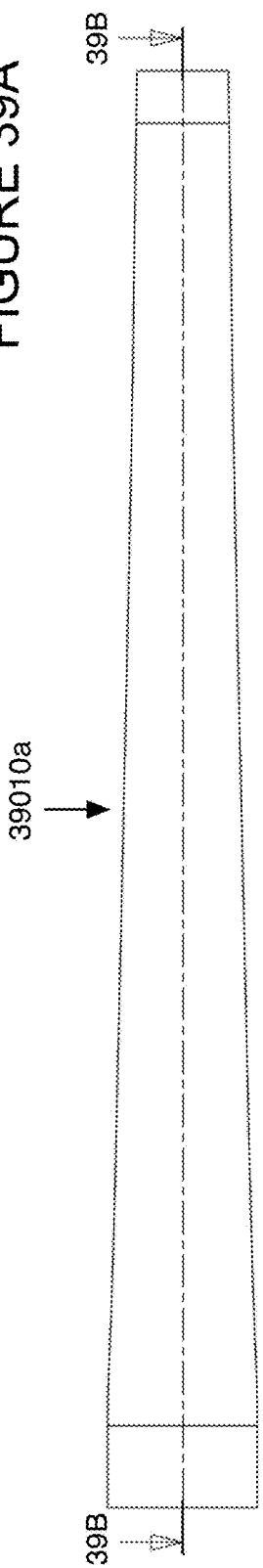
FIGS. 39A-39G show an embodiment of a handle based integrated mount.
Figure 39B:
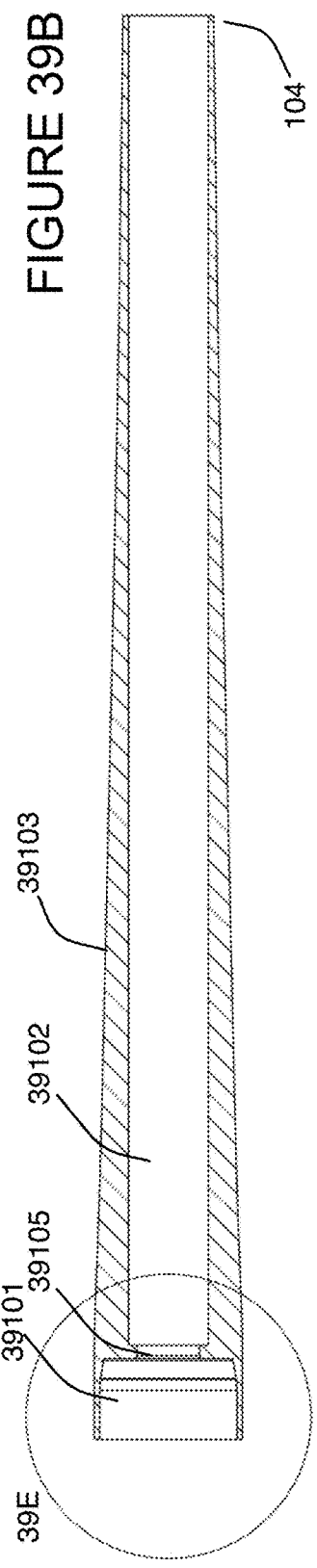
Figure 39C:
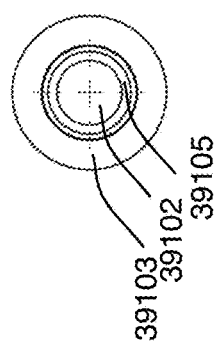
Figure 39G:
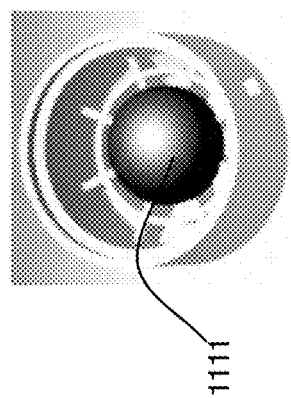

FIGS. 39A-39G show an embodiment of a handle based integrated mount. Specifically, FIG. 39A illustrates a side view of integrated embodiment of the invention 39010a configured as a handle. As shown in FIG. 39B, which illustrates a cutaway view of FIG. 39A, the integrated embodiment includes first hollow area 39102 configured to couple with a shaft of a piece of equipment and second area 39101 configured as an enclosure to hold a motion capture element and battery or a slug weight of equal weight to the motion capture element and battery for example. As shown, handle portion 39103 may have a tapered shape with a greater thickness near second area 39101 with respect to distal end 39104 shown in the right portion of the figure. Handle portion 39103 may be constructed from any material and may include a grip or alternatively may couple with the inside portion of a grip that is situated around handle portion 39103. A smaller diameter ledge 39105 separates the first and second areas. Alternatively, the ledge may extend completely across to separate the first area from the second area. FIG. 39B illustrates second area 39101 that holds the motion capture element and battery or alternatively slug weight 1111 as shown in FIG. 39G.

FIG. 39C illustrates an end view of the integrated embodiment of the invention from the narrow end that is generally furthest away from the hands of a user, as shown from distal end 39104. First area 39102 generally has a diameter configured to fit a standard piece of equipment, for example a golf shaft or tennis racquet, etc. Also shown in the tapered area, i.e., handle portion 39103.

Figure 39D:
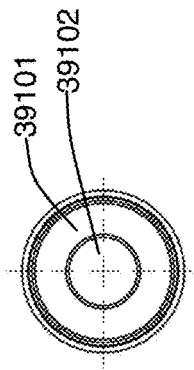

FIG. 39D illustrates an end view of the integrated embodiment of the invention from the end configured to house the motion capture element and battery or slug weight. As shown, the diameter of the second area 39101 is configured large enough to hold a motion capture element and standard battery or batteries in one or more embodiments. By providing an area in the handle that is preconfigured for a motion capture element, integrated embodiments of the invention may be coupled with a piece of equipment and upgraded in the future to include motion capture elements without any modification to the equipment by removing a slug weight from the second area and replacing it with a motion capture element. In this manner, no physical characteristic of the piece of equipment changes at all if the slug weight is chosen to match the weight of the motion capture element and any other components to be placed in the second area, for example a battery or batteries.

Figure 39E:
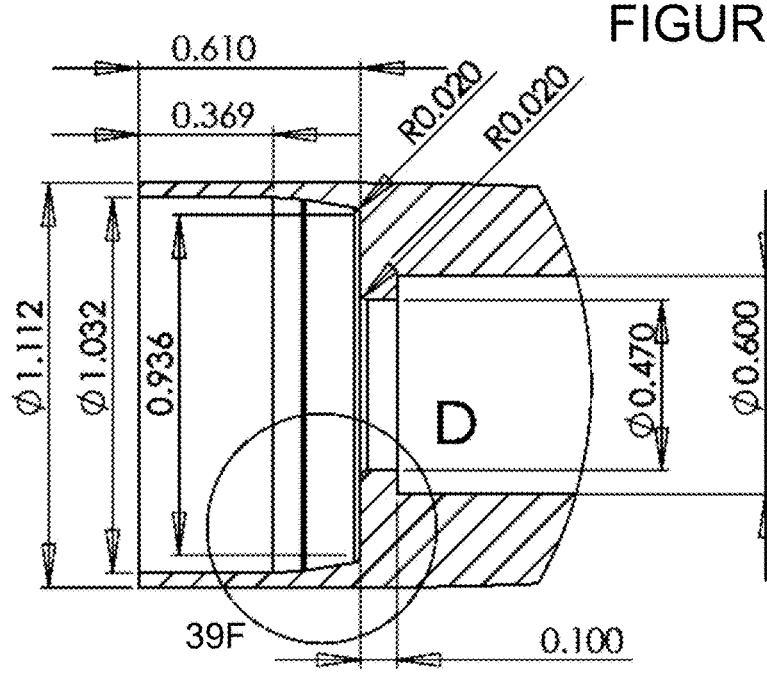

FIG. 39E illustrates a close-up cutaway view of FIG. 39A showing the second area configured as an enclosure to hold a motion capture element and battery or a slug weight of equal weight to the motion capture element and battery for example. Measurements shown in the figure are exemplary and not required. Units are shown in inches.

Figure 39F:
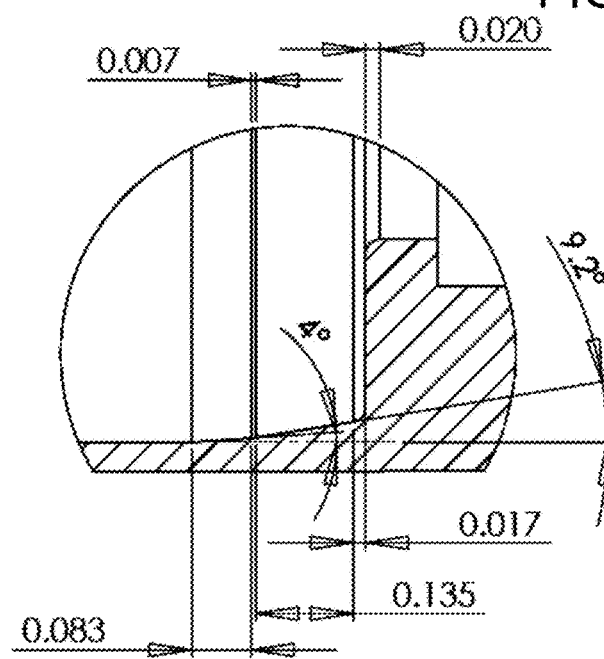

FIG. 39F illustrates a close-up view of a portion of FIG. 39E showing the second area in greater detail. Tapered and angled areas are optional so long as the first area can hold a motion capture element.

FIG. 39G illustrates a perspective bottom view of slug weight 1111 utilized with integrated and non-integrated embodiments of the invention to maintain an equivalent weight for the piece of equipment. Hence, whether a motion capture element and batteries are installed or replaced with the slug weight for example, the weight and torque characteristics of the piece of equipment may remain unchanged when the piece of equipment is upgraded to include a motion capture element. As shown, slug weight 1111 is situated in the underside of a cap that is configured to enclose second area 39101. In one or more embodiments, the cap may include a post or other item to rotationally lock the cap into the first area for example. Threads or any other coupling element may be utilized to hold the cap with an embodiment of the invention.

Figure 40:
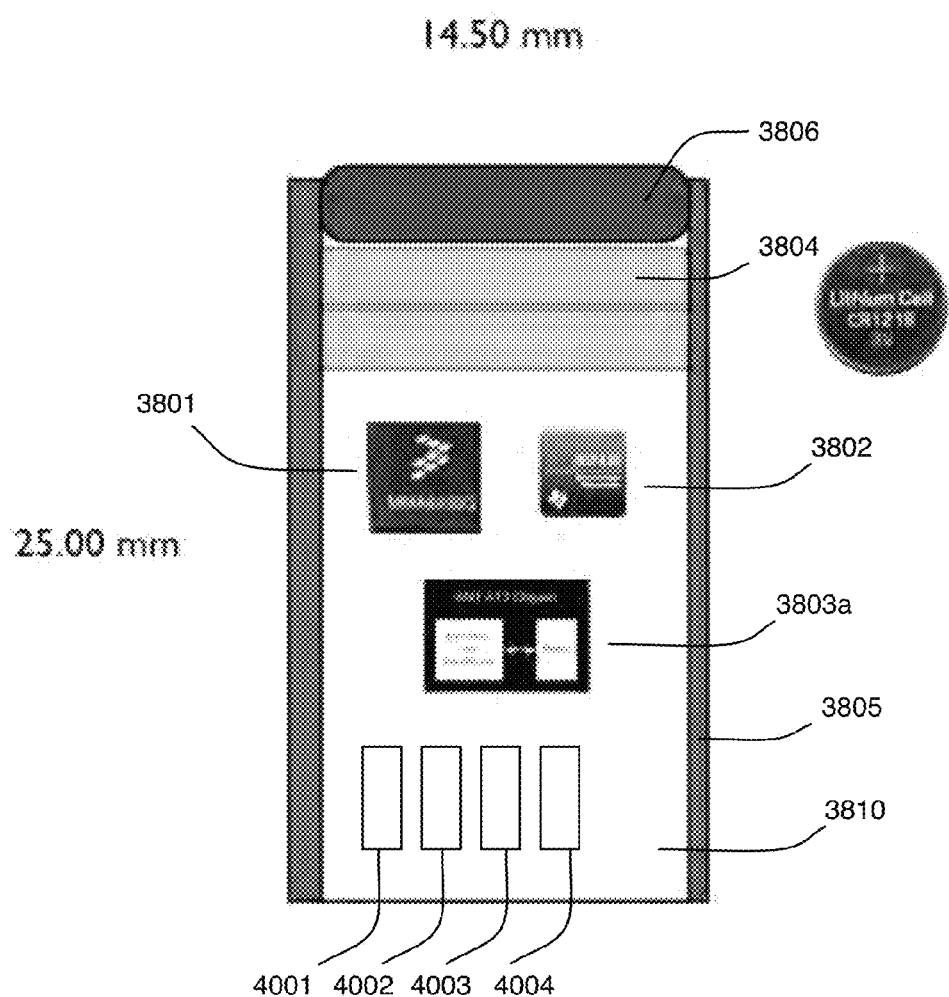
FIG. 40 shows elements of another embodiment of the invention configured to fit into the end of a golf shaft

FIG. 40 shows elements of another embodiment of the invention configured to fit into the end of a golf shaft. In this embodiment, mounting board 3810 also includes radio 3803a, along with antenna 4001 (as separate units compared with FIG. 38), optional heat sink 4002, recharger 4003 and overcharge detector 4004. Recharger 4003 may be implemented for example as an induction element that wirelessly enables recharging battery or batteries 3804. Overcharge detector 4004 may electrically connect with battery or batteries 3804 and recharger 4003 to determine when the batteries should no longer be charged, or when charging should resume. Alternatively, a wired connection may be utilized to charge battery or batteries 3804 as one skilled in the art will appreciate. In addition, since a wire may be run through the shaft of the golf club, the same charging port may be utilized to charge batteries in two or more apparatus, for example one located in a golf club handle and another one located near the golf club head. A wireless golf club is thus produced with a wired internal connection for ease of charging.

Figure 41:
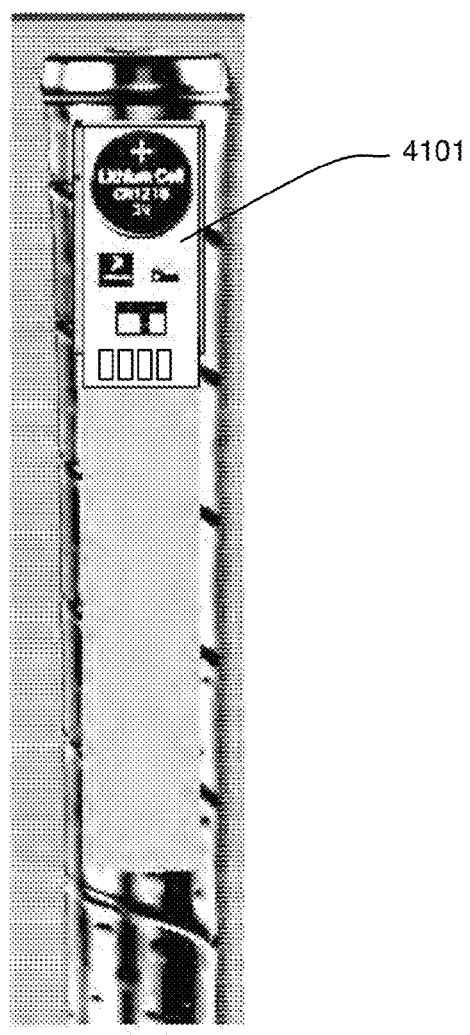
FIG. 41 shows another embodiment of the apparatus of FIG. 40 integrated into the handle of a golf club.
Figure 41A:
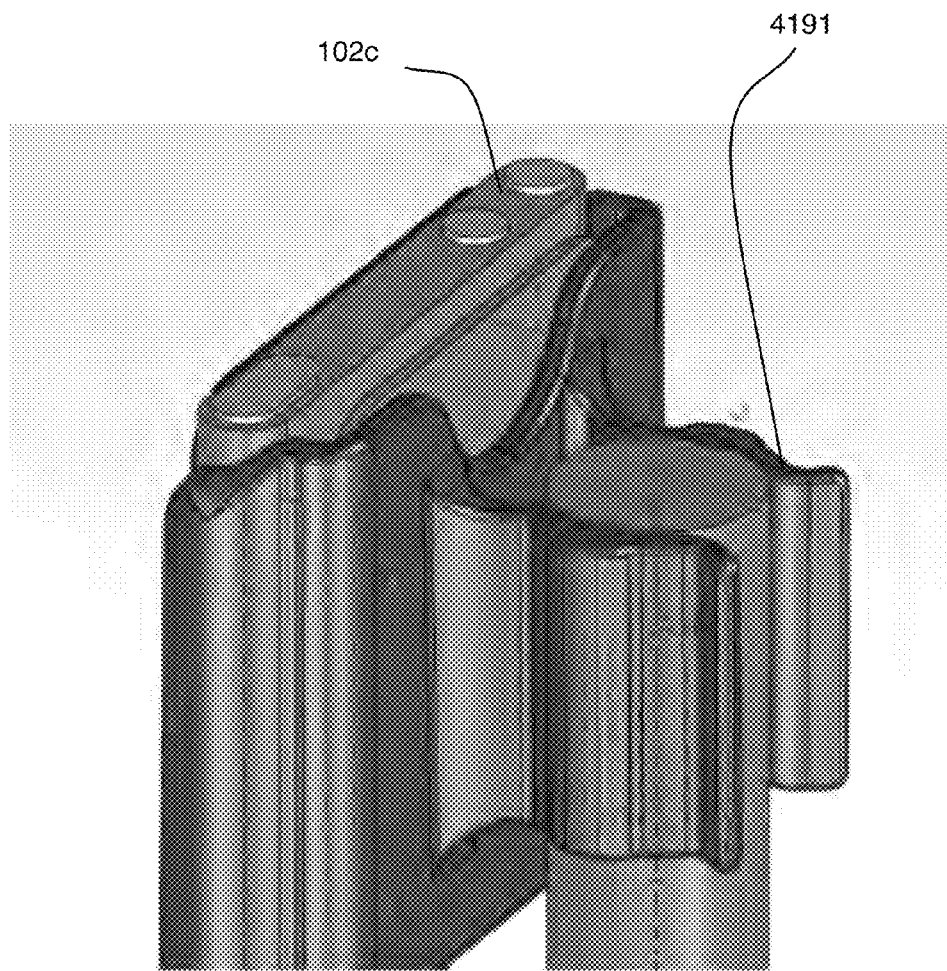
FIG. 41A illustrates and embodiment of an external mount for a mobile computer to couple the mobile computer to a piece of equipment.

FIG. 41 shows another embodiment of the apparatus of FIG. 40, here designated 4101 as integrated into the handle of golf club 3902. FIG. 41A shows an embodiment of mount 4191 for mobile computer 102c, here an IPOD® NANO® for example that mounts to a stick or shaft for example the shaft of a golf putter via clips shown in the right of the figure that couple with the shaft as shown.

FIG. 41A illustrates and embodiment of an external mount for a mobile computer to couple the mobile computer to a piece of equipment. As shown the mount may clip to the shaft which allows for very small embodiments of the mobile computer to mount on the piece of equipment, so long as they do not interfere with the swing of a user, for example on a putter. Any other method of mounting or carrying the mobile computer is in keeping with the spirit of the invention.

Figure 41B:
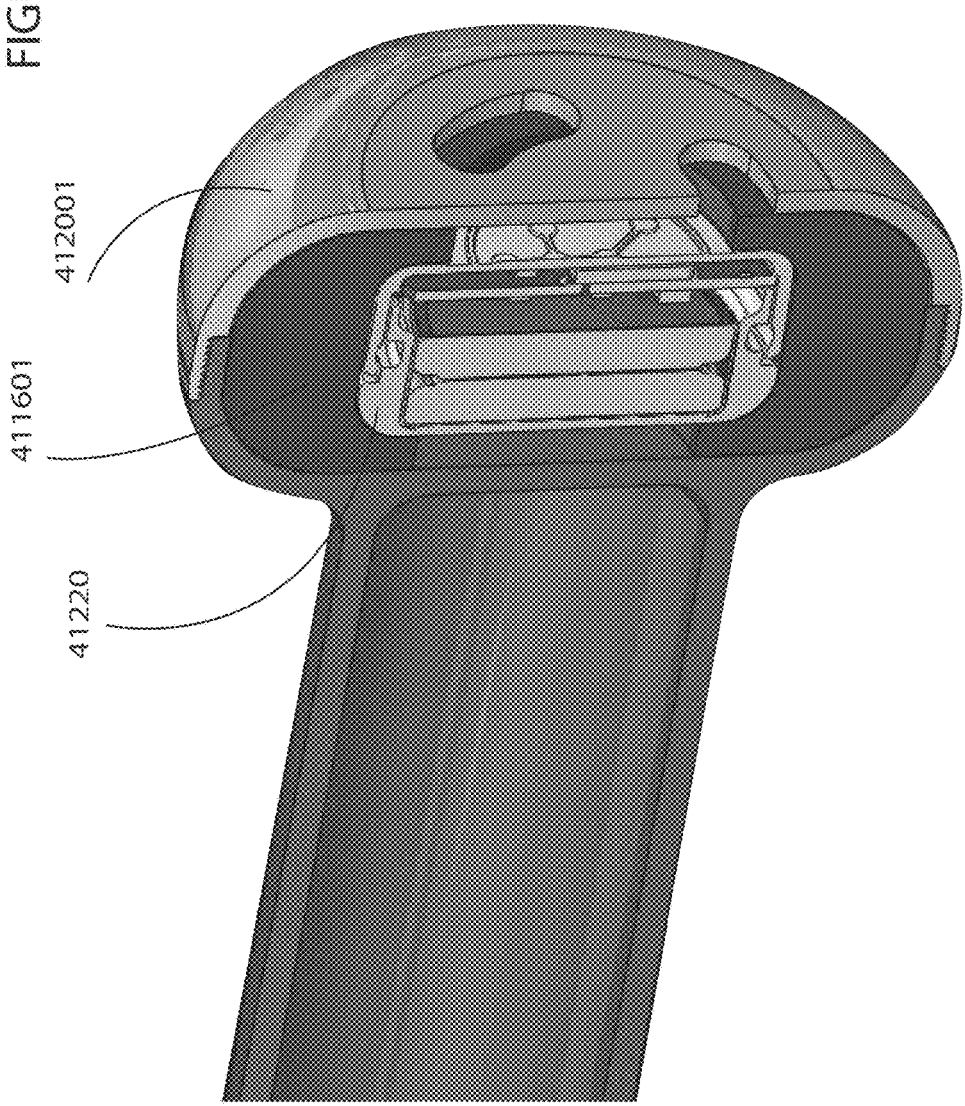
FIG. 41B illustrates a baseball mount, shock puck surrounding the motion capture sensor and baseball bat handle portion in cross-sectional view.

FIG. 41B illustrates a cutaway view of an embodiment of the invention coupled with a piece of equipment having a handle, for example a baseball mount, shock puck surrounding the motion capture sensor and baseball bat handle portion in cross-sectional view. As shown, shock puck 411601 surrounds enclosure 41220 to provide high G-force shock protection to the internal components of the motion capture sensor. One or more embodiments of the invention may be covered with an outer protective area 412001, which may be transparent in one or more embodiments.

FIG. 41C illustrates a helmet based mount, that enables coupling to a helmet or otherwise retrofit the helmet for determining acceleration of the helmet and/or head for concussion determination applications for example. As shown, enclosure 41220 is coupled with helmet via facemask tube or grill 412201. Any other method of coupling the enclosure with a helmet is in keeping with the spirit of the invention.

Figure 41D:
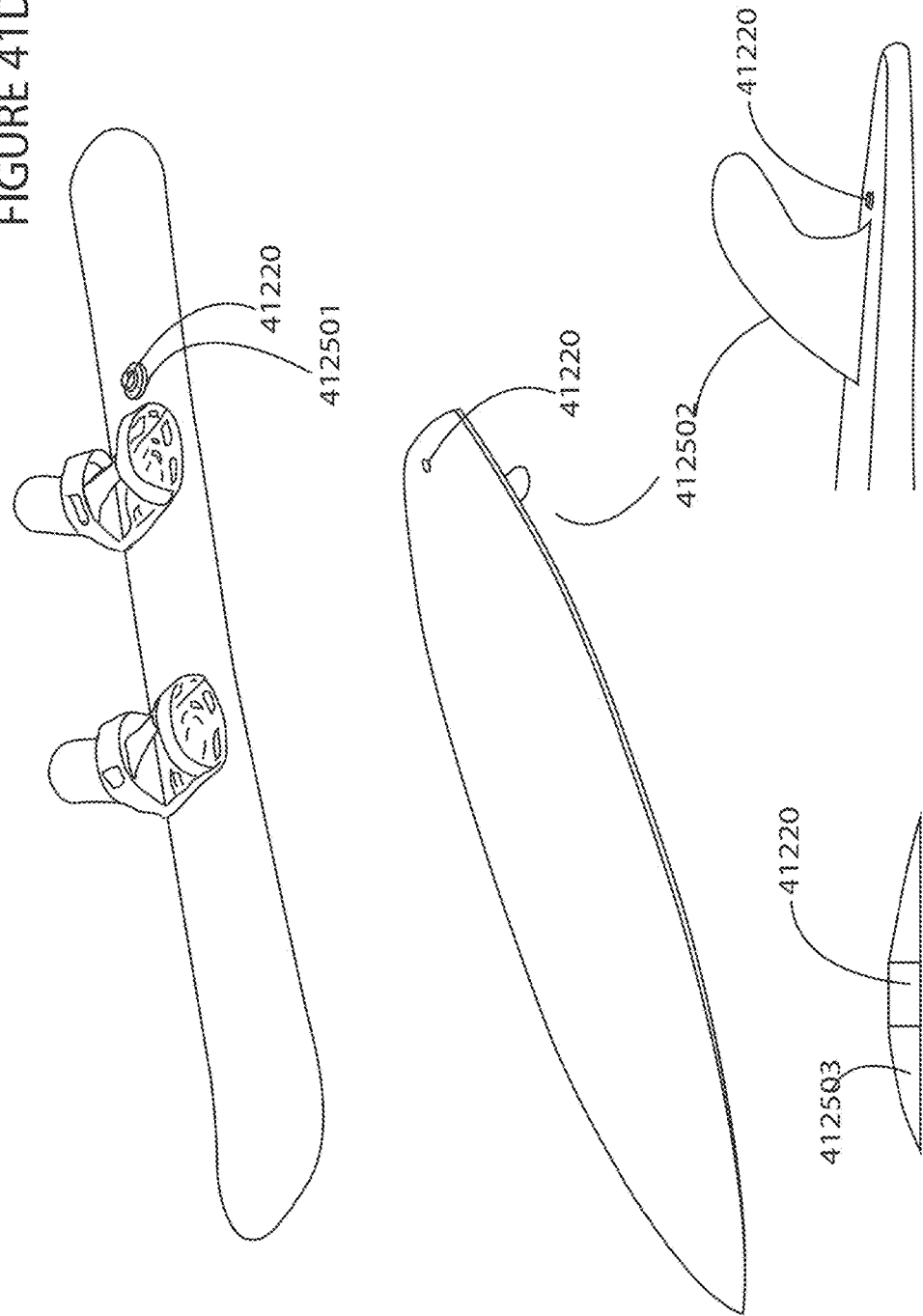
FIG. 41D illustrates embodiments of the mount for snowboard and surfboard applications wherein embodiments of the invention may be interchanged from one piece of equipment to the other and utilized without the need to buy multiple sensors. In one or more embodiments, a different personality may be utilized for capturing data to optimize the captured data depending on particular movement for example associated with the piece of equipment or clothing.

FIG. 41D illustrates embodiments coupled with planar equipment, for example for snowboard and surfboard applications, or other planar equipment such as skis or skateboards as one skilled in the art will appreciate, wherein embodiments of the invention may be interchanged from one piece of equipment to the other and utilized without the need to buy multiple sensors. In one or more embodiments, a different personality may be utilized for capturing data to optimize the captured data depending on particular movement for example associated with the piece of equipment or clothing. As shown, enclosure 41220 may be mounted along with the snowboard binding 412501 of a snowboard. In one or more embodiments, the enclosure may be coupled with the snowboard mount itself, or utilize a flat version of mount 412401 to couple with an existing screw used to mount the binding. As shown in the lower portion of the figure, enclosure 41220 may mount on or near the top of the surfboard or on the underside of the surfboard near the skeg 412502 since surfboards may be made from materials that enable the transmission of electromagnetic waves. In one or more embodiments enclosure 41220 may be housed in streamlined mount 412503 and adhesively mounted to any planar equipment, for example the snowboard, surfboard or skis. Streamlined mounts provide low wind or water drag and minimize interference with external objects for example.

Figure 42:
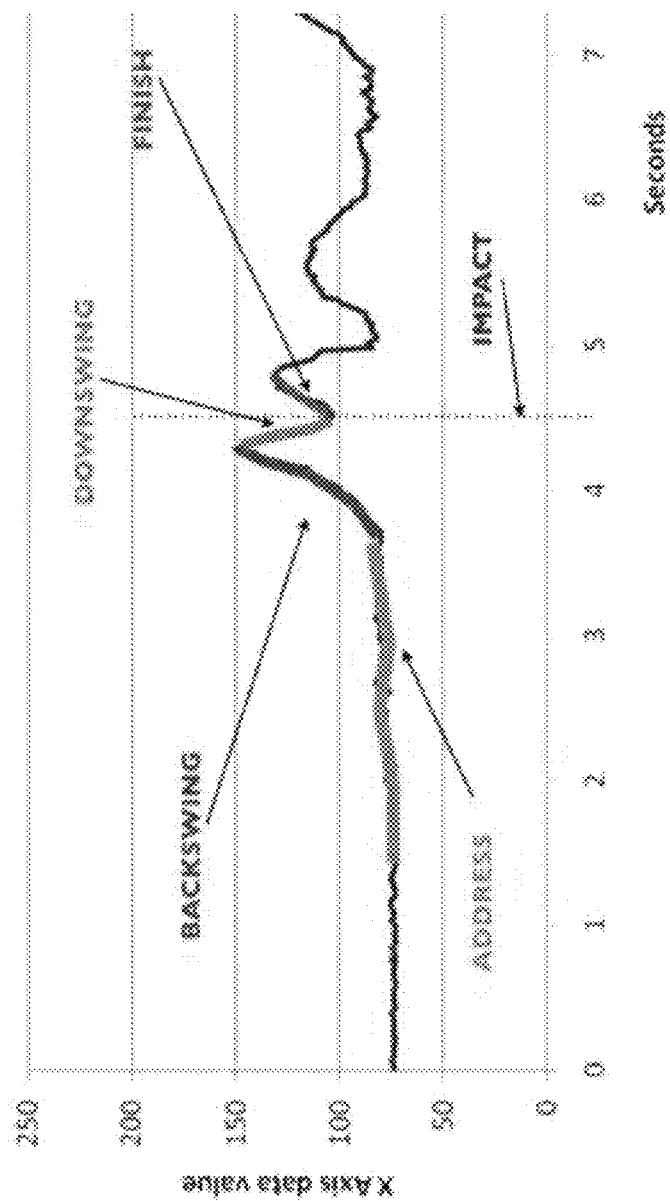
FIG. 42 shows a graph of swing data as obtained from one or more embodiments of the motion capture element.

FIG. 42 shows a graph of swing data as obtained from one or more embodiments of the invention. Any other user-friendly display may be utilized that includes spatial data obtained from one or more embodiments of the invention as one skilled in the art will recognize. In the figure as shown, the X-axis data may be utilized to show position versus time to graphically display information related to a golf swing. Any other display as previously described above may also be utilized to display spatial data associated with one or more embodiments of the invention.

Figure 43A:
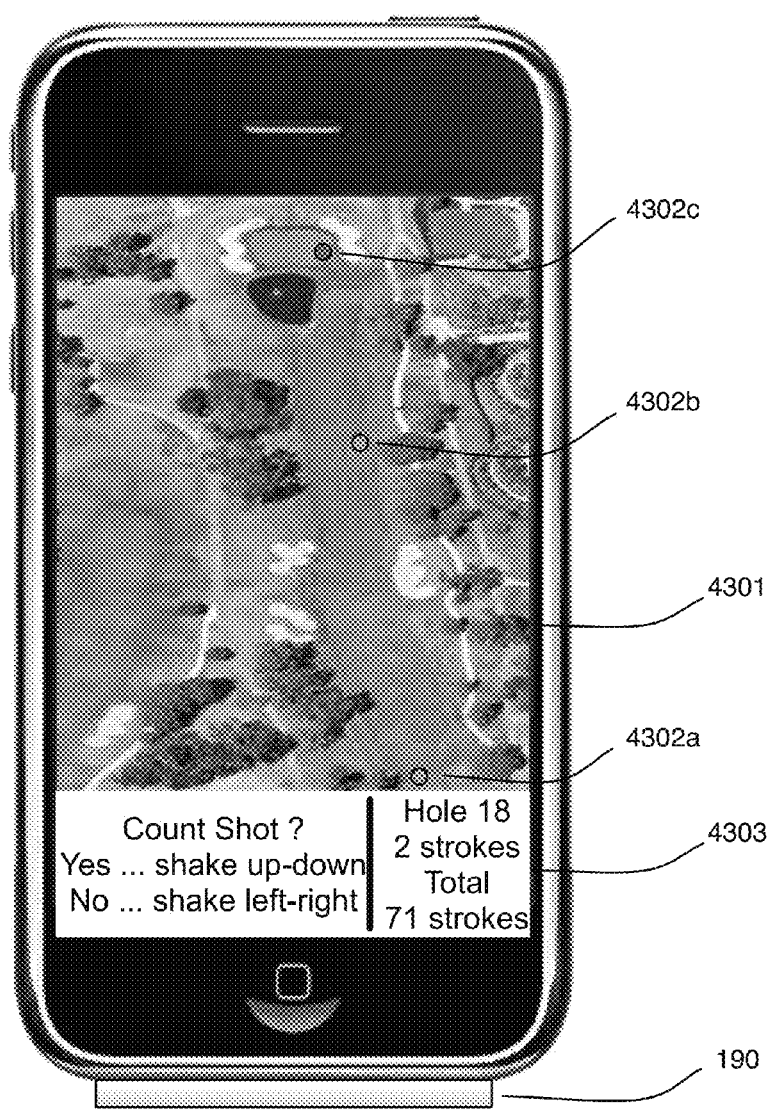
FIG. 43A shows a user interface that displays a query to the golfer to enable the golfer to count a shot or not.
Figure 44:
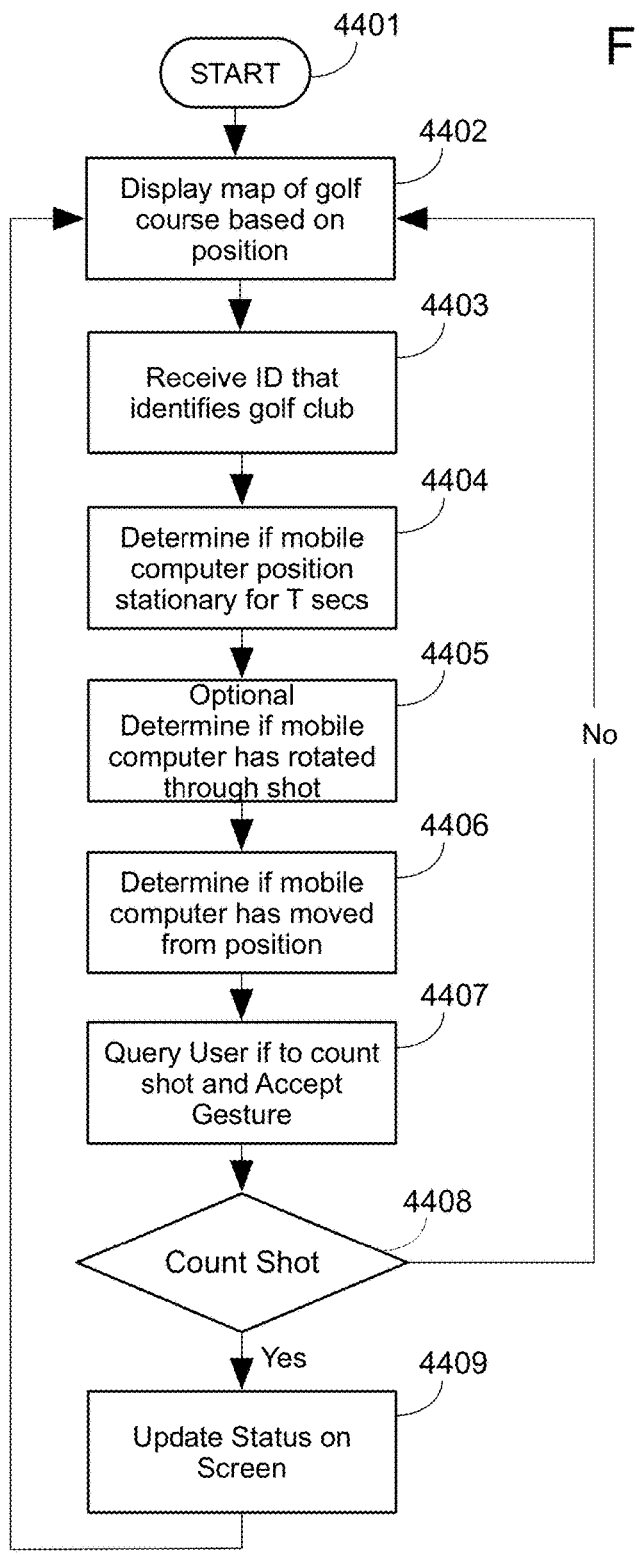
FIG. 44 shows a flow chart of an embodiment of the functionality specifically programmed into the mobile device in order to intelligently determine whether to query a golfer to count a shot and to record shots that are so designated.

FIG. 43A shows a user interface that displays a query to the golfer to enable the golfer to count a shot or not. As shown, map 4301 may show a satellite image of the location of the mobile computer as determined for example by a GPS chip in the mobile computer or via triangulation of a wireless or phone signal. Shots 4302*a* and 4302*b* may be shown in any manner to signify that these shots have been counted at the particular location. Lines may optionally be drawn between shots for example. Optionally, these shot displays may include the club number or any other desired information where a shot has taken place and been counted. Potential shot 4302*c* may be shown in any other manner which signifies that the shot is under consideration for a counted shot, as the mobile computer is currently querying the user as to whether or not to count the shot as is shown on the left side of status display 4303, i.e., "Count Shot?". The mobile computer may accept any type of input for counting the shot including audio or tactile input based input, including motion sensing of the mobile computer to determine if the user has for example input a gesture such as a shake left/right meaning "no", do not count the shot, or a shake up/down meaning "yes" count the shot. This allows for operation of the mobile computer without removal of gloves as many mobile computers require direct skin contact to effect input. In addition, as shown if the shot is counted, the total number of shots on the course may be updated as per the right side of status display 4303. The logic for determining whether to query the user is shown in FIG. 44. If the shot is counted the shot display at 4302*c* for example may be shown in a different manner that signifies that indeed, the shot has been counted. For embodiments of the invention that utilize passive RFID sensors, the processing and logic of whether to count the shot requires no electronics at all on the golf club that require local power. For example, passive RFID chips can be powered remotely via RFID reader 190 that couples to the mobile computer for example. In this manner, all complexity of known systems for counting shots including utilization of switches, solar cells, buttons, battery operated electronics is completely eliminated. An RFID marker that is passive may be attached in any manner to a golf club, include adhering the RFID marker to the shaft or under the handle or in any other position on the club. In one or more embodiments a set of RFID tape strips may be purchased by the golfer and attached to the clubs wherein the mobile computer may query the user for which club number corresponds to which RFID tag for example. Alternatively the tape strips for example that attach RFID element 191 to the golf club (see FIG. 1), may already have a club number associated with each RFID element, for example a number written on the tag or packing of each tag. Alternatively, the mobile computer may also utilize motion capture data for embodiments that include motion capture elements on clubs in order to determine when a shot or potential shot has taken place. RFID or any other identification technology may be utilized to associate not only a golf club but any other type of equipment for example with a motion capture element so that motion can be quantified by the object that is being moved.

Figure 43B:
FIG. 43B shows a user interface that displays a map of the golf course and locations of golf shots along with the particular club used at each shot location.

FIG. 43B shows a user interface that displays a map of the golf course and locations of golf shots along with the particular club used at each shot location on two different types of mobile computers. As shown, shot 4302*b* is annotated with "4 iron" and "210 yards" and a metric or score of the stroke in terms of efficiency or power (see FIG. 43C). Status area 4310 allows for displaying hole by hole shots for example. In this embodiment, it is not required that the mobile computers obtain an identifier from each club in a passive manner, but may obtain the identifier for each club via active wireless technologies if desired. Alternatively, the mobile computers shown in FIG. 43B may couple with an RFID or other passive reader (see element 190 in FIG. 43A for example).

Figure 43C:
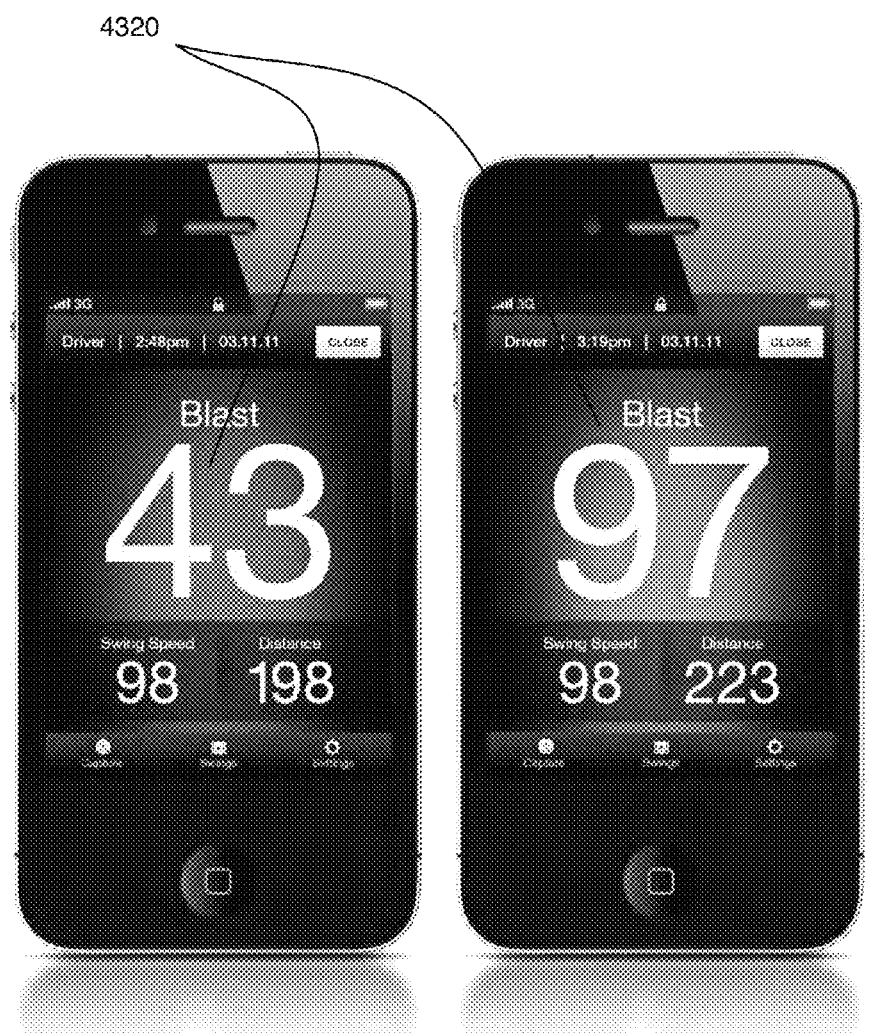
FIG. 43C shows a user interface that displays a metrics associated with each shot at each of the locations shown in FIGS. 43A and 43B.

FIG. 43C shows a user interface that displays a metrics 4320 associated with each shot at each of the locations shown in FIGS. 43A and 43B. This display may be shown for example after the golfer counts a golf shot, for example by shaking the mobile computer or otherwise asserting that the golf shot should count. This display may be shown first or after the map shots as per FIGS. 43A and 43B, or may be shown after a delay of showing the map shots, or in any other manner. The display may be color coded to show a powerful or efficient shot as shown in the right picture, or to show a less powerful or less efficient shot, i.e., background of the display may be color coded or any portion of the display may be color coded for example.

FIG. 44 shows a flow chart of an embodiment of the functionality specifically programmed into the mobile device in order to intelligently determine whether to query a golfer to count a shot and to record shots that are so designated. Processing starts at 4401, for example when a golfer initializes the shot count application on the mobile computer (see FIG. 1 as well for different embodiments of the mobile computer). The mobile computer may display a map at 4402 as obtained for example over the Internet or stored locally based on a GPS position determined by the mobile computer (or by known triangulation techniques as previously described). The mobile computer may then read an identifier associated with a club at 4403. The mobile computer may utilize RFID reader 190, or for embodiments that do not utilize RFID, may use BLUETOOTH® for example to read an identifier for a club from the motion capture element if one exists. If multiple clubs are within range, then the system may query the user as to which club, or the club with the strongest signal may be automatically chosen for example. Any other method of arbitrating the identifier of the club is in keeping with the spirit of the invention. For example, RFID reader 190 may be purposefully limited in range so that only a club in near proximity to the mobile computer, as worn for example by the golfer, is readable. This embodiment requires no power, switches or batteries on each golf club and therefore is much simpler to maintain and use than known solutions for counting golf shots. If the mobile computer is stationary for a threshold T amount of time at 4404, then the mobile computer may either optionally determine if the mobile computer has rotated or moved in a manner that is indicative of a golf swing or putt at 4405, or simply wait until the mobile computer has moved from the current position at 4406 for example, which occurs once a golfer has finished a shot or putt. For example, current mobile computers may be equipped with motion detection elements internally, and which are therefore able to determine if a user has rotated (for a driver) or translated slightly (for a putter) for example, and determine that a shot (or practice swing/shot) has occurred. The mobile computer then queries the golfer at 4407 as to whether or not to count the shot and accepts any desired input gesture to indicate whether to count or not count the shot. For example, by allowing the user to input a shake or rotation of the mobile computer, that commonly have orientation and motion sensors built in, then the golfer is not required to take any gloves off, which is generally required to activate the touch screen features of some mobile computers. Querying the user may include use of a vibration component in the mobile computer, i.e., so that no sound is required to query the golfer, which may upset other golfer attempting to concentrate. If the golfer determines that the golf shot should be counted, then the status of the shot may be updated to indicate that the shot has counted, and for example the location on the course where the shot occurred. Embodiments that utilize motion capture elements can also optionally utilize this method to count shots and in addition may include other steps that detect the signature vibrations of a golf club to determine if a golf ball has been struck as well, etc., as explained below (see also FIGS. 45-49). Identifiers associated with the motion capture elements in these embodiments may be used in place of, or in combination with RFID associated identifiers to signify the type of club and/or club number of the golf club for example. In addition, processing continues at 4402 where the map is updated as the golfer moves until another club identifier is received at 4403 for example. If the shot is not to count as per 4408, then processing continues at 4402 without any update of the total shot count and the queried shot display, for example at 4302c may be removed from the display (see FIG. 43). Other embodiments may utilize a starting zone for each hole of a golf course or may allow other inputs for the golfer to signify which hole the shot is to count for. By saving all of the locations of the shots and the club number of each shot, statistics may be derived for later display by the golfer, either on the mobile computer or uploaded to a website for example. Any other method of displaying the shots as obtained by embodiments of the invention is in keeping with the spirit of the invention.

Figure 45:
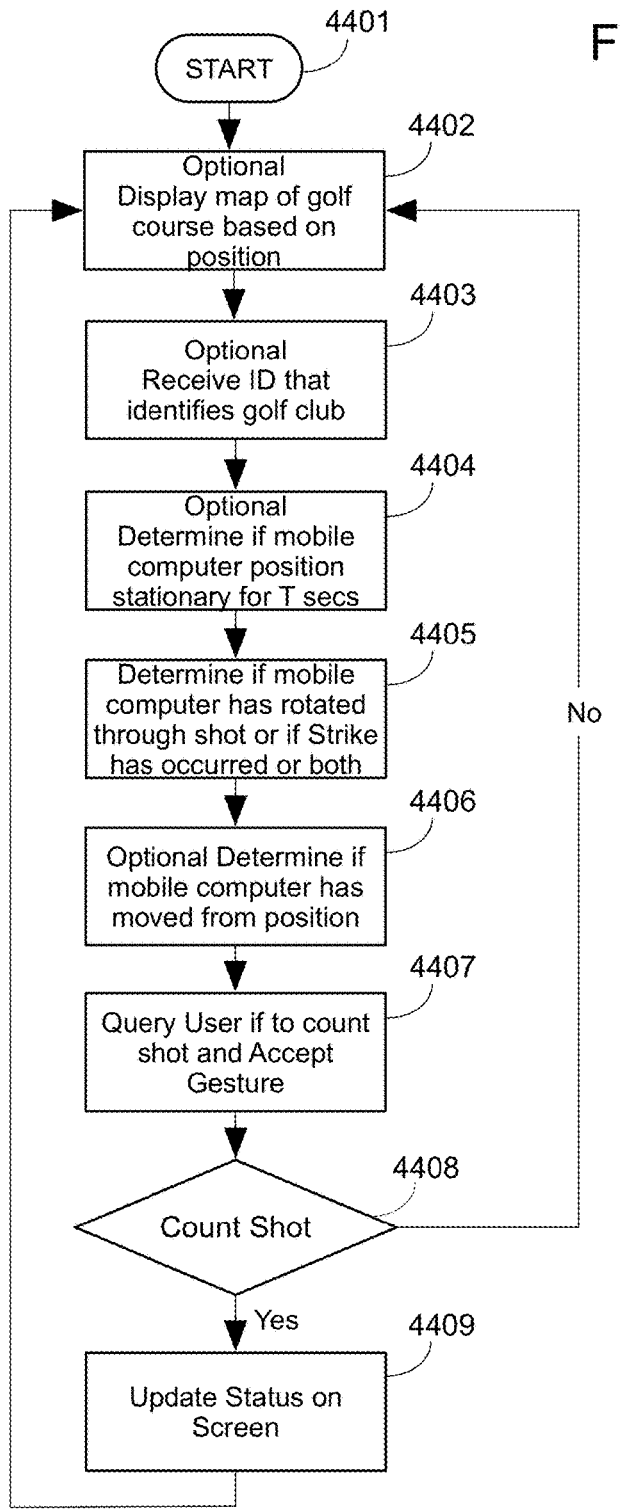
FIG. 45 shows a flow chart of an embodiment of the functionality specifically programmed into the mobile computer and/or motion capture element microcontroller in order to intelligently determine whether to query a golfer to count a shot and to record shots that are so designated.

FIG. 45 shows a flow chart of an embodiment of the functionality specifically programmed into the mobile computer and/or motion capture element microcontroller 3802 in order to intelligently determine whether to query a golfer to count a shot and to record shots that are so designated. Processing starts at 4401, for example when a golfer initializes the shot count application on the mobile computer (see FIG. 1 as well for different embodiments of the mobile computer), or for embodiments where the motion capture element stores data for an entire round without interfacing with a mobile computer, when the motion capture element moves. The mobile computer, if one is utilized at the time, may display a map at 4402 as obtained for example over the Internet or stored locally based on a GPS position determined by the mobile computer (or by known triangulation techniques as previously described). The mobile computer, again if one is being utilized at the time, may then read an identifier associated with a club at 4403. The mobile computer may utilize RFID reader 190, or for embodiments that do not utilize RFID, may use BLUETOOTH® for example to read an identifier for a club from the motion capture element if one exists. If multiple clubs are within range, then the system may query the user as to which club, or the club with the strongest signal may be automatically chosen for example. Any other method of arbitrating the identifier of the club is in keeping with the spirit of the invention. For example, RFID reader 190 may be purposefully limited in range so that only a club in near proximity to the mobile computer, as worn for example by the golfer, is readable. Optionally, if the mobile computer, if one is being used, is stationary for a threshold T amount of time at 4404, then the mobile computer may either optionally determine if the mobile computer has rotated or moved in a manner that is indicative of a golf swing or putt at 4405, or if a strike has occurred (see FIGS. 46-48) or simply optionally wait until the mobile computer has moved from the current position at 4406 for example, which occurs once a golfer has finished a shot or putt. For example, current mobile computers may be equipped with motion detection elements internally, and which are therefore able to determine if a user has rotated (for a driver) or translated slightly (for a putter) for example, and determine that a shot (or practice swing/shot) has occurred. Embodiments of the invention may also check for rotation or movement of the mobile computer and/or check for a strike alone or in combination. Embodiments of the invention may also check for both a rotation or movement indicative of a shot and a strike occurrence from a motion capture element to indicate that a shot has occurred for a robust embodiment. Alternatively, the motion capture element alone may be utilized to determine if a strike has occurred, which represents a potential shot to count. See FIGS. 46-48 for example. The mobile computer then queries the golfer at 4407 as to whether or not to count the shot and accepts any desired input gesture to indicate whether to count or not count the shot. For example, by allowing the user to input a shake or rotation of the mobile computer, that commonly have orientation and motion sensors built in, then the golfer is not required to take any gloves off, which is generally required to activate the touch screen features of some mobile computers. Querying the user may include use of a vibration component in the mobile computer, i.e., so that no sound is required to query the golfer, which may upset other golfer attempting to concentrate. If the golfer determines that the golf shot should be counted, then the status of the shot may be updated to indicate that the shot has counted, and for example the location on the course where the shot occurred. In addition, processing continues at 4402 where the map is updated as the golfer moves until another club identifier is received at 4403 for example. If the shot is not to count as per 4408, then processing continues at 4402 without any update of the total shot count and the queried shot display, for example at 4302*c* may be removed from the display (see FIG. 43). Other embodiments may utilize a starting zone for each hole of a golf course or may allow other inputs for the golfer to signify which hole the shot is to count for. By saving all of the locations of the shots and the club number of each shot, statistics may be derived for later display by the golfer, either on the mobile computer or uploaded to a website for example. Any other method of displaying the shots as obtained by embodiments of the invention is in keeping with the spirit of the invention.

One or more embodiments of the motion capture element collect, store, transmit and analyze data as follows. In one or more embodiment, one or more of the sensors in the motion capture element are placed in a data collection mode. While in the data collection mode, the motion capture element may continuously record sensor data in memory.

Figure 46:
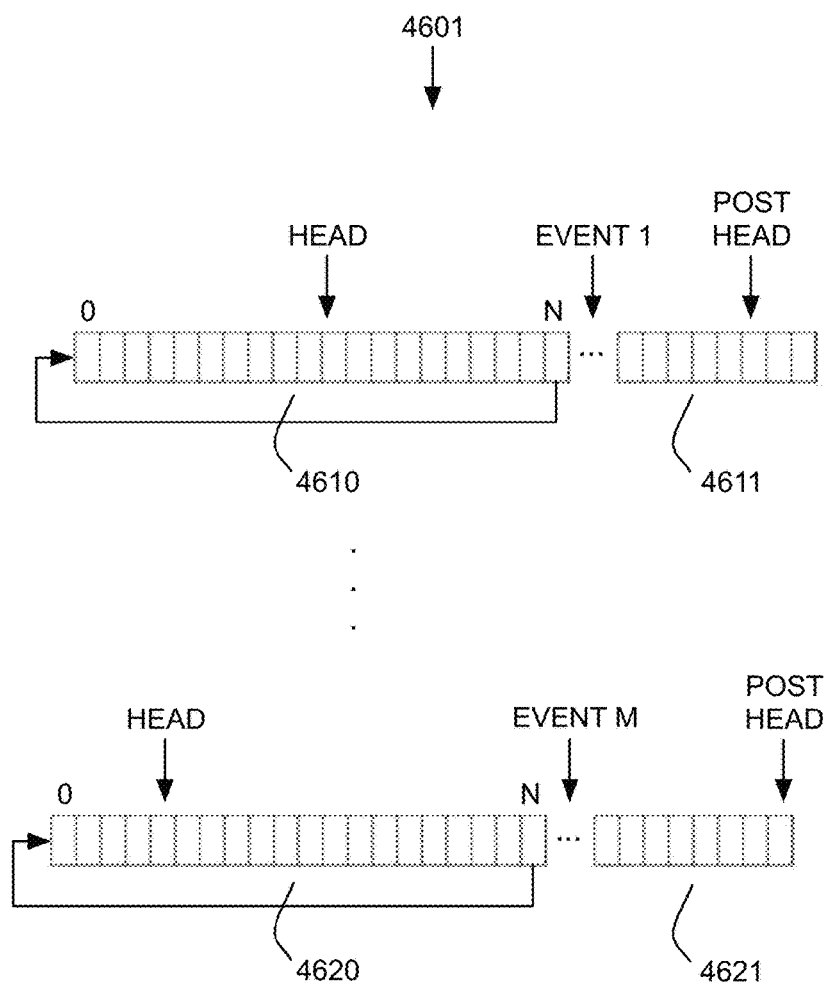
FIG. 46 illustrates an embodiment of the memory utilized to store data.

FIG. 46 illustrates an embodiment of the memory utilized to store data. Memory 4601 may for example be integral to microcontroller 3802 in FIG. 38 or may couple with the microcontroller, as for example a separate memory chip (not shown in FIG. 38 as one skilled in the art will recognize that microcontroller 3802 may attach to a separate memory chip or external memory over radio/antenna 3803 that may be located anywhere). Memory 4601 as shown collectively in FIG. 46 may be configured to include one or more memory buffer 4610, 4611 and 4620, 4621 respectively. One embodiment of the memory buffer that may be utilized is a ring buffer. The ring buffer may be implemented to be overwritten multiple times until an event occurs. The length of the ring buffer may be from 0 to N memory units. There may for example be M ring buffers, for M strike events for example. The number M may be any number greater than zero. In one or more embodiments, the number M may be equal to or greater than the number of shots for a round of golf, or any other number for example that allows all motion capture data to be stored on the motion capture element until downloaded to a mobile computer or the Internet after one or more shots. In one embodiment, a pointer, for example called HEAD keeps track of the head of the buffer. As data is recorded in the buffer, the HEAD is moved forward by the appropriate amount pointing to the next free memory unit. When the buffer becomes full, the pointer wraps around to the beginning of the buffer and overwrites previous values as it encounters them. Although the data is being overwritten, at any instance in time (t), there is recorded sensor data from time (t) back depending on the size of the buffer and the rate of recording. As the sensor records data in the buffer, an "Event" in one or more embodiments stops new data from overwriting the buffer. Upon the detection of an Event, the sensor can continue to record data in a second buffer 4611 to record post Event data, for example for a specific amount of time at a specific capture rate to complete the recording of a prospective shot. Memory buffer 4610 now contains a record of data for a desired amount of time from the Event backwards, depending on the size of the buffer and capture rate along with post Event data in the post event buffer 4611.

For example, in a golf swing, the event can be the impact of the club head with the ball. Alternatively, the event can be the impact of the club head with the ground, which could give rise to a false event. In other embodiments, the event may be a shot fired from a weapon, or a ball striking a baseball bat or when a user moves a weight to the highest point and descends for another repetition. The Pre-Event buffer stores the sensor data up to the event of impact, the Post-Event buffer stores the sensor data after the impact event. One or more embodiments of microcontroller 3802 are configured to analyze the event and determine if the event is a repetition, firing or event such as a strike or a false strike. If the event is considered a strike, and not a false strike, then another memory buffer 4620 is used for motion capture data up until the occurrence of a second event. After that strike occurs, the post event buffer 4621 is filled with captured data.

Specifically, sensor 3801 may be implemented as one or more MEMs sensors. The sensors may be commanded to collect data at specific time intervals. At each interval, data is read from the various MEMs devices, and stored in the ring buffer. A set of values read from the MEMs sensors is considered a FRAME of data. A FRAME of data can be 0, 1, or multiple memory units depending on the type of data that is being collected and stored in the buffer. A FRAME of data is also associated with a time interval. Therefore frames are also associated with a time element based on the capture rate from the sensors. For example, if each Frame was filled at 2 ms intervals, then 1000 FRAMES would contain 2000 ms of data (2 seconds). In general, a FRAME does not have to be associated with time.

Data can be constantly stored in the ring buffer and written out to non-volatile memory or sent over a wireless or wired link over radio/antenna 3803 to a remote memory or device for example at specified events, times, or when communication is available over radio/antenna 3803 to a mobile device or any other computer or memory, or when commanded for example by a mobile device, i.e., "polled", or at any other desired event.

Figure 47:
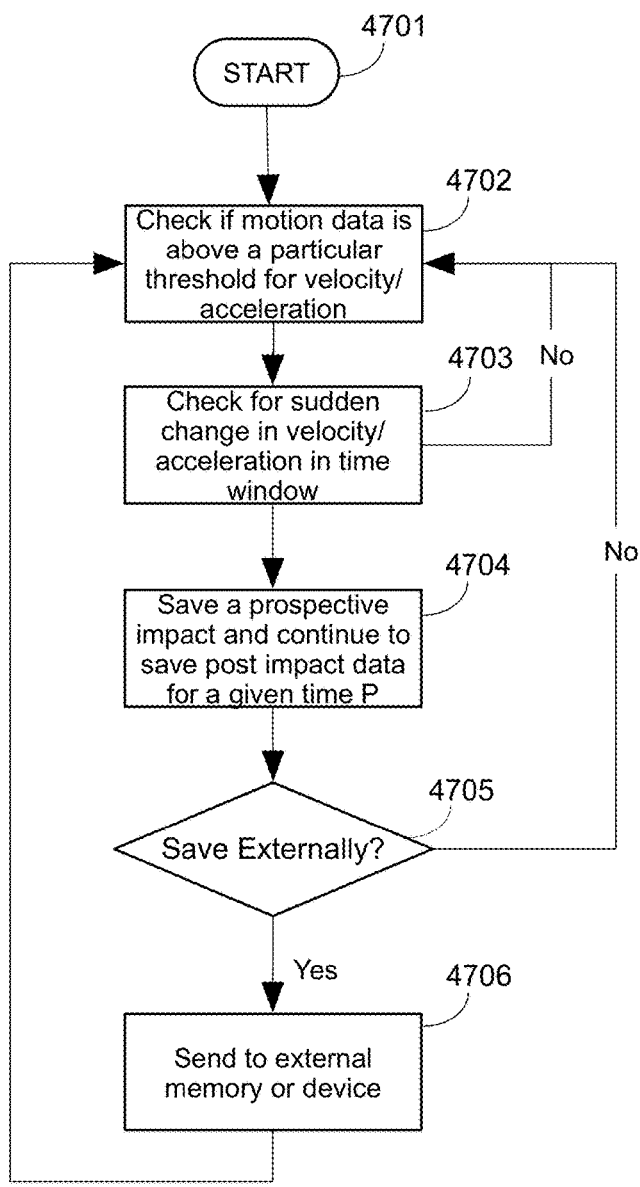
FIG. 47 shows a flow chart of an embodiment of the functionality specifically programmed into the microcontroller to determine whether a prospective strike has occurred.

FIG. 47 shows a flow chart of an embodiment of the functionality specifically programmed into the microcontroller to determine whether an event that is to be transmitted for the particular application, for example a prospective event or for example a strike has occurred. The motion, acceleration or shockwave that occurs from an impact to the sporting equipment is transmitted to the sensor in the motion capture element, which records the motion capture data as is described in FIG. 46 above. Microcontroller 3802 is configured to then analyze the event and determine whether the event is a prospective strike with a ball for example or not.

One type of event that occurs is a strike of the clubface when it impacts a golf ball. In other sports that utilize a ball and a striking implement, the same analysis is applied, but tailored to the specific sport and sporting equipment. In tennis a prospective strike can be the racquet hitting the ball, for example as opposed to spinning the racquet before receiving a serve. In other applications, such as running shoes, the impact detection algorithm can detect the shoe hitting the ground when someone is running. In exercise it can be a particular motion being achieved, this allows for example the counting of repetitions while lifting weights or riding a stationary bike.

For golf related scenarios, microcontroller 3802 is configured to analyze the motion capture data to determine when the golf club for example has impacted an object, such as but not limited to a golf ball, tee, or the ground. The impact shock wave at the club head is transmitted to the sensor. In one or more embodiments of sensor 3801, position, orientation, velocity and/or accelerometer data is collected to sense these quantities with respect to one or more axes, for example accelerations on three accelerometer axes. Since all impacts are recorded, such as an impact of the club with a tee or the ground, the impacts are next analyzed to determine if the strike is valid or not valid with respect to a strike of a golf ball.

In one or more embodiments of the invention, processing starts at 4701. Microcontroller 3802 compares the motion capture data in memory 4610 with linear velocity over a certain threshold at 4702, within a particular impact time frame and searches for a discontinuity threshold where there is a sudden change in velocity or acceleration above a certain threshold at 4703. If no discontinuity in velocity or for example acceleration occurs in the defined time window, then processing continues at 4702. If a discontinuity does occur, then the prospective impact is saved in memory and post impact data is saved for a given time P at 4704. For example, if the impact threshold is set to 12 G, discontinuity threshold is set to 6 G, and the impact time frames is 10 frames, then microcontroller 3802 signals impact, after detection of a 12 G acceleration in at least one axis or all axes within 10 frames followed by a discontinuity of 6 G. In a typical golf swing, the accelerations build with smooth accelerations curves. Impact is signaled as a crash and quick change in acceleration/velocity. These changes are distinct from the smooth curves created by an incrementally increasing or decreasing curves of a golf swing. If data is to be saved externally as determined at 4705, i.e., there is a communication link to a mobile device and the mobile device is polling or has requested impact data when it occurs for example, then the impact is transmitted to an external memory, or the mobile device or saved externally in any other location at 4706 and processing continues again at 4702 where microcontroller 3802 analyzes collected motion capture data for subsequent impacts. If data is not to be saved externally, then processing continues at 4702 with the impact data saved locally in memory 4601. In one or more embodiments of the invention, noise may be filtered from the motion capture data before sending, and the sample rate may be varied based on the data values obtained to maximize accuracy. For example, some sensors output data that is not accurate under high sampling rates and high G-forces. Hence, by lowering the sampling rate at high G-forces, accuracy is maintained. In one or more embodiments of the invention, the microcontroller associated with motion capture element 111 may sense high G forces and automatically switch the sampling rate. In one or more embodiments, instead of using accelerometers with 6 G/12 G/24 G ranges or 2 G/4 G/8 G/16 G ranges, accelerometers with 2 ranges, for example 2 G and 24 G may be utilized to simplify the logic of switching between ranges.

The impact event is defined in one embodiment, as all accelerometer axes reaching an impact threshold G force within a specified time frame, called the impact time frame. This alone is not sufficient to detect impact since a fast swing could reach the impact threshold, i.e., without contacting the golf ball, for example a practice swing. The discontinuity threshold signals the rapid change of accelerometer values that signify sudden impact. The impact time frame may be implemented as a sliding window that defines a time frame in which impact is detected. If the impact threshold and discontinuity threshold are reached on all axes within the impact time frame, then impact is signaled and the event as shown in FIG. 46, for example Event 1, is saved and data is then collected in the next memory buffer. One or more embodiments of the invention may transmit the event to a mobile device and/or continue to save the events in memory, for example for a round of golf or until a mobile device communication link is achieved.

For example, if impact threshold for X is reached at time t, and impact threshold Y is reached at time t+n, and t+n is outside the impact time frame, then no impact is detected. For example, practice swings do not trigger impact events.

In one or more embodiments of the invention, further analysis of the impact event occurs to reduce false positives of impact events. As described, microcontroller 3802 searches for a linear velocity to reach a certain threshold, and a discontinuity in the linear velocity. Hence, microcontroller 3802 will not trigger an impact in a full motion swing where there is no "crash" or physical impact. However, a prospective impact event will trigger if the club is tapped on the ground or against any other object. However, since a typical golf swing has a very characteristic angular and linear velocity signature, the motion capture data may be utilized to determine whether the prospective impact was a result of a typical golf swing. For example, microcontroller 3802 may compare the motion capture data with this signature to predict the occurrence of a typical golf swing, in order to classify the impact as a valid golf club and golf ball impact.

Figure 48:
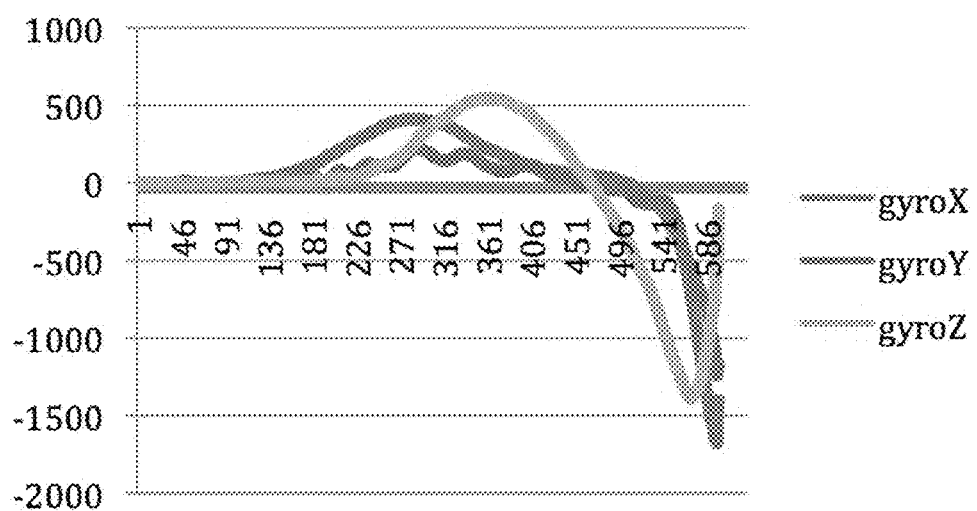
FIG. 48 illustrates a typical golf swing signature, which is compared to motion capture data to eliminate false positive impact events.

For example, with the sensor mounted in the handle, a typical golf swing signature is shown in FIG. 48. In one or more embodiments, microcontroller 3802 is configured to execute a pattern matching algorithm to follow the curves for each of the axis and use segments of 1 or more axis to determine if a characteristic swing has taken place. If the motion capture data in memory 4601 is within a range close enough to the values of a typical swing as shown in FIG. 48, then the motion of the club is consistent with a swing, whether a practice swing or swing that results in an impact with a golf ball. For example, axis-X shows a climb between frame 161 to 289, followed by a steep decline between 545 to 577. Microcontroller 3802 utilizes this information to recognize that there is a backswing, followed by a downswing. If this occurs and an impact occurs as described with respect to FIG. 47, then a valid golf club and golf ball impact is signaled. Microcontroller 3802 may also utilize the time between a backswing and downswing events to validate that a swing has taken place. Embodiments of the invention thus reduce the number of false positives in impact detection, after first characterizing the angular and/or linear velocity signature of the movement, and then utilizing elements of this signature to determine if similar signatures for future events have occurred.

The motion capture element collects data from various sensors. The data capture rate is high and there is significant amounts of data that is being captured. Embodiments of the invention may use both lossless and lossy compression algorithms to store the data on the sensor depending on the particular application. The compression algorithms enable the motion capture element to capture more data within the given resources. Compressed data is also what is transferred to the remote computer(s). Compressed data transfers faster.

Compressed data is also stored in the Internet "in the cloud", or on the database using up less space locally.

Over the air programming is enabled in one or more embodiments of the invention to enable the update of the firmware stored in the motion capture element. An initial bootloader is stored in non-volatile memory on the motion capture element that provides the basic services to communicate with a remote system. There is also a dual image storage capability on the module. Once an application image is loaded, a CRC check may be performed against the newly downloaded image. If the downloaded firmware passes the various checks, then the microcontroller boots from the new image, and the old image is flagged old. In one or more embodiments of the invention an external dongle may be utilized to transfer data from the motion capture element to the mobile computer via Infrared as opposed to over a typical radio frequency link. Any other method of transferring data between the motion capture elements and the mobile computer is in keeping with the spirit of the invention.

FIG. 49A-B illustrate two trajectories in the motion capture data that may be interpolated or otherwise averaged to create a more accurate or smoother trajectory for example or to otherwise smooth the trajectory for any other purpose. Backswing 4902 begins at "address" with the golf club head near the ball as shown at the bottom of FIG. 49A. Swing 4901 begins at the top of the swing point and follows through the impact start point and continues along. The integration path of the swing is shown as trajectory 4903*a*. FIG. 49B shows the integrated path or otherwise interpolated trajectory 4903*b* that results by averaging points from the backswing and swing.

Specifically, the process of computing a swing trajectory, for exemplary purposes only a golf swing trajectory (x, y, z position of the club head through time) is based on integrating the sensor linear acceleration data twice to produce the position of the sensor in world space, then transforming the sensor motion to the corresponding motion at the club head using rigid body mechanics (RBM) or a combination of RBM and flex modeling. In many cases the sensor linear accelerometer errors are too large to accurately reproduce the club head position through the time period of a golf swing using straight-forward integration from the initial address position. Thus embodiments of the microcontroller coupled with the sensor may utilize the following technique for adjusting the trajectory that results from integrating the sensor linear accelerometer to provide a more accurate trajectory in the neighborhood of the impact.

One or more embodiments of the sensor are configured to detect impact. So for the golf swings of interest it is safe to assume that the player stuck the ball. If we further assume that the golfer lined up on the ball at the "address" position, then it follows that the position of the club head at impact is within a small, e.g., on the order of inches, range of the club head position at address.

Embodiments of the invention may utilize this knowledge to improve the trajectories using the following process.

1. Compute the trajectory of the club head by straight-forward integration of the sensor data and combining with RBM/Flex modeling. This is designated Trajectory 1.

2. Take the following data from Trajectory 1 as initial conditions for a second integration step:
The position of the club head at time of address.
The orientation of the club head at time of impact.

3. Using the initial conditions described in step (2) embodiments of the microcontroller or other computing element, integrate backward in time through the sensor linear accelerometer data to produce Trajectory 2.

4. Both these trajectories are valid representations of the golf swing subject to the assumption that the address position and impact position are the same. Of course there will be slight differences in these two positions, however the result of blending these two trajectories generally gives less error than straightforward integration of the linear accelerometer data.

The two trajectories are then combined into a single Trajectory with a straight-forward linear blending:

$$X(t)=w(t)X1(t)+(1-w(t))X2(t).$$

$$Y(t)=w(t)Y1(t)+(1-w(t))Y2(t).$$

$$Z(t)=w(t)Z1(t)+(1-w(t))Z2(t).$$

where subscripts 1 and 2 indicate Trajectory 1 and Trajectory 2 respectively. The weight w(t) is a blending parameter that varies linearly with time between 0 and 1 such that $w(t0)=1$ and $w(t_{impact})=0$.

For cases where the assumptions about address and impact position are within a predetermined threshold or range, this method provides an excellent qualitative correction to the golf swing trajectory. This is particularly valuable for use in creating blended animations of a golfer's swing that are characteristic of the actual swings in a library of collected data or other database for example.

One or more embodiments of the system may use multiple sensors to measure a single physical quantity such as acceleration. Using more than one sensor to measure a quantity may provide benefits such as greater accuracy and a larger effective measurement range. For example, one or more embodiments may combine a sensor with a relatively low measurement range, but with fine resolution within this range, with a sensor with a higher measurement range and a coarser resolution. This combination may for example provide highly accurate readings within the low range, but also provide valid data when the measured value exceeds the limited range of the fine resolution sensor.

FIG. 50 shows a conceptual block diagram of an illustrative embodiment that combines a low-range accelerometer and a high-range accelerometer. Use of multiple accelerometers is illustrative; one or more embodiments may use multiple sensors for any physical quantity, not limited to acceleration. For example, without limitation, one or more embodiments may use multiple sensors to measure one or more of position, orientation, linear velocity, linear acceleration, angular velocity, angular acceleration, or any function of any of these quantities. For example, one or more embodiments may have multiple gyroscopes instead of or in addition to multiple accelerometers. One or more embodiments may use any number of sensors, not limited to two, to measure a single physical quantity.

In the example shown in FIG. 50, motion capture element 111 measures motion of equipment 110 used by user 150. The motion capture element includes a microprocessor 5001, a memory 5002, and a communications interface 5003 for transmitting sensor data to other subsystems. In this illustrative example, the motion capture element 111 includes three sensors: a low-range accelerometer 5011, a high-range accelerometer 5012, and a rate gyroscope 5013. These sensors are illustrative; one or more embodiments may have three or more accelerometers, for example, or may have multiple gyroscopes instead of or in addition to multiple accelerometers. One or more embodiments may have other sensors instead of or in addition to accelerometers and gyroscopes.

Low-range accelerometer 5011 has a measurement range 5014 with a lower measurable value of −16 g and an upper measurable value of +16 g. High-range accelerometer 5012 has a measurement range 5015 with a lower measurable value of −400 g and an upper measurable value of 400 g. These measurement ranges are illustrative; one or more embodiments may have sensors with any measurement ranges. The measurement ranges shown in FIG. 50 are symmetrical around 0 (the lower measurable value is the negative of the upper measurable value); one or more embodiments may have asymmetric measurable ranges for any sensor or sensors. For embodiments with multiple sensors that measure the same physical quantity, the measurement ranges of these sensors may be disjoint, overlapping, or nested as shown in FIG. 50.

Microprocessor 5001 collects data from sensors 5011, 5012, and 5013, stores or buffers this data in memory 5002, and transmits the data using communications interface 5003 over communications channel 5004 to a computer 160 for analysis. Communications channel 5004 may for example be a wireless link, a wired link, or a combination thereof. Computer 160 may be any device or combination of devices that can receive and process data, including for example, without limitation, a desktop computer, a laptop computer, a tablet computer, a mobile device, a smartphone, a smart watch, a microprocessor, a microcontroller, a server, or any network or combination of these devices. FIG. 50 shows illustrative sensor data 5020 transmitted from motion capture element 111 to computer 160. This data includes angular velocity 5023 obtained from gyroscope 5013, acceleration value 5021 obtained from low-range accelerometer 5011, and acceleration value 5022 obtained from high-range accelerometer 5012. In this example, the precision of low-range accelerometer reading 5021 is greater than that of high-range accelerometer reading 5022. For simplicity, sensor values are shown as having only one axis; in one or more embodiments sensors may have multiple axes reflecting for example multiple degrees of freedom for the motion of the motion capture element.

In this example, computer 160 processes sensor data 5020 in three steps. In the first step 5030, individual estimates are calculated for each of the accelerometers. In some embodiments the individual estimates may be identical to the raw sensor readings 5021 and 5022; however, one or more embodiments may further process the sensor data to obtain individual estimates for each sensor. For example, processing to form individual estimates may apply filters, smoothing, rounding, or other transformations to the data series of each individual sensor. In the example of FIG. 50, the low-accelerometer estimate 5031 and the high-accelerometer estimate 5032 are calculated in step 5030. In step 5040, the computer combines these individual estimates to generate a combined, integrated estimate of the physical quantity measured by the multiple sensors. For example, in FIG. 50 this step results in a combined estimate 5041 for acceleration. In this simple example, the combination step 5040 is a simple averaging of the two individual estimates. Other methods of combining individual estimates are described below. Finally, in step 5050 the computer analyzes the motion of the motion capture element 111 (and for example of equipment 110 to which the motion capture element may be attached). This analysis may use the raw sensor data 5020 as well as the combined estimate 5041 calculated in steps 5030 and 5040.

In the embodiment shown in FIG. 50, processing of sensor data (steps 5030, 5040, and 5050) is performed by computer 160. In one or more embodiments some or all of this processing may be performed by the microprocessor 5001 of the motion capture element 111. For example, the microprocessor 5001 may combine individual sensor estimates to form a combined estimate of a physical quantity, potentially before transferring this data to computer 160.

Figure 51:
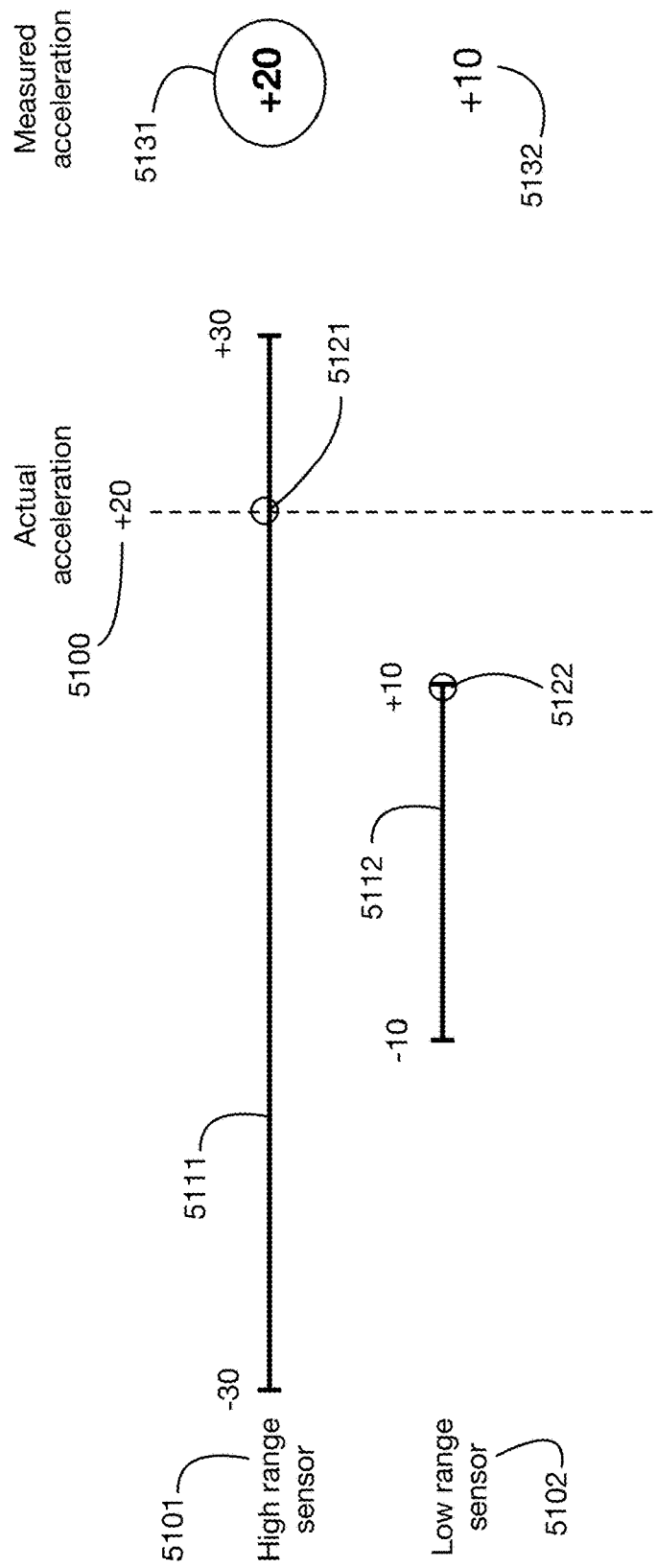
FIG. 51 illustrates an embodiment that combines measurements from multiple sensors by selecting one measurement that is in the interior of the measurement range; the sensor that reads at the upper or lower limit is ignored in this example since the value is considered potentially inaccurate when the sensor is at its limits.

In some cases, a value of a physical quantity may be outside the measurable range of one or more of the sensors. In these cases, one approach to combining individual estimates is to simply select a sensor value that is within the measurable range of the associated sensor, if such a value exists. FIG. 51 illustrates an embodiment that uses this approach. High-range sensor 5101 has measurable range 5111 (closed interval [−30, +30]), and low-range sensor 5102 has a much smaller measurable range 5112 (closed interval [−10, +10]). In this example the actual value 5100 of the physical quantity (such as acceleration, for example) is greater than the upper measurable value 5122 of the low-range sensor 5102. Therefore the low-range sensor 5102 reports only the upper measurable value 5132, since it cannot measure the true, higher value 5100. The high-range sensor reports the true value 5100 (or a value approximating this value) as measured value 5131. The computer combining the individual readings 5131 and 5132 determines that the reading 5132 is at the endpoint 5122 of the measurement range 5112, whereas the reading 5131 is in the interior of the measurement range 5111, at interior point 5121. Thus the value 5131 in the interior is selected as the combined estimate. In general, one or more embodiments may treat measured values in the interior of a sensor's measurement range (that is, strictly above the lower measurable value and strictly below the upper measurable value) as more reliable than measured values at the endpoints of the measurement range, since values at the endpoints may reflect values that are out of range and are thus unmeasurable by that sensor.

Figure 52:
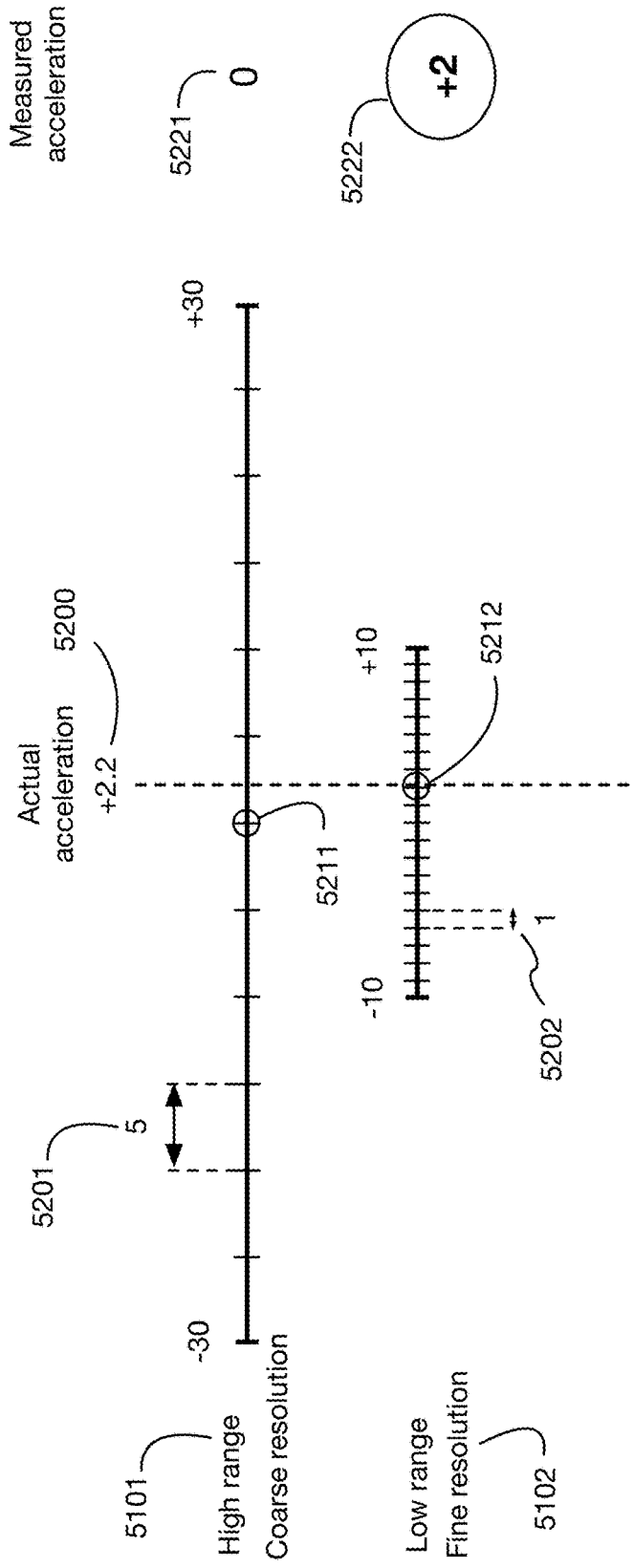
FIG. 52 shows a variation on the example of FIG. 51, where measurements are in the valid interior of the measurement range for multiple sensors; in this illustrative example the system selects the measurement with the finer resolution.

FIG. 52 extends the example of FIG. 51 for the case of a value that is in the interior of the measurement range of both sensors. As in FIG. 51, acceleration is measured by both a high-range sensor 5101 and a low-range sensor 5102. The actual value 5200 in this case is within the measurable range of both sensors. Hence both sensors can be expected to have valid measurements of the quantity 5200. In this example, the low-range sensor 5102 has a finer measurement resolution than the high-range sensor 5101: the resolution 5202 between successive measurable values for sensor 5102 is significantly smaller than the resolution 5201 between successive measurable values for sensor 5101. Because of the finer resolution, sensor 5102 may be more precise on average than sensor 5101 when the quantity 5200 is within the measurable range of sensor 5102. Thus the embodiment illustrated in FIG. 52 selects the reading 5222 from sensor 5102 rather than reading 5221 from sensor 5101 when it combines the individual estimates.

Figure 53:
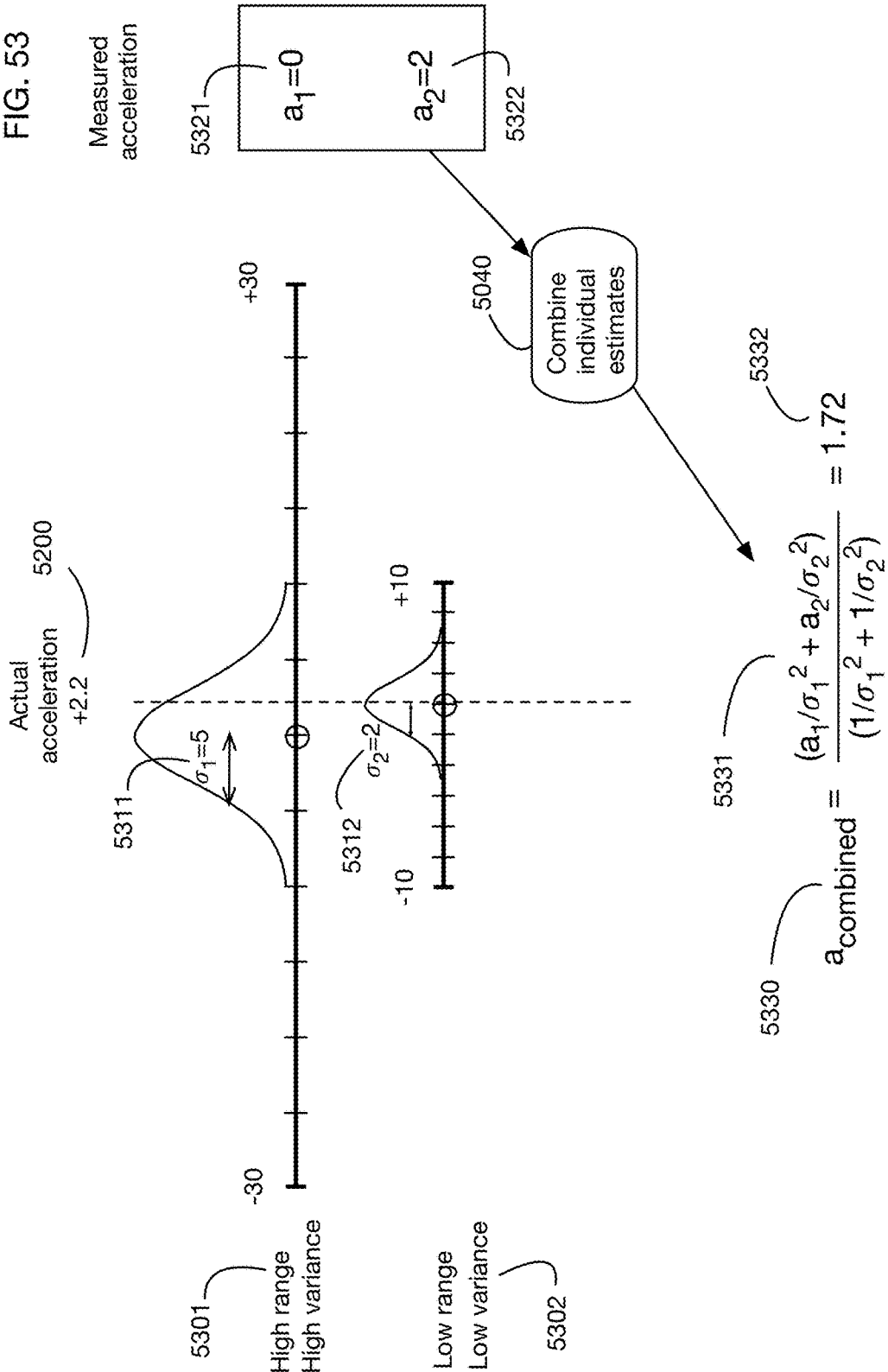
FIG. 53 shows an embodiment that combines individual sensor estimates using a weighted average, where the weights are inversely proportional to the measurement variances of the sensors.

A potential disadvantage of the simple approach illustrated in FIG. 52 of selecting the sensor reading with finer resolution is that all information from the other sensor is discarded. FIG. 53 illustrates an alternative approach that combines multiple sensor readings using a weighted average of all of the readings (when these readings are all in the interior of the measurable range of the associated sensors). In this illustrative example, the weight for each sensor reading is the inverse of the measurement variance associated with the sensor reading. This approach to weighting multiple estimates is known in the art, and corresponds for example to calculating a maximum likelihood estimate for a common value that is measured using multiple noisy measurements with errors that are normally distributed. In FIG. 53, high-range sensor 5301 has a high measurement standard deviation 5311, and low-range sensor 5302 has a lower measurement standard deviation 5312. The actual value 5200 is within the interior of the measurement range of both sensors; hence both sensor readings 5321 and 5322 are valid. The values 5321 and 5322 are combined in step 5040 by weighting each value by the inverse of the associated measurement variance. Thus the combined estimate 5330 is calculated using formula 5331, resulting in combined estimate value 5332.

In one or more embodiments the variances or standard deviations of measurements for each sensor may be known (for example from data sheets) or may be calculated for example using calibration procedures. In one or more embodiments the variances or standard deviations may be estimated for example from the sensor resolutions. For example, one or more embodiments may assume that the standard deviation of a sensor measurement is proportional to the resolution (the interval between successive measurable values), and therefore that the measurement variance is proportional to the square of the resolution. For example, as is known in the art, measurement errors uniformly distributed in an interval of length L have variance $L^2/12$. Therefore, measurement errors that are uniformly distributed across a fixed number of measurement steps result in a measurement variance that is proportional to the square of the resolution.

In one or more embodiments readings from multiple sensors that measure the same physical quantity may be compared to determine whether any or all of the sensors require recalibration. If the multiple sensors are well calibrated then on average they should measure approximately the same value (when the true value is within the measurement range of each sensor), although the variance of these measurements may differ significantly based for example on the resolution of the different sensors. However, over time one or more of the sensors may drift out of calibration, introducing for example a bias in one or more of the sensor measurements. One or more embodiments may analyze the differences in readings from two or more sensors that measure the same quantity to detect when one or more sensors go out of calibration. This analysis may be performed by the microprocessor of the motion capture element, by the computer receiving the sensor data, or by both.

Figure 54:
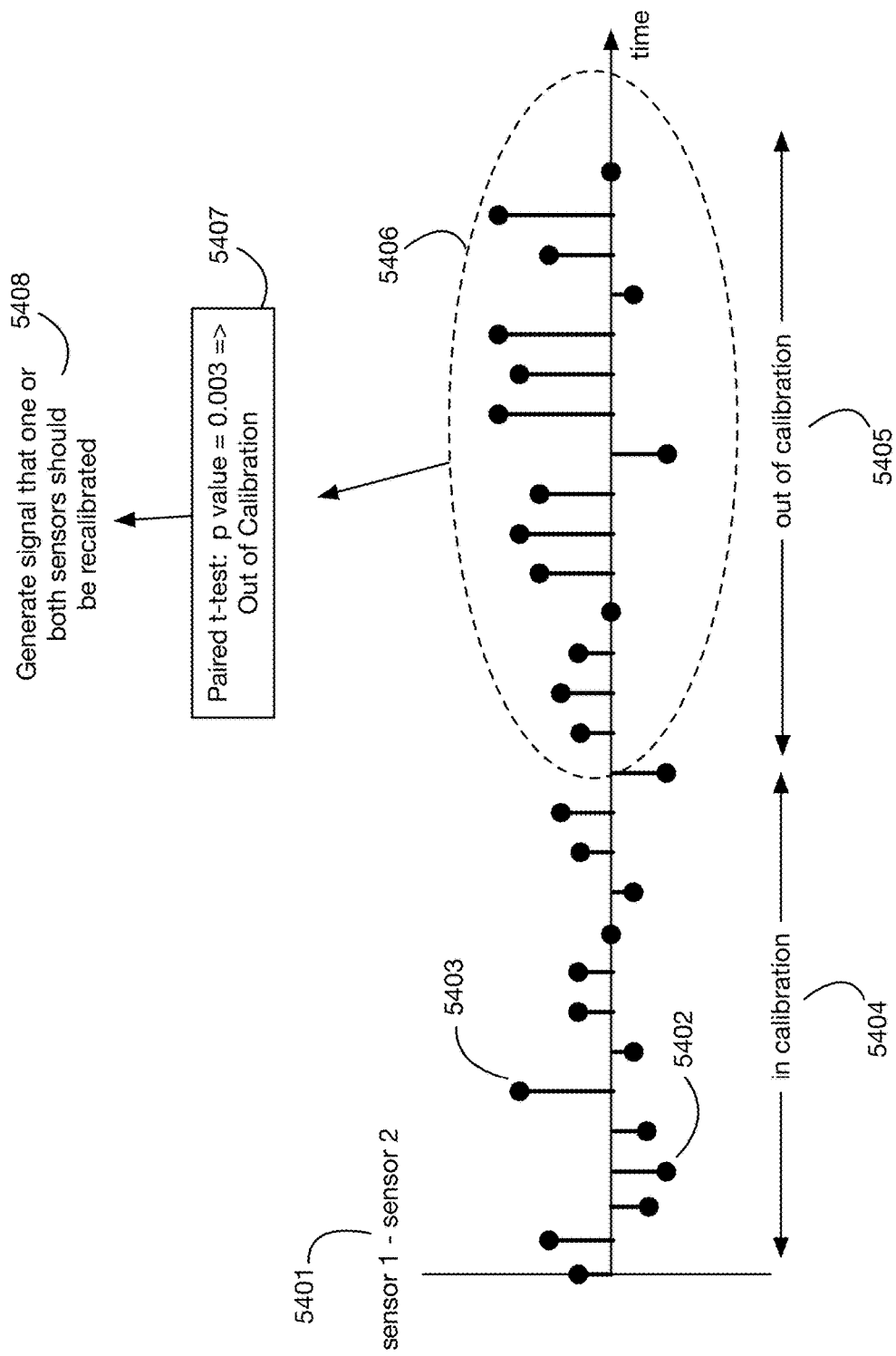
FIG. 54 illustrates an embodiment that tracks and analyzes differences in readings between two sensors over time to determine whether one or both sensors may be out of calibration.

FIG. 54 illustrates an embodiment that analyzes sensor data from dual sensors to detect an out of calibration condition. Time series 5401 represents differences between sensor readings of two sensors that each measure the same physical quantity at substantially the same time. In one or more embodiments the sensor data may be preprocessed prior to forming differences, for example to filter out samples where either or both of the sensor values are at the endpoints of their measurement ranges. Because of measurement variation and finite resolution, sensor readings of the two sensors are not always identical. For example, at sample 5402 the difference between the two sensor readings is negative, and at sample 5403 the difference is positive. However, during time period 5404, when the two sensors are in calibration, the average difference between the sensors is close to zero, indicating that there is no detectable bias in either sensor. In contrast, during period 5405 the sample differences 5406 deviate significantly from zero, indicating that one or both sensors has drifted out of calibration. One or more embodiments may for example perform statistical tests on sensor data, such as a paired t-test to test whether differences between sensor readings are statistically significantly different from zero. In the example of FIG. 54, the paired t-test 5407 indicates that the sensor value differences are significantly different from zero with a p-value of 0.003. Thus the system generates an out of calibration signal 5408, indicating that recalibration may be required. The use of a paired t-test like 5407 is illustrative; one or more embodiments may use any type of analysis or statistical tests to determine whether sensor data suggests that recalibration is indicated. In one or more embodiments the signal 5408 may trigger an automatic recalibration of one or more sensors.

Figure 55:
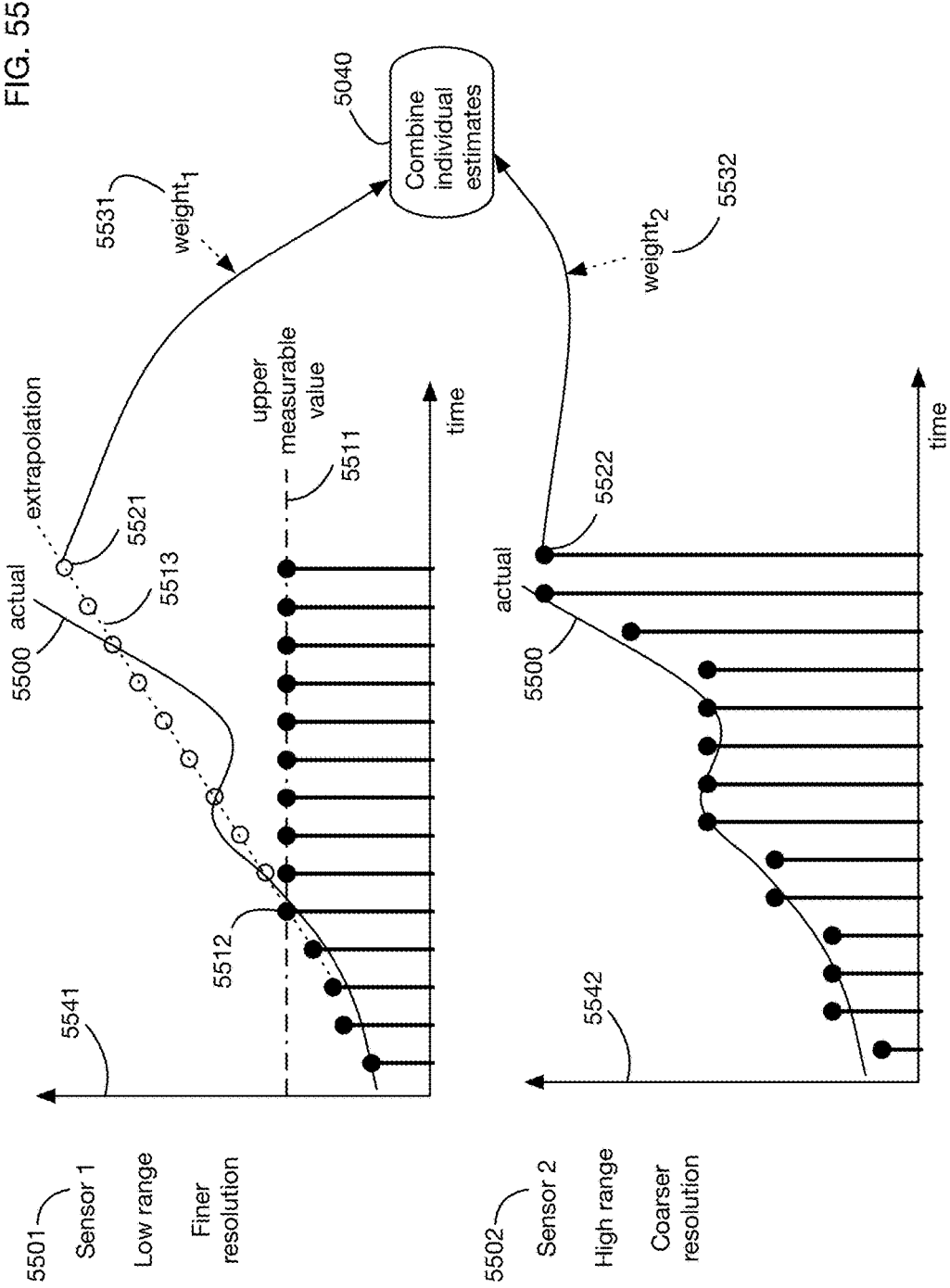
FIG. 55 illustrates an embodiment that extrapolates sensor measurements beyond the limit of the sensor's measurement range, and that combines the extrapolated measurements with measurements from another higher range sensor.

When values are outside of the measurable range of a sensor, the sensor's readings do not provide accurate indications of the values since they are limited to the upper or lower measurable values at the endpoints of the measurable range. In the embodiment illustrated in FIG. 51, sensor values at the endpoints of the measurable range are ignored if another sensor has a value in the interior of its measurement range. While this approach is straightforward, it has the drawback that data from one of the sensors is ignored. FIG. 55 illustrates a different approach that relies on extrapolating data outside the measurement range of the sensor. In this example, low-range sensor 5501 and high-range sensor 5502 measure the value of a common physical quantity. Graph 5541 shows the readings of the low-range sensor over time, and graph 5542 shows the corresponding readings of the high-range sensor over time. The actual values of the physical quantity 5500 are also shown on the graphs. Low-range sensor 5501 has an upper measurable value 5511, which is reached at sample 5512. After this sample, the true value 5500 of the quantity exceeds the upper measurable value, so the sensor reading of sensor 5501 remains fixed at the upper endpoint 5511. The high-range sensor 5502 has sufficient range to measure the quantity as it increases over the time interval, albeit at a coarser resolution. In this embodiment, sensor data from samples prior to 5512 is extrapolated to form an extrapolated curve 5513 for the low-range sensor 5501. The example shown is a simple linear extrapolation of the last 3 samples up to and including the first sample 5512 at the upper endpoint 5511. This linear extrapolation is illustrative; one or more embodiments may extrapolate sensor data using any desired technique, curve, function, or algorithm. In particular, one or more embodiments may use any polynomial function to generate an extrapolation curve, including for example, without limitation, linear functions, quadratic functions, and cubic functions.

One or more embodiments may generate an extrapolation curve using techniques such as spline fitting or regression, for example. One or more embodiments may fit extrapolation curves based on data before or after periods when sensor values are at the upper or lower endpoints of the measurable range. One or more embodiments may use knowledge of the probable or possible motions of the object to which a motion capture element is attached to generate or refine an extrapolation curve.

In the embodiment illustrated in FIG. 55, extrapolated values on line 5513 from sensor 5501 are combined with sensor readings from high-range sensor 5502 to form a combined estimate of the physical quantity. This combining step 5040 uses a weighted average of the estimates from the two sensors. For example, value 5521, which is obtained by extrapolating sensor data beyond the upper measurable value 5511, is weighted by weight 5531 and combined with sensor value 5522 weighted by weight 5532. One or more embodiments may combine extrapolated data and other sensor data in any desired manner, including but not limited to forming a weighted average of the values.

While extrapolation provides an estimate of a value beyond the measurement range of a sensor, it is subject to significant errors since the true value of the measured quantity may not follow the extrapolation curve. In some situations, the confidence in the extrapolated value may decrease as that value deviates further from the measurement range of the sensor. Therefore, one or more embodiments may assign weights to extrapolated values that for example decrease as the distance between the extrapolated value and the endpoints of the sensor's measurement range increase. FIG. 56 illustrates an example of these decreasing weights using the data from FIG. 55. For illustration, the system favors the low-range, finer resolution sensor value when that value is within the interior of the measurement range of the sensor; thus the weight for sample point 5601 is 1.0 and the weight for the corresponding value 5621 for the high-range sensor is 0.0. For extrapolated values from the low-range sensor, the weights decrease as the extrapolation curve deviates further from the sensor's range. Thus for example weights decline from 0.8 for sample 5602 to 0.2 to sample 5603. This embodiment defines a limit 5612 for extrapolation, beyond which the extrapolated values are given no weight (and thus the value from the high-range sensor is used as the combined estimate). This limit of extrapolation is set at a threshold distance 5613 from the upper measurable value 5511. A similar limit of extrapolation for example may be defined below the lower measurable value. Thus extrapolated value 5605 is given zero weight, since its distance from the upper measurable value 5511 is greater than the threshold 5613.

While the ideas herein disclosed has been described by means of specific embodiments and applications thereof, numerous modifications and variations could be made thereto by those skilled in the art without departing from the scope of the invention set forth in the claims.

What is claimed is:

1. A motion capture system that combines sensors with different measurement ranges or resolutions comprising:
   a motion capture element comprising
      a memory;
      a plurality of sensors comprising at least two sensors that each measure a same physical quantity on two or more axes, wherein said physical quantity is equal to or is a function of one or more of a position, an orientation, a velocity, an acceleration, an angular velocity, or an angular acceleration of said motion capture element;
      a first communication interface; and,
      a microprocessor coupled with said memory, said plurality of sensors, and said first communication interface, wherein said microprocessor is configured to
         collect sensor data from said plurality of sensors, wherein said sensor data comprises a sensor value from each sensor of said plurality of sensors;
         store said sensor data in said memory; and,
         optionally transmit said sensor data to a computer via said first communication interface;
      wherein
         each sensor of said at least two sensors comprises
            a measurement range that optionally comprises
               a closed interval between a lower measurable value and an upper measurable value, said measurement range having an interior comprising measurable values that are strictly greater than said lower measurable value and strictly less than said upper measurable value; and,
            a measurement resolution;
         said measurement range or said measurement resolution or both said measurement range and said measurement resolution associated with each sensor of said at least two sensors differs from the measurement range or the measurement resolution or both the measurement range and the measurement resolution associated with at least one other sensor of said at least two sensors;
   wherein said microcomputer or said computer is configured to
      calculate a combined estimate of said physical quantity from said sensor data; and,
      analyze a motion of said motion capture element based on said sensor data and on said combined estimate of said physical quantity.

2. The system of claim 1 wherein said calculate said combined estimate of said physical quantity from said sensor data comprises
   calculate an individual sensor estimate of said physical quantity from said sensor value associated with each sensor of said at least two sensors; and,
   combine the individual sensor estimate across said at least two sensors to form said combined estimate of said physical quantity.

3. The system of claim 1 wherein
   said plurality of sensors comprises at least one rate gyroscope;
   said at least two sensors that each measure the same physical quantity comprise a plurality of accelerometers; and,
   a first accelerometer in said plurality of accelerometers comprises an upper measurable value of 24 g or lower.

4. The system of claim 3 wherein
   a second accelerometer in said plurality of accelerometers comprises an upper measurable value of 100 g or higher.

5. The system of claim 1 wherein
   said plurality of sensors comprises at least one rate gyroscope;
   said at least two sensors that each measure the same physical quantity comprise a plurality of accelerometers; and,
   a first accelerometer in said plurality of accelerometers comprises an upper measurable value of 16 g or lower.

6. The system of claim 5 wherein
   a second accelerometer in said plurality of accelerometers comprises an upper measurable value of 400 g or higher.

7. The system of claim 2 wherein said combine the individual sensor estimate across said at least two sensors comprises
   determine whether the sensor value associated with each sensor of said at least two sensors is in said interior of said measurement range associated with said each sensor; and,
   when only one sensor value is in said interior of said measurement range, set said combined estimate of said physical quantity to said only one sensor value.

8. The system of claim 7 wherein said combine the individual sensor estimate across said at least two sensors further comprises
   when multiple sensor values are in said interior of said measurement range for the associated sensor, set said combined estimate of said physical quantity to a sensor value associated with a sensor that comprises a finest measurement resolution.

9. The system of claim 7 wherein
   each sensor of said at least two sensors comprises an associated measurement variance; and, said combine the individual sensor estimate across said at least two sensors further comprises
  when multiple sensor values are in said interior of said measurement range for the associated sensor, set said combined estimate of said physical quantity to a weighted average of said multiple sensor values, with weights inversely proportional to said measurement variance for the associated sensor.

10. The system of claim 9 wherein
said each sensor of said at least two sensors further comprises an associated measurement resolution that represents a difference between successive measurement values of said each sensor; and,
said measurement variance is proportional to a square of said measurement resolution.

11. The system of claim 1 wherein one or both of said computer and said microprocessor are further configured to track said sensor data over time;
analyze said sensor data over time to determine whether one or more sensors of said at least two sensors are out of calibration; and,
send a calibration required signal when said one or more sensors of said at least two sensors are out of calibration.

12. The system of claim 11 wherein said analyze said sensor data over time comprises perform a paired t-test on sensor data samples, wherein
each sensor data sample of said sensor data samples comprises
  a first sensor value associated with a first sensor of said at least two sensors, wherein said first sensor value is in said interior of said measurement range of said first sensor;
  a second sensor value associated with a second sensor of said at least two sensors, wherein said second sensor value is in said interior of said measurement range of said second sensor; and,
wherein said first sensor value and said second sensor value were measured at substantially a same time.

13. The system of claim 2 wherein said individual sensor estimate for a sensor of said at least two sensors is calculated as
said sensor value when said sensor value is in said interior of said measurement range of said sensor; and,
an extrapolated value based on extrapolation of one or more previous or subsequent sensor values in said interior of said measurement range when said sensor value is equal to said lower measurable value for said sensor or is equal to said upper measurable value for said sensor.

14. The system of claim 13 wherein said extrapolation fits a polynomial curve to said one or more previous or subsequent sensor values.

15. The system of claim 13 wherein said combine the individual sensor estimate across said at least two sensors comprises
set said combined estimate of said physical quantity to a weighted average of said individual sensor estimate across said at least two sensors, wherein each individual sensor estimate comprises an associated weight; and,
when said individual sensor estimate is said extrapolated value, set said associated weight for said extrapolated value to a decreasing function of a distance between said extrapolated value and said measurement range of said sensor.

16. The system of claim 15 wherein said associated weight for said extrapolated value is zero when said distance between said extrapolated value and said measurement range of said sensor exceeds a threshold.

* * * * *